US007595058B2

(12) United States Patent
Murdin et al.

(10) Patent No.: US 7,595,058 B2
(45) Date of Patent: Sep. 29, 2009

(54) CHLAMYDIA ANTIGENS AND VACCINE USES OF THE PROTEIN

(75) Inventors: Andrew D. Murdin, Richmond Hill (CA); Raymond P. Oomen, Aurora (CA); Joe Wang, Toronto (CA); Pamela Dunn, Woodbridge (CA)

(73) Assignee: Sanofi Pasteur Limited, Toronto, Ontario (CA)

( * ) Notice: Subject to any disclaimer, the term of this patent is extended or adjusted under 35 U.S.C. 154(b) by 0 days.

(21) Appl. No.: 11/118,381

(22) Filed: May 2, 2005

(65) Prior Publication Data

US 2005/0202048 A1 Sep. 15, 2005

Related U.S. Application Data

(60) Division of application No. 10/608,559, filed on Jun. 30, 2003, now Pat. No. 7,070,792, which is a continuation of application No. 09/564,479, filed on May 3, 2000, now abandoned.

(60) Provisional application No. 60/132,270, filed on May 3, 1999, provisional application No. 60/141,276, filed on Jun. 30, 1999.

(51) Int. Cl.
*A61K 39/118* (2006.01)
(52) U.S. Cl. .............. 424/263.1; 424/203.1; 424/201.1; 424/185.1; 424/190.1; 424/192.1; 424/193.1; 530/350; 435/975
(58) Field of Classification Search .............. 424/263.1, 424/203.1, 201.1, 185.1, 190.1, 192.1, 193.1; 530/350; 435/975
See application file for complete search history.

(56) References Cited

U.S. PATENT DOCUMENTS

| | | | |
|---|---|---|---|
| 5,283,185 A * | 2/1994 | Epand et al. ................. 435/458 |
| 6,521,745 B1 | 2/2003 | Murdin et al. | |
| 6,559,294 B1 | 5/2003 | Griffais et al. | |
| 6,693,087 B1 | 2/2004 | Murdin et al. | |
| 6,808,713 B1 | 10/2004 | Murdin et al. | |
| 6,822,071 B1 | 11/2004 | Stephens et al. | |
| 7,019,125 B2 | 3/2006 | Murdin et al. | |
| 7,081,245 B2 | 7/2006 | Murdin et al. | |
| 2002/0082402 A1 | 6/2002 | Murdin et al. | |
| 2002/0094340 A1 | 7/2002 | Murdin et al. | |
| 2002/0094965 A1 | 7/2002 | Murdin et al. | |
| 2002/0099188 A1 | 7/2002 | Murdin et al. | |
| 2002/0132994 A1 | 9/2002 | Murdin et al. | |
| 2003/0100706 A1 | 5/2003 | Murdin et al. | |
| 2004/0254130 A1 | 12/2004 | Murdin et al. | |

FOREIGN PATENT DOCUMENTS

| | | | |
|---|---|---|---|
| EP | 0 784 059 A | | 7/1997 |
| WO | 88/09336 | * | 12/1988 |
| WO | 96/14831 | * | 5/1996 |
| WO | WO 98/58953 A | | 12/1998 |
| WO | WO 99/28475 | | 6/1999 |
| WO | WO 00/24765 | | 5/2000 |
| WO | WO00/27994 | | 5/2000 |
| WO | WO 00/34483 | | 6/2000 |
| WO | WO 00/37494 | | 6/2000 |
| WO | WO 00/46359 | | 8/2000 |
| WO | WO 00/66739 | | 11/2000 |
| WO | WO 01/21804 A1 | | 3/2001 |
| WO | WO 01/21811 A1 | | 3/2001 |
| WO | WO 01/40474 A2 | | 6/2001 |
| WO | WO 01/46224 A2 | | 6/2001 |
| WO | WO 01/81379 A2 | | 11/2001 |
| WO | WO 01/85972 A2 | | 11/2001 |
| WO | WO 02/02606 A2 | | 1/2002 |
| WO | WO 02/08267 A2 | | 1/2002 |

OTHER PUBLICATIONS

Bowie et al., "Deciphering the Message in Protein Sequences: Tolerance to Amino Acid Substitutions," Science, Colume 247, pp. 1306-1310 (1990).*
Mikayama et al. (Nov. 1993. Proc.Natl.Acad.Sci. USA, vol. 90 : 10056-10060.*
Rudinger et al. (Jun. 1976. Peptide Hormones. Biol.Council. pp. 5-7).*
Wood (Guide to Molecular Cloning Techniques. vol. 152. 1987. Section IX. Chapter 49, pp. 443-447).*
Murphy et al. Pediatr. Infect. Dis. J. 1989. 8: S66-S68.*
Yamanaka et al (J. Pediatrics. 1993. 122(2): 212-218).*
Grayston et al., "Evidence That *Chlamydia pneumoniae* Causes Pneumonia And Bronchitis", *The Journal of Infectious Diseases*, vol. 168(5):1231-1491, (1993).
Campos et al., "a Chlamydial Major Outer Membrane Protein Extract As A Trachoma Vaccine Candidate", *Investigative Ophthalmology & Visual Science*, vol. 36(8): (1995).
Grayston et al., "A New Respiratory Tract Pathogen: *Chlamydia pneumoniae* Strain TWAR", *The Journal of Infectious Diseases*, vol. 161, pp. 618-625, (1990).
T. Marrie, "State-of-the-Art Clinical Article", *Clinical Infectious Diseases*, vol. 18, pp. 501-515, (1994).
Wang et al., "Microimmunofluorescence Serological Studies With The Twar Organism", *Chlamydial Infections*, pp. 329-333, (1986).
Saikku et al., "Serological Evidence Of An Association Of A Novel Chlamydia, Twar, With Chronic Coronary Heart Disease And Acute Myocardial Infarction", *The Lancet*, pp. 983-985, (1988).
Thom et al., "Association of Prior Infection With *Chlamydia pneumoniae* And Angiographically Demonstrated Coronary Artery Disease", *JAMA*, vol. 268(1):68-72.

(Continued)

*Primary Examiner*—Jennifer E Graser

(57) ABSTRACT

The present invention provides vaccines and methods for immunizing a host, including humans, against disease caused by infection by a strain of *Chlamydia*, specifically *C. pneumoniae*. The vaccine and method employ a full-length, 5'-truncated or 3'-truncated 76kDa protein of a strain of *Chlamydia pneumoniae*. Modifications are possible within the scope of this invention.

54 Claims, 22 Drawing Sheets

OTHER PUBLICATIONS

Kuo et al., "Demonstration of *Chlamydia pneumoniae* In Atherosclerotic Lesions Of Coronary Arteries", *The Journal of Infectious Diseases*, vol. 167:841-849, (1993).
Kuo et al., "Detection of *Chlamydia pneumoniae* In Aortic Lesions of Atherosclerosis By Immunocytochemical Stain", *Arteriosclerosis and Thrombosis*, vol. 13(10):1501-1504, (1993).
Campbell et al., "Detection Of *Chlamydia pneumoniae* TWAR in Human Coronay Atherectomy Tissues", *The Journal Of Infectious Diseases*, vol. 172:585-588, (1995).
Chiu et al., "*Chlamydia pneumoniae*, Cytomegalovirus, And Herpes Simplex Virus In Atherosclerosis Of The Carotid Artery", *Circulation*, vol. 96(7):2144-2148, (1997).
Ramirez , "Isolation Of *Chlamydia Pneumoniae* From The Coronary Artery Of A Patient With Coronay Atherosclerosis", *Ann. Intern. Med.*, vol. 125:979-982, (1996).
Jackson et al., Abst. K121, p. 272, 36*th* ICAAC, Sep. 15-18, 1996, New Orleans.
Fong et al., "Rabbit Model For *Chlamydia pneumoniae* Infection", *Journal Of Clinical Microbiology*, vol. 35(1):48-52, (1997).
Hahn et al., "Evidence For *Chlamydia pneumoniae* Infection In Steroid-Dependent Asthma", *Ann. Allergy Asthma Immunol.*, vol. 80(1):45-49, (1998).
Hahn et al., "Association Of *Chlamydia pneumoniae* IgA Antibodies With Recently Symptomatic Asthma", *Epidemiol. Infect.*, vol. 117:513-517, (1996).
Bjoernsson et al., "Serology Of *Chlamydia* In Relation To Asthma And Bronchial Hyperresponsiveness", *Scand. J. Infect. Dis.*, vol. 28:63-69, (1996).
Hahn, "Treatment Of *Chlamydia pneumoniae* Infection In Adult Asthma: A Before-After Trail", *J. Fam. Pract.*, vol. 41(4):345-351, (1995).
Linnanmaeki et al., "*Chlamydia pneumoniae*-Specific Criculating Immune Complexes In Patients With Chronic Coronary Heart Disease", *Circulation*, vol. 87(4):1130-1134, (1993).
Saikku et al., "Annals Of Internal Medicine", *American College of Physicians*, vol. 116(4):273-278, (1992).
Melnick et al., "Past Infection by *Chlamydia pneumoniae* Strain TWAR and Asymptomatic Carotid Atherosclerosis", *The American Journal of Medicine*, vol. 95:499-504, (1993).
Shor et al., "Detection of *Chlamydia pneumoniae* In Coronary Arterial Fatty Streaks And Atheromatous Plaques", *South African, Medical Journal*, vol. 82:158-161, (1992).
Allegra et al., "Acute Exacerbations Of Asthma In Adults: Role Of *Chlamydia pneumoniae* Infection", *Eur.Respir. J.*, vol. 7(12): 2165-2168, (1994).
Hahn et al., "Association of *Chlamydia pneumoniae* (Strain TWAR) Infection With Wheezing, Asthmatic Bronchitis, and Adult-Onset Asthma", *JAMA*, vol. 266(2):225-230, (1991).
Pal et al., "Intranasal Immunization Induces Long-Term Protection In Mice Against A *Chlamydia trachomatis* Genital Challenge", *Infection And Immunity*, vol. 64(12):5341-5348, (1996).
Jones et al., "Efficacy Trials With Tissue-Culture Grown, Inactivated Vaccines Against Chlamydial Abortion In Sheep", *Vaccine*, vol. 13(8):715-723, (1995).
Igietseme et al., "Resolution Of Murine Chlamydial Genital Infection By The Adoptive Transfer Of A Biovar-Specific, TH1 Lymphocyte Clone", *Regional Immunology*, vol. 5:317-324, (1993).
Magee et al., "*Chlamydia trachomatis* pneumonia In The Severe Combined Immunodeficiency (SCID) Mouse", *Reg. Immunol.*, vol. 5:305-311, (1993).
Gaydos et al., "Similarity of *Chlamydia pneumoniae* Strains In The Variable Domain IV Region Of The Major Outer Membrane Protein Gene", *Infection And Immunity*, vol. 60(12):5319-5323, (1992).
Database Trembl 'Online!' EBI, Hinxton, U.K.; May 1, 1999; XP002150537; CHLPN 76 KDA HOMOLOG_1 (CT622).
Perez, Melgoza M. et al., "Isolation and Characterization of a Gene Encoding a *Chlamydia pneumoniae* 76-Kilodalton Protein Containing a Species-Specific Epitope", *Infection and Immunity* , Mar. 1, 1994, US, American Society for Microbiology, Washington, vol. 62, No. 3, pp. 880-886.
Kalman et al., *Nature Genetics*. Apr. 1999, 21:385-389.

Casey et al., "Rates Of Formation And Thermal Stabilities Of RNA:DNA and DNA:DNA Duplexes At High Concentrations of Formamide", *Nucleic Acids Research*, vol. 4(5):1539-1553, (1977).
Cagnon et al., "A New Family Of Sugar-Inducible Expression Vectors For *Escherichia coli*", *Protein Engineering*, vol. 4(7):843-847, (1991).
Wiedmann-Al-Ahmad et al., "Reactions of Polyclonal And Neutralizing Anti-p54 Monoclonal Antibodies With An Isolated, Species-Specific 54-Kilodalton Protein Of *Chlamydia pneumoniae*", *Clinical And Diagnostic Laboratory Immunology*, vol. 4(6):700-704, (1997).
Hughes et al., "Synthetic Peptides Representing Epitopes Of Outer Membrane Protein F Of *Pseudomonas aeruginosa* That Elicit Antibodies Reactive With Whole Cells Of Heterologous Immunotype Strains of *P.aeruginosa*", vol. 60(9):3497-3503, (1992).
Dion et al., "Virus Envelope-Based Peptide Vaccine Against Virus-Induced Mammary Tumors", *Virology*, vol. 179:474-477, (1990).
Snijders et al., "Identification Of Linear Epitopes On Semliki Forest Virus E2 Membrane Protein And Their Effectiveness As A Synthetic Peptide Vaccine", *Journal of General Virology*, vol. 72:557-565, (1991).
Langeveld et al., "Effective Induction of Neutralizing Antibodies With The Amino Terminus Of VP2 Of Canine Parvovirus As A Synthetic Peptide", *Vaccine*, vol. 12(15):1473-1480, (1994).
Ausubel et al., "Analysis Of DNA Sequences By Blotting And Hybridization", *Current Protocols In Molecular Biology*, pp. 2.9.1-2.9.15, (1994).
Klunkel, "Rapid And Efficient Site-Specific Mutagenesis Without Phenotypic Selection", *Proc. Natl. Acad. Sci. USA*, vol. 82:488-492, (1985).
Silhavy et al., "Experiments With Gene Fusions", *Cold Spring Harbor Laboratory*, pp. 191-195, (1984).
Landers et al., "Role of L3T4-Bearing T-Cell Populations In Experimental Murine *Chlamydial salpingitis*", *Infection and Immunity*, vol. 59(10):3774-3777, (1991).
Magee et al., "Role Of CD8 T Cells In Primary *Chlamydia* Infection", *Infection and Immunity*, vol. 63(2):516-521, (1995).
Cotter et al., "Protective Efficacy of Major Outer Membrane Protein-Specific Immunoglobulin A (IgG Monoclonal Antibodies In A Murine Model Of *Chlamydia trachomatis* Genital Tract Infection", *Infection And Immunity*, vol. 63(12):4704-4714, (1995).
Campbell et al., "Structural And Antigenic Analysis Of *Chlamydia pneumoniae*", *Infection and Immunity*, vol. 58(1):93-97, (1990).
McCafferty et al., "Electrophoretic Analysis Of The Major Outer Membrane Protein Of *Chlamydia psitaci* Reveals Multimers Which Are Recognized By Protective Monoclonal Antibodies", *Infection And Immunity*, vol. 63(6):2387-2389, (1995).
Takase et al., "Genes Encoding Two Lipoprotesin In the leuS0dacA Region of the *Escherichia coli* Chromosome," *Journal of Bacteriology*, vol. 169: 5692-5699, (1987).
Melgosa et al., "Isolation and Characterization of a Gene Encoding A *Chlamydia pneumoniae* 76-Kilodalton Protein containing A Species-Specific Epitope," *Infection and Immunity* , vol. 62(3):880-886, (1994).
Campbell et al., "Serological Response to *Chlamydia pneumoniae* Infection," *FEMS Microbiology Letters* , vol. 112: 199-204, (1993).
Iijima et al., "Characterization of *Chlamydia pneumoniae* Species-Specific Proteins Immunodominant In Humans," *Journal of Clinical Microbiology*, vol. 32(3): 583-588, (1994).
http://chlamydia-www.berkeley.edu:4231/.
Bachmaier et al., "*Chlamydia* Infections and Heart Disease Linked Through Antigenic Mimicry," *Science*, vol. 283:1335-1339, (1999).
Davis et al., "A Manual For Genetic Engineering Advanced Bacterial Genetics", *Cold Spring Harbor Laboratory*, pp. 174-176, (1980).
Watson et al., "The Nucleotide Sequence of the 60kDa Cysteine Rich Outer Membrane Protein of *Chlamydia pneumoniae* Strain IOL-207," *Nucleic Acids Research*, vol. 19(17):5299 (1990).
Watson et al., "The CrP Operon of *Chlamydia psittaci* and *Chlamydia pneumoniae*," *Microbiology*, vol. 141:2489-2497 (1995).
Melgosa et al., "Outer Membrane Complex Proteins of *Chlamydia pneumoniae*," *FEMS Microbiology Letters*, vol. 112:199-204 (1993).
U.S. Appl. No. 09/857,128, filed Sep. 20, 2001, Murdin et al.
U.S. Appl. No. 09/868,987, filed Dec. 23, 1999, Murdin et al.
U.S. Appl. No. 09/471,194, filed Dec. 23, 1999, Murdin et al.

U.S. Appl. No. 09/523,647, filed Mar. 10, 2000, Murdin et al.
U.S. Appl. No. 09/522,606, filed Mar. 10, 2000, Murdin et al.
U.S. Appl. No. 09/609,243, filed Jun. 30, 2000, Murdin et al.
U.S. Appl. No. 09/662,813, filed Sep. 15, 2000, Murdin et al.
U.S. Appl. No. 09/663,362, filed Sep. 15, 2000, Murdin et al.
U.S. Appl. No. 09/663,360, filed Sep. 15, 2000, Murdin et al.
U.S. Appl. No. 09/663,361, filed Sep. 15, 2000, Murdin et al.
U.S. Appl. No. 09/662,814, filed Sep. 15, 2000, Murdin et al.
U.S. Appl. No. 09/662,812, filed Sep. 15, 2000, Murdin et al.

U.S. Appl. No. 09/709,473, filed Nov. 13, 2000, Murdin et al.
U.S. Appl. No. 09/709,474, filed Nov. 13, 2000, Murdin et al.
U.S. Appl. No. 09/709,384, filed Nov. 13, 2000, Murdin et al.
U.S. Appl. No. 09/747,349, filed Dec. 22, 2000, Murdin et al.
Stephens et al., "Genome Sequence of an Obligate Intracellular Pathogen of Humans: *Chlamydia trachomatis*," Oct. 23, 1998, vol. 282, Science, pp. 754-759.

* cited by examiner

Figure 1:
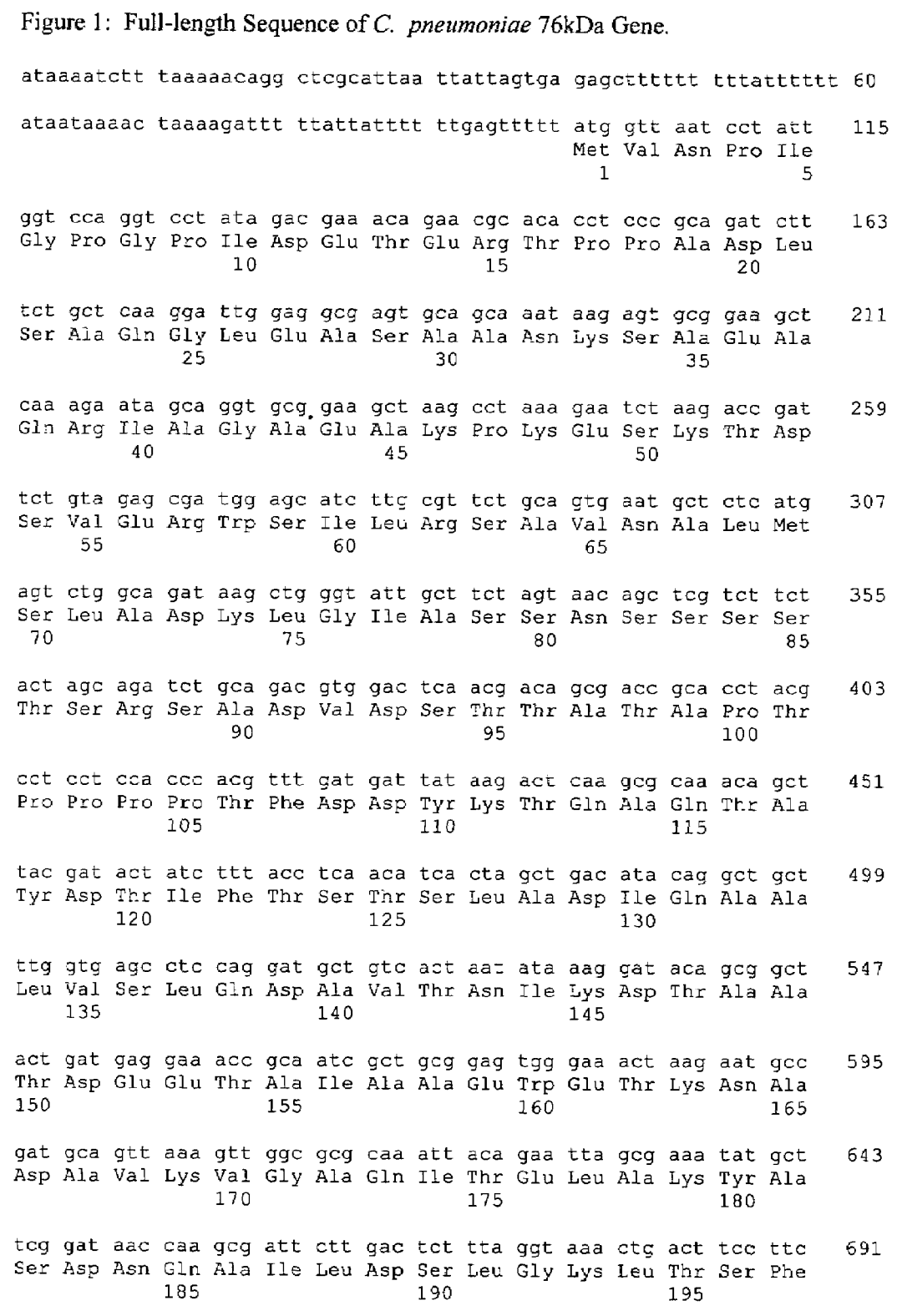

Figure 1: Full-length Sequence of *C. pneumoniae* 76kDa Gene.

```
ataaaatctt taaaaacagg ctcgcattaa ttattagtga gagcttttt tttattttt    60 ataataaaac taaaagattt ttattattt

Figure 1 (continued)

| | | | | | | | | | | | | | | | | |
|---|---|---|---|---|---|---|---|---|---|---|---|---|---|---|---|---|
| gac | ctc | tta | cag | gct | gct | ctt | ctc | caa | tct | gta | gca | aac | aat | aac | aaa | 739 |
| Asp | Leu | Leu | Gln | Ala | Ala | Leu | Leu | Gln | Ser | Val | Ala | Asn | Asn | Asn | Lys | |
| | | 200 | | | | 205 | | | | | 210 | | | | | |
| gca | gct | gag | ctt | ctt | aaa | gag | atg | caa | gat | aac | cca | gta | gtc | cca | ggg | 787 |
| Ala | Ala | Glu | Leu | Leu | Lys | Glu | Met | Gln | Asp | Asn | Pro | Val | Val | Pro | Gly | |
| | 215 | | | | | 220 | | | | | 225 | | | | | |
| aaa | acg | cct | gca | att | gct | caa | tct | tta | gtt | gat | cag | aca | gat | gct | aca | 835 |
| Lys | Thr | Pro | Ala | Ile | Ala | Gln | Ser | Leu | Val | Asp | Gln | Thr | Asp | Ala | Thr | |
| 230 | | | | | 235 | | | | | 240 | | | | | 245 | |
| gcg | aca | cag | ata | gag | aaa | gat | gga | aat | gcg | att | agg | gat | gca | tat | ttt | 883 |
| Ala | Thr | Gln | Ile | Glu | Lys | Asp | Gly | Asn | Ala | Ile | Arg | Asp | Ala | Tyr | Phe | |
| | | | | 250 | | | | | 255 | | | | | 260 | | |
| gca | gga | cag | aac | gct | agt | gga | gct | gta | gaa | aat | gct | aaa | tct | aat | aac | 931 |
| Ala | Gly | Gln | Asn | Ala | Ser | Gly | Ala | Val | Glu | Asn | Ala | Lys | Ser | Asn | Asn | |
| | | | | 265 | | | | | 270 | | | | | 275 | | |
| agt | ata | agc | aac | ata | gat | tca | gct | aaa | gca | gca | atc | gct | act | gct | aag | 979 |
| Ser | Ile | Ser | Asn | Ile | Asp | Ser | Ala | Lys | Ala | Ala | Ile | Ala | Thr | Ala | Lys | |
| | | | 280 | | | | | 285 | | | | | 290 | | | |
| aca | caa | ata | gct | gaa | gct | cag | aaa | aag | ttc | ccc | gac | tct | cca | att | ctt | 1027 |
| Thr | Gln | Ile | Ala | Glu | Ala | Gln | Lys | Lys | Phe | Pro | Asp | Ser | Pro | Ile | Leu | |
| | 295 | | | | | 300 | | | | | 305 | | | | | |
| caa | gaa | gcg | gaa | caa | atg | gta | ata | cag | gct | gag | aaa | gat | ctt | aaa | aat | 1075 |
| Gln | Glu | Ala | Glu | Gln | Met | Val | Ile | Gln | Ala | Glu | Lys | Asp | Leu | Lys | Asn | |
| 310 | | | | | 315 | | | | | 320 | | | | | 325 | |
| atc | aaa | cct | gca | gat | ggt | tct | gat | gtt | cca | aat | cca | gga | act | aca | gtt | 1123 |
| Ile | Lys | Pro | Ala | Asp | Gly | Ser | Asp | Val | Pro | Asn | Pro | Gly | Thr | Thr | Val | |
| | | | | 330 | | | | | 335 | | | | | 340 | | |
| gga | ggc | tcc | aag | caa | caa | gga | agt | agt | att | ggt | agt | att | cgt | gtt | tcc | 1171 |
| Gly | Gly | Ser | Lys | Gln | Gln | Gly | Ser | Ser | Ile | Gly | Ser | Ile | Arg | Val | Ser | |
| | | | 345 | | | | | 350 | | | | | 355 | | | |
| atg | ctg | tta | gat | gat | gct | gaa | aat | gag | acc | gct | tcc | att | ttg | atg | tct | 1219 |
| Met | Leu | Leu | Asp | Asp | Ala | Glu | Asn | Glu | Thr | Ala | Ser | Ile | Leu | Met | Ser | |
| | | 360 | | | | | 365 | | | | | 370 | | | | |
| ggg | ttt | cgt | cag | atg | att | cac | atg | ttc | aat | acg | gaa | aat | cct | gat | tct | 1267 |
| Gly | Phe | Arg | Gln | Met | Ile | His | Met | Phe | Asn | Thr | Glu | Asn | Pro | Asp | Ser | |
| | 375 | | | | | 380 | | | | | 385 | | | | | |
| caa | gct | gcc | caa | cag | gag | ctc | gca | gca | caa | gct | aga | gca | gcg | aaa | gcc | 1315 |
| Gln | Ala | Ala | Gln | Gln | Glu | Leu | Ala | Ala | Gln | Ala | Arg | Ala | Ala | Lys | Ala | |
| 390 | | | | | 395 | | | | | 400 | | | | | 405 | |
| gct | gga | gat | gac | agt | gct | gct | gca | gcg | ctg | gca | gat | gct | cag | aaa | gct | 1363 |
| Ala | Gly | Asp | Asp | Ser | Ala | Ala | Ala | Ala | Leu | Ala | Asp | Ala | Gln | Lys | Ala | |
| | | | | 410 | | | | | 415 | | | | | 420 | | |

Figure 1 (continued)

```
tta gaa gcg gct cta ggt aaa gct ggg caa caa cag ggc ata ctc aat    1411
Leu Glu Ala Ala Leu Gly Lys Ala Gly Gln Gln Gln Gly Ile Leu Asn
            425                 430                 435 gct tta gga cag atc gct tct gct gct gtt gtg agc gca gga gtt cct    1459
Ala Leu Gly Gln Ile Ala Ser Ala Ala Val Val Ser Ala Gly Val Pro
            440                 445                 450 ccc gct gca gca agt tct ata ggg tca tct gta aaa cag ctt tac aag    1507
Pro Ala Ala Ala Ser Ser Ile Gly Ser Ser Val Lys Gln Leu Tyr Lys
    455                 460                 465 acc tca aaa tct aca ggt tct gat tat aaa aca cag ata tca gca ggt    1555
Thr Ser Lys Ser Thr Gly Ser Asp Tyr Lys Thr Gln Ile Ser Ala Gly
470                 475                 480                 485 tat gat gct tac aaa tcc atc aat gat gcc tat ggt agg gca cga aat    1603
Tyr Asp Ala Tyr Lys Ser Ile Asn Asp Ala Tyr Gly Arg Ala Arg Asn
                490                 495                 500 gat gcg act cgt gat gtg ata aac aat gta agt acc ccc gct ctc aca    1651
Asp Ala Thr Arg Asp Val Ile Asn Asn Val Ser Thr Pro Ala Leu Thr
            505                 510                 515 cga tcc gtt cct aga gca cga aca gaa gct cga gga cca gaa aaa aca    1699
Arg Ser Val Pro Arg Ala Arg Thr Glu Ala Arg Gly Pro Glu Lys Thr
            520                 525                 530 gat caa gcc ctc gct agg gtg att tct ggc aat agc aga act ctt gga    1747
Asp Gln Ala Leu Ala Arg Val Ile Ser Gly Asn Ser Arg Thr Leu Gly
    535                 540                 545 gat gtc tat agt caa gtt tcg gca cta caa tct gta atg cag atc atc    1795
Asp Val Tyr Ser Gln Val Ser Ala Leu Gln Ser Val Met Gln Ile Ile
550                 555                 560                 565 cag tcg aat cct caa gcg aat aat gag gag atc aga caa aag ctt aca    1843
Gln Ser Asn Pro Gln Ala Asn Asn Glu Glu Ile Arg Gln Lys Leu Thr
                570                 575                 580 tcg gca gtg aca aag cct cca cag ttt ggc tat cct tat gtg caa ctt    1891
Ser Ala Val Thr Lys Pro Pro Gln Phe Gly Tyr Pro Tyr Val Gln Leu
            585                 590                 595 tct aat gac tct aca cag aag ttc ata gct aaa tta gaa agt ttg ttt    1939
Ser Asn Asp Ser Thr Gln Lys Phe Ile Ala Lys Leu Glu Ser Leu Phe
            600                 605                 610 gct gaa gga tct agg aca gca gct gaa ata aaa gca ctt tcc ttt gaa    1987
Ala Glu Gly Ser Arg Thr Ala Ala Glu Ile Lys Ala Leu Ser Phe Glu
    615                 620                 625 acg aac tcc ttg ttt att cag cag gtg ctg gtc aat atc ggc tct cta    2035
Thr Asn Ser Leu Phe Ile Gln Gln Val Leu Val Asn Ile Gly Ser Leu
630                 635                 640                 645
```

Figure 1 (continued)

```
tat tct ggt tat ctc caa taacaacacc taagtgttcg tttggagaga        2083
Tyr Ser Gly Tyr Leu Gln
                650 ttattatgtg ctttggtaag gcctttgttg aggccttacc aacacactag aacgatcttc 2143 ataaataaa aga                                                    2156
```

Figure 2: Restriction enzyme map of *C. pneumoniae* 76kDa gene.

Figure 2 (continued)

```
                                                                TspRI
                                                              BstAPI|
                                                       BtsI      ||
                                     HaeIV             PstI      ||
        DdeI           SfcI          Hin4I             CviRI |   ||
   HinfI  |        HinfI  |          BccI |            SfcI  | | ||
   TfiI   |        TfiI   |          TaqII | |         SfaNI | | |MwoI|
   |      |        |      |          |     | |         |    | | |   ||
     TAAAGAATCTAAGACCGATTCTGTAGAGCGATGGAGCATCTTGCGTTCTGCAGTGAATGC
241  ---------+---------+---------+---------+---------+---------+ 300
     ATTTCTTAGATTCTGGCTAAGACATCTCGCTACCTCGTAGAACGCAAGACGTCACTTACG AluI
      HinfI                                CviJI
      NlaIII                             BbsI    |
   Hpy178III |                           MboII   |
     RcaI  | |          AluI             MaeIII  | |       BfaI
   BsmI  | | |      PleI CviJI           BfaI |  | |       AceIII |
   |   | | | |      |    |               |    |  | |       |      | |
     TCTCATGAGTCTGGCAGATAAGCTGGGTATTGCTTCTAGTAACAGCTCGTCTTCTACTAG
301  ---------+---------+---------+---------+---------+---------+ 360
     AGAGTACTCAGACCGTCTATTCGACCCATAACGAAGATCATTGTCGAGCAGAAGATGATC HinfI
             Hin4I  |
           BtrI  |  |
          MaeII|  |  |
          PleI||  |  |
          PstI|||  |  |
        CviRI ||||  |  |
        SfcI  | ||||  |  |
        DpnI  | | ||||  |  |                                 Bce83I
   BglII  |   | | ||||  |  |        BseRI                    MnlI   |
   BstYI  |   | | | |||| | |        AciI   |                 MaeII|  |
   Sau3AI |   | | | |||| | |        BsiEI  |      BsaXI      MnlI || |
   |      |   | | | |||| | |        |       |      |         |   ||| |
     CAGATCTGCAGACGTGGACTCAACGACAGCGACCGCACCTACGCCTCCTCCACCCACGTT
361  ---------+---------+---------+---------+---------+---------+ 420
     GTCTAGACGTCTGCACCTGAGTTGCTGTCGCTGGCGTGGATGCGGAGGAGGTGGGTGCAA SmlI
           HinfI  |           AluI
      PsiI  |  |              CviJI
      PleI  |  |            MwoI  |                         BfaI
      TaqII |  |         HhaI |   |  Tth111II               MnlI|
      |   | |  |         |    |   |   |                     |   ||
     TGATGATTATAAGACTCAAGCGCAAACAGCTTACGATACTATCTTTACCTCAACATCACT
421  ---------+---------+---------+---------+---------+---------+ 480
     ACTACTAATATTCTGAGTTCGCGTTTGTCGAATGCTATGATAGAAATGGAGTTGTAGTGA
```

Figure 2 (continued)

```
                            HphI
            Fnu4HI          ScrFI  |
   AluI     BpmI|           EcoRII |  |MaeIII
   CviJI    CviJI|          CviJI  |  |Tsp45I    BciVI
   BbvI|    TseI|           SfaNI  |  |  |MnlI|  FokI  |
   ||       ||              |  |   |  |  |  |   |  |
       AGCTGACATACAGGCTGCTTTGGTGAGCCTCCAGGATGCTGTCACTAATATAAAGGATAC
481 ---------+---------+---------+---------+---------+---------+ 540
       TCGACTGTATGTCCGACGAAACCACTCGGAGGTCCTACGACAGTGATTATATTTCCTATG

MnlI
       CviJI  |                     AciI
       Fnu4HI |  |                  Fnu4HI |
         TauI |  |                  BstAPI|  |
         AciI |  |                  MwoI|   |     SfaNI      CviRI
       MspAI| |  |   BbvI AciI      TseI|   |     DdeI|      BsmI   |
         || | |  |    |    |        ||  |   |     ||          |    |
       AGCGGCTACTGATGAGGAAACCGCAATCGCTGCGGAGTGGGAAACTAAGAATGCCGATGC
541 ---------+---------+---------+---------+---------+---------+ 600
       TCGCCGATGACTACTCCTTTGGCGTTAGCGACGCCTCACCCTTTGATTCTTACGGCTACG

Tsp509I
                HhaI  |
                Cac8I |  |
                HhaI  |  |                                    PleI
                ThaI  |  |               Hpy188IX             Hinf|
       MseI   BssHII |  | |  Tsp509I     MwoI       |         Tfi|
        |      ||||   |           |              |            ||
       AGTTAAAGTTGGCGCGCAAATTACAGAATTAGCGAAATATGCTTCGGATAACCAAGCGAT
601 ---------+---------+---------+---------+---------+---------+ 660
       TCAATTTCAACCGCGCGTTTAATGTCTTAATCGCTTTATACGAAGCCTATTGGTTCGCTA Fnu4HI
                                              CviJI|
                                              MnlI|
                                              TseI|
                                     MboII    ||
       HinfI                  BbvI    BslI|   ||       EarI
       Hpy178III |            TaqI|   EcoNI|| ||       SapI     SfcI
        | |                   ||   | ||    ||          |         |
       TCTTGACTCTTTAGGTAAACTGACTTCCTTCGACCTCTTACAGGCTGCTCTTCTCCAATC
661 ---------+---------+---------+---------+---------+---------+ 720
       AGAACTGAGAAATCCATTTGACTGAAGGAAGCTGGAGAATGTCCGACGAGAAGAGGTTAG
```

Figure 2 (continued)

```
                              MseI
                              BbvI |
                       SfaNI  | |
                       AluI | | |
                       CviJI| | |
            Bpu1102I   | | | |
                DdeI   | | | |
                AluI|  | | | |
                CviJI| | | | |
               MspA1I| | | | |
                PvuII| | | | |
             Tth111II|| | | | |
                Fnu4HI||| | | | |        BsmFI      BmrI
           BseMII TseI||||| | | | |      CviRI|     BsrI|
                 |  ||||| | | | |           ||         ||
        TGTAGCAAACAATAACAAAGCAGCTGAGCTTCTTAAAGAGATGCAAGATAACCCAGTAGT
    721 ---------+---------+---------+---------+---------+---------+ 780
        ACATCGTTTGTTATTGTTTCGTCGACTCGAAGAATTTCTCTACGTTCTATTGGGTCATCA

Hpy188IX
      ScrFI         MunI                DpnI  |
      BsaJI|        Tsp509I             BclI  | |
      BsaJI||       CviRI|              Sau3AI | |
      EcoRII||      Cac8I ||            SfaNI | |         SfcI
         |||        | ||                 | | |              |
        CCCAGGGAAAACGCCTGCAATTGCTCAATCTTTAGTTGATCAGACAGATGCTACAGCGAC
    781 ---------+---------+---------+---------+---------+---------+ 840
        GGGTCCCTTTTGCGGACGTTAACGAGTTAGAAATCAACTAGTCTGTCTACGATGTCGCTG

CviRI
                                            FokI
                                            CjePI|
                                    BstAPI  | |
                                    NsiI    | | |
                Bccl SfaNI          CviRI |MwoI | |   AceIII   BfaI
                 |    |              |  |  | ||       |         |
        ACAGATAGAGAAAGATGGAAATGCGATTAGGGATGCATATTTTGCAGGACAGAACGCTAG
    841 ---------+---------+---------+---------+---------+---------+ 900
        TGTCTATCTCTTTCTACCTTTACGCTAATCCCTACGTATAAAACGTCCTGTCTTGCGATC SfcI
        AluI|                                            Fnu4HI
        CviJI|                        HinfI  AluI   MwoI|
        MwoI ||     CjePI      TaaI   TfiI   CviJI  TseI|
         |  ||       |          |      |       |      ||
        TGGAGCTGTAGAAAATGCTAAATCTAATAACAGTATAAGCAACATAGATTCAGCTAAAGC
    901 ---------+---------+---------+---------+---------+---------+ 960
        ACCTCGACATCTTTTACGATTTAGATTATTGTCATATTCGTTGTATCTAAGTCGATTTCG
```

Figure 2 (continued)

```
                                                                  Tsp509I
                                                        Sth132I     |
                                                         MboII|     |
                                                         HinfI ||   |
                                        Hpy188IX         Eco57I |   ||  |
                                          DdeI  |       BseMII| |   ||  |
                      DdeI          AluI  AluI| |         PleI ||  |||  |
          MwoI  BbvI   |            CviJI CviJI| |  XmnI   |   ||  | ||  |
           |     |     |              |     ||| |    |    |   ||  | ||  |
          AGCAATCGCTACTGCTAAGACACAAATAGCTGAAGCTCAGAAAAAGTTCCCCGACTCTCC
     961  ---------+---------+---------+---------+---------+---------+ 1020
          TCGTTAGCGATGACGATTCTGTGTTTATCGACTTCGAGTCTTTTTCAAGGGGCTGAGAGG MseI
                                                      DpnI |
                                                     BglII |  |
                                          DdeI       BstYI |  |
          Hpy178III AciI      BseMII      CviJI|     Sau3AI |  |
             |       |          |           | |        |    |  |
          AATTCTTCAAGAAGCGGAACAAATGGTAATACAGGCTGAGAAAGATCTTAAAAATATCAA
    1021  ---------+---------+---------+---------+---------+---------+ 1080
          TTAAGAAGTTCTTCGCCTTGTTTACCATTATGTCCGACTCTTTCTAGAATTTTTATAGTT Hpy188IX
                 DrdII |
                 BccI  |  |
                 BspMI |  |            ScrFI
                 BslI  | |  |            BslI|
                 PstI| | |  |           EcoRII||     TaaI        NgoGV
          CviRI  ||  | |  |            CjeI |||     MnlI |       NlaIV
          SfcI  |  ||  |  |     MmeI   |  |  |||    SfcI |  |    CviJI|      CjeI
            |   |  ||  |  |       |    |  |  |||     |  |  |      ||        |
          ACCTGCAGATGGTTCTGATGTTCCAAATCCAGGAACTACAGTTGGAGGCTCCAAGCAACA
    1081  ---------+---------+---------+---------+---------+---------+ 1140
          TGGACGTCTACCAAGACTACAAGGTTTAGGTCCTTGATGTCAACCTCCGAGGTTCGTTGT NlaIII         BsaI
          Tth111II                      SfaNI          BsmAI       AciI
              |                           |              |           |
          AGGAAGTAGTATTGGTAGTATTCGTGTTTCCATGCTGTTAGATGATGCTGAAAATGAGAC
    1141  ---------+---------+---------+---------+---------+---------+ 1200
          TCCTTCATCATAACCATCATAAGCACAAAGGTACGACAATCTACTACGACTTTTACTCTG NlaIII
                                      AflIII   |
                                      BspLU11I |
                                         HinfI |   |           Hpy178III
            MslI          Hpy188IX TfiI  |NspI  Bce83I    BbvI  |
              |             |       |   |  |     |        |    | |
          CGCTTCCATTTTGATGTCTGGGTTTCGTCAGATGATTCACATGTTCAATACGGAAAATCC
    1201  ---------+---------+---------+---------+---------+---------+ 1260
          GCGAAGGTAAAACTACAGACCCAAAGCAGTCTACTAAGTGTACAAGTTATGCCTTTTAGG
```

Figure 2 (continued)

```
                              Fnu4HI          Fnu4HI           BbvI
                               TseI|           MwoI|           BbvI |
                              BanII ||          TseI|         MspA1I |
                             BsiHKAI ||         BbvI ||         AciI | |
                             Bsp1286I ||        CjePI|  ||     Fnu4HI | |
                    Fnu4HI    Cac8I ||          BfaI|  ||       TauI | |
             SmlI AluI|       SacI  ||         AluI|||  ||      CviJI| | |
      HinfI    |CviJI|        AluI  | ||        CviJI|||  ||    MwoI| | |
      TfiI   | TseI|          CviJI |  || MwoI |||| ||  MwoI || | |
        |   |   ||              |  | ||   |  ||||  ||   | || | |
       TGATTCTCAAGCTGCCCAACAGGAGCTCGCAGCACAAGCTAGAGCAGCGAAAGCCGCTGG
  1261 ----------+---------+---------+---------+---------+---------+ 1320
       ACTAAGAGTTCGACGGGTTGTCCTCGAGCGTCGTGTTCGATCTCGTCGCTTTCGGCGACC Cac8I
                      HaeII|
                      MwoI|
                      HhaI||
                   Eco47III|||
                     PstI ||||
                    SfaNI ||||
                    BpmI| ||||
                   Fnu4HI| ||||
                    CviRI|| |||
                    MwoI|| ||||
                    TseI|| ||||
                  Fnu4HI ||| ||||
                    SfcI ||| ||||           AluI           BfaI
                    TseI| ||| ||||          CviJI          CviJI    |
                   CjePI|| ||| ||||        HindIII |      Fnu4HI  |   |
                   TspRI|| ||| ||||          MwoI|  |      TauI  |   |
                  Fnu4HI||| ||| ||||   Hpy188IX || (       AciI|  |   |
                   TseI|||| ||| ||||     DdeI  |  ||  |BseMII || | |
       BbvI   TaaI |||||  |||  ||||     BbvI   |  |   || |   MwoI || | |
         |      |  ||||| ||| ||||         |    |   |  ||  |    |  || | |
       AGATGACAGTGCTGCTGCAGCGCTGGCAGATGCTCAGAAAGCTTTAGAAGCGGCTCTAGG
  1321 ----------+---------+---------+---------+---------+---------+ 1380
       TCTACTGTCACGACGACGTCGCGACCGTCTACGAGTCTTTCGAAATCTTCGCCGAGATCC DpnI      Fnu4HI
         AluI                            Sau3AI |    MwoI|
         CviJI                            BbvI | |    TseI|
          |                                 | | |      ||
       TAAAGCTGGGCAACAACAGGGCATACTCAATGCTTTAGGACAGATCGCTTCTGCTGCTGT
  1381 ----------+---------+---------+---------+---------+---------+ 1440
       ATTTCGACCCGTTGTTGTCCCGTATGAGTTACGAAATCCTGTCTAGCGAAGACGACGACA
```

Figure 2 (continued)

```
                        FauI
                        PstI
                     Fnu4HI|
                       MnlI|
                    Sth132I|
                     CviRI||
                      TseI||
                 Fnu4HI |||
                    SfcI |||
                 MspA1I| |||
       BbvI        TseI| |||      BbvI              AluI
       HhaI |      AciI || |||    SfcI |SimI        CviJI
        | |          | || |||      | |  |           |
          TGTGAGCGCAGGAGTTCCTCCCGCTGCAGCAAGTTCTATAGGGTCATCTGTAAAACAGCT
     1441 ---------+---------+---------+---------+---------+---------+ 1500
          ACACTCGCGTCCTCAAGGAGGGCGACGTCGTTCAAGATATCCCAGTAGACATTTTGTCGA

Hpy188IX             SfaNI
            MnlI          |           EcoRV    |
          SfcI|  AlwNI|  PsiI  BspMI    |      |
           ||    ||     |       |    |  |
          TTACAAGACCTCAAAATCTACAGGTTCTGATTATAAAACACAGATATCAGCAGGTTATGA
     1501 ---------+---------+---------+---------+---------+---------+ 1560
          AATGTTCTGGAGTTTTAGATGTCCAAGACTAATATTTTGTGTCTATAGTCGTCCAATACT

Bsp1286I
                                BmgI |
                               BseSI |
                              SfaNI| |
             BccI        BslI  || |        Hpy178III
           SfaNI    |   EcoNI |  || |  PleI  BssSI   |
              | |         |   || ||    |     HinfI | |
          TGCTTACAAATCCATCAATGATGCCTATGGTAGGGCACGAAATGATGCGACTCGTGATGT
     1561 ---------+---------+---------+---------+---------+---------+ 1620
          ACGAATGTTTAGGTAGTTACTACGGATACCATCCCGTGCTTTACTACGCTGAGCACTACA DpnI                       AvaI
                           Sau3AI |                       SmlI
                          FauI  | |                       XhoI
                         AlwI|  | |                       AluI|
                      Sth132I|  | |           BsiHKAI     CviJI|
                       BsrBI ||   | |        Bsp1286I    MnlI ||
                 RsaI AciI |   || | |  BfaI             Ppil ||
                    |   | |   ||  | |    |       |        | ||
          GATAAACAATGTAAGTACCCCCGCTCTCACACGATCCGTTCCTAGAGCACGAACAGAAGC
     1621 ---------+---------+---------+---------+---------+---------+ 1680
          CTATTTGTTACATTCATGGGGCGAGAGTGTGCTAGGCAAGGATCTCGTGCTTGTCTTCG AvaII           BslI
          Sau96I      DpnI  BfaI|
          TaqI    |  Sau3AI |CviJI  BslI|MnlI     HphI
             |    |    | |   |  |    ||    |       |
          TCGAGGACCAGAAAAAACAGATCAAGCCCTCGCTAGGGTGATTTCTGGCAATAGCAGAAC
     1681 ---------+---------+---------+---------+---------+---------+ 1740
          AGCTCCTGGTCTTTTTTGTCTAGTTCGGGAGCGATCCCACTAAAGACCGTTATCGTCTTG
```

Figure 2 (continued)

```
                                              Bce83I
                                              DpnI|
                                        Sau3AI ||      TaqI
           SfcI               FokI      CviRI | ||BsrI  |
            |                  |         | | ||  |     |
         TCTTGGAGATGTCTATAGTCAAGTTTCGGCACTACAATCTGTAATGCAGATCATCCAGTC
    1741 ---------+---------+---------+---------+---------+---------+ 1800
         AGAACCTCTACAGATATCAGTTCAAAGCCGTGATGTTAGACATTACGTCTAGTAGGTCAG

CviJI
                                                              BsaXI|
                                                              Hin4I||
                                        AluI                  TspRI|||
                           Hpy188IX  CviJI       BtsI              ||||
    HinfI       MnlI        DpnI |  BseRI |     MaeIII             ||||
    TfiI SmlI   MnlI |     Sau3AI |  |HindIII |  Tsp45I            ||||
     |    |     |   |      |   | |   |  |   |     |               ||||
         GAATCCTCAAGCGAATAATGAGGAGATCAGACAAAAGCTTACATCGGCAGTGACAAAGCC
    1801 ---------+---------+---------+---------+---------+---------+ 1860
         CTTAGGAGTTCGCTTATTACTCCTCTAGTCTGTTTTCGAATGTAGCCGTCACTGTTTCGG CviJI
           MnlI    |
           BslI|   |
           PflMI|  |                                          AluI
           TaaI ||  |    CviRI   PleI  HinfI                  CviJI
             | ||   |       |      |    |                       |
         TCCACAGTTTGGCTATCCTTATGTGCAACTTTCTAATGACTCTACACAGAAGTTCATAGC
    1861 ---------+---------+---------+---------+---------+---------+ 1920
         AGGTGTCAAACCGATAGGAATACACGTTGAAAGATTACTGAGATGTGTCTTCAAGTATCG Eco57I
                                        AluI|
                                        AlwNI|
                                        CviJI|
                                        MspA1I|
                            BfaI        PvuII|
                            DpnI |    Fnu4HI ||
                            BstYI |    |  TseI| ||
    Tth111II                Sau3AI |  |AlwI  || ||      BbvI
    Tsp509I |                 | | |    |  | || ||        |
     | |                     |  |  |    |   | || ||      |
         TAAATTAGAAAGTTTGTTTGCTGAAGGATCTAGGACAGCAGCTGAAATAAAAGCACTTTC
    1921 ---------+---------+---------+---------+---------+---------+ 1980
         ATTTAATCTTTCAAACAAACGACTTCCTAGATCCTGTCGTCGACTTTATTTTCGTGAAAG AlwNI
            BspMI     AarI   |           CviJI
              |        | |                 |
         CTTTGAAACGAACTCCTTGTTTATTCAGCAGGTGCTGGTCAATATCGGCTCTCTATATTC
    1981 ---------+---------+---------+---------+---------+---------+ 2040
         GAAACTTTGCTTGAGGAACAAATAAGTCGTCCACGACCAGTTATAGCCGAGAGATATAAG
```

Figure 2 (continued)

```
                                MslI
                                DdeI|
                    BsbI          ||
                      |           ||
         TGGTTATCTCCAATAACAACACCTAAGTGTTCGTTTGGAGAGATTATTATGTGCTTTGGT
   2041  ---------+---------+---------+---------+---------+---------+ 2100
         ACCAATAGAGGTTATTGTTGTGGATTCACAAGCAAACCTCTCTAATAATACACGAAACCA

MnlI
         CviJI |      CviJI                    DpnI
         HaeI  |      HaeI              Sau3AI  |
         HaeIII|      HaeIII       MboII     |  |
         StuI  |      StuI    BsbI BfaI|     |  |
           ||         |         |    ||      |  |
         AAGGCCTTTGTTGAGGCCTTACCAACACACTAGAACGATCTTCAATAAATAAAAGA
   2101  ---------+---------+---------+---------+---------+------ 2156
         TTCCGGAAACAACTCCGGAATGGTTGTGTGATCTTGCTAGAAGTTATTTATTTTCT
```

Figure 3: Sequence Containing Truncated Version of *C. pneumoniae* 76kDa Gene; (nucleotides 1 to 665 and 2122 to 2238 are unrelated to the 76kDa Gene).

```
atgacaaaaa aacattatgc ttgggttgta gaagggattc tcaatcgttt gcctaaacag    60
ttttttgtga atgtagtgt tgtcgactgg aacacattcg ttccttcaga aacctccact    120
acagaaaaag ctgctacaaa cgctatgaaa tacaaatact gtgtttggca gtggctcgtc    180
ggaaagcata gtcaggttcc ttggatcaat ggacagaaaa agcctctata tctttatgga    240
gctttcttaa tgaacccttt agcaaaggct acgaagacta cgttaaatgg aaaagaaaac    300
ctagcttggt ttattggagg aactttaggg ggactcagaa aagctggaga ctggtctgcc    360
acagtacgtt atgagtatgt cgaagccttg tcggttccag aaatagatgt ttcagggatt    420
ggccgtggta atttattaaa gttttggttc gcccaagcaa ttgctgctaa ctatgatcct    480
aaagaggcta atggttttac aaattataaa ggattttccg ctctatatat gtatggcatc    540
acagattctc tatcattcag agcttatggg gcttactcca aaccagcaaa cgataaactc    600
ggcagtgatt ttactttccg aaagtttgat ctaggtataa tttcagcgtt ttaagtcaaa    660
ttttaataaa atctttaaaa acaggctcgc attaattatt agtgagagct ttttttttat    720
tttttataat aaaactaaaa gatttttatt attttttgag ttttt atg gtt aat cct    777
                                                  Met Val Asn Pro
                                                    1
```

```
att ggt cca ggt cct ata gac gaa aca gaa cgc aca cct ccc gca gat    825
Ile Gly Pro Gly Pro Ile Asp Glu Thr Glu Arg Thr Pro Pro Ala Asp
  5              10                  15                  20 ctt tct gct caa gga ttg gag gcg agt gca gca aat aag agt gcg gaa    873
Leu Ser Ala Gln Gly Leu Glu Ala Ser Ala Ala Asn Lys Ser Ala Glu
             25                  30                  35 gct caa aga ata gca ggt gcg gaa gct aag cct aaa gaa tct aag acc    921
Ala Gln Arg Ile Ala Gly Ala Glu Ala Lys Pro Lys Glu Ser Lys Thr
                 40                  45                  50 gat tct gta gag cga tgg agc atc ttg cgt tct gca gtg aat gct ctc    969
Asp Ser Val Glu Arg Trp Ser Ile Leu Arg Ser Ala Val Asn Ala Leu
             55                  60                  65 atg agt ctg gca gat aag ctg ggt att gct tct agt aac agc tcg tct   1017
Met Ser Leu Ala Asp Lys Leu Gly Ile Ala Ser Ser Asn Ser Ser Ser
     70                  75                  80 tct act agc aga tct gca gac gtg gac tca acg aca gcg acc gca cct   1065
Ser Thr Ser Arg Ser Ala Asp Val Asp Ser Thr Thr Ala Thr Ala Pro
 85                  90                  95                 100
```

Figure 3 (continued)

```
acg cct cct cca ccc acg ttt gat gat tat aag act caa gcg caa aca    1113
Thr Pro Pro Pro Pro Thr Phe Asp Asp Tyr Lys Thr Gln Ala Gln Thr
            105                 110                 115 gct tac gat act atc ttt acc tca aca tca cta gct gac ata cag gct    1161
Ala Tyr Asp Thr Ile Phe Thr Ser Thr Ser Leu Ala Asp Ile Gln Ala
            120                 125                 130 gct ttg gtg agc ctc cag gat gct gtc act aat ata aag gat aca gcg    1209
Ala Leu Val Ser Leu Gln Asp Ala Val Thr Asn Ile Lys Asp Thr Ala
            135                 140                 145 gct act gat gag gaa acc gca atc gct gcg gag tgg gaa act aag aat    1257
Ala Thr Asp Glu Glu Thr Ala Ile Ala Ala Glu Trp Glu Thr Lys Asn
            150                 155                 160 gcc gat gca gtt aaa gtt ggc gcg caa att aca gaa tta gcg aaa tat    1305
Ala Asp Ala Val Lys Val Gly Ala Gln Ile Thr Glu Leu Ala Lys Tyr
165                 170                 175                 180 gct tcg gat aac caa gcg att ctt gac tct tta ggt aaa ctg act tcc    1353
Ala Ser Asp Asn Gln Ala Ile Leu Asp Ser Leu Gly Lys Leu Thr Ser
            185                 190                 195 ttc gac ctc tta cag gct gct ctt ctc caa tct gta gca aac aat aac    1401
Phe Asp Leu Leu Gln Ala Ala Leu Leu Gln Ser Val Ala Asn Asn Asn
            200                 205                 210 aaa gca gct gag ctt ctt aaa gag atg caa gat aac cca gta gtc cca    1449
Lys Ala Ala Glu Leu Leu Lys Glu Met Gln Asp Asn Pro Val Val Pro
            215                 220                 225 ggg aaa acg cct gca att gct caa tct tta gtt gat cag aca gat gct    1497
Gly Lys Thr Pro Ala Ile Ala Gln Ser Leu Val Asp Gln Thr Asp Ala
            230                 235                 240 aca gcg aca cag ata gag aaa gat gga aat gcg att agg gat gca tat    1545
Thr Ala Thr Gln Ile Glu Lys Asp Gly Asn Ala Ile Arg Asp Ala Tyr
245                 250                 255                 260 ttt gca gga cag aac gct agt gga gct gta gaa aat gct aaa tct aat    1593
Phe Ala Gly Gln Asn Ala Ser Gly Ala Val Glu Asn Ala Lys Ser Asn
            265                 270                 275 aac agt ata agc aac ata gat tca gct aaa gca gca atc gct act gca    1641
Asn Ser Ile Ser Asn Ile Asp Ser Ala Lys Ala Ala Ile Ala Thr Ala
            280                 285                 290 aag aca caa ata gct gaa gct cag aaa aag ttc ccc gac tct cca att    1689
Lys Thr Gln Ile Ala Glu Ala Gln Lys Lys Phe Pro Asp Ser Pro Ile
            295                 300                 305
```

Figure 3 (continued)

```
ctt caa gaa gcg gaa caa atg gta ata cag gct gag aaa gat ctt aaa      1737
Leu Gln Glu Ala Glu Gln Met Val Ile Gln Ala Glu Lys Asp Leu Lys
    310                 315                 320 aat atc aaa cct gca gat ggt tct gat gtt cca aat cca gga act aca      1785
Asn Ile Lys Pro Ala Asp Gly Ser Asp Val Pro Asn Pro Gly Thr Thr
325                 330                 335                 340 gtt gga ggc tcc aag caa caa gga agt agt att ggt agt att cgt gtt     1833
Val Gly Gly Ser Lys Gln Gln Gly Ser Ser Ile Gly Ser Ile Arg Val
                345                 350                 355 tcc atg ctg tta gat gat gct gaa aat gag acc gct tcc att ttg atg     1881
Ser Met Leu Leu Asp Asp Ala Glu Asn Glu Thr Ala Ser Ile Leu Met
            360                 365                 370 tct ggg ttt cgt cag atg att cac atg ttc aat acg gaa aat cct gat     1929
Ser Gly Phe Arg Gln Met Ile His Met Phe Asn Thr Glu Asn Pro Asp
        375                 380                 385 tct caa gct gcc caa cag gag ctc gca gca caa gct aga gca gcg aaa     1977
Ser Gln Ala Ala Gln Gln Glu Leu Ala Ala Gln Ala Arg Ala Ala Lys
        390                 395                 400 gcc gct gga gat gac agt gct gct gca gcg ctg gca gat gct cag aaa     2025
Ala Ala Gly Asp Asp Ser Ala Ala Ala Ala Leu Ala Asp Ala Gln Lys
405                 410                 415                 420 gct tta gaa gcg gct cta ggt aaa gct ggg caa caa cag ggc ata ctc     2073
Ala Leu Glu Ala Ala Leu Gly Lys Ala Gly Gln Gln Gln Gly Ile Leu
                425                 430                 435 aat gct tta gga cag atc gct tct gct gct gtt gtg agc gca gga gta     2121
Asn Ala Leu Gly Gln Ile Ala Ser Ala Ala Val Val Ser Ala Gly Val
            440                 445                 450 ctc ccg ctg cag caa gtt cta tgg atc cga gct cgg tac caa gct tac     2169
Leu Pro Leu Gln Gln Val Leu Trp Ile Arg Ala Arg Tyr Gln Ala Tyr
        455                 460                 465 gta gaa caa aaa ctc atc tca gaa gag gat ctg aat agc gcc gtc gac     2217
Val Glu Gln Lys Leu Ile Ser Glu Glu Asp Leu Asn Ser Ala Val Asp
        470                 475                 480 cat cat cat cat cat cat tga                                          2238
His His His His His His
485                 490
```

Construction of pCACPNM555a

Construction of pCAI555

Construction of pCAD76kDa

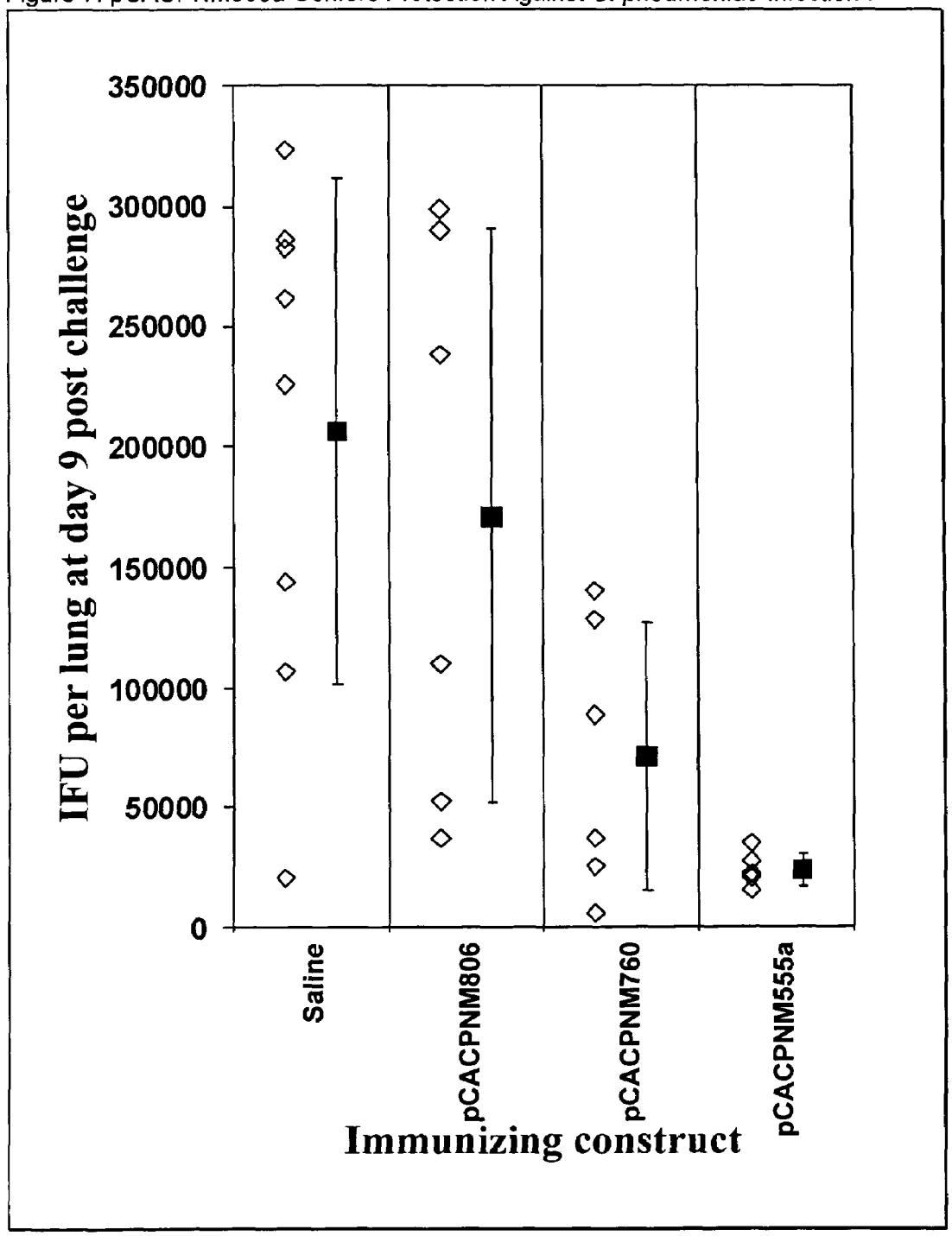
Figure 7: pCACPNM555a Confers Protection Against *C. pneumoniae* Infection.

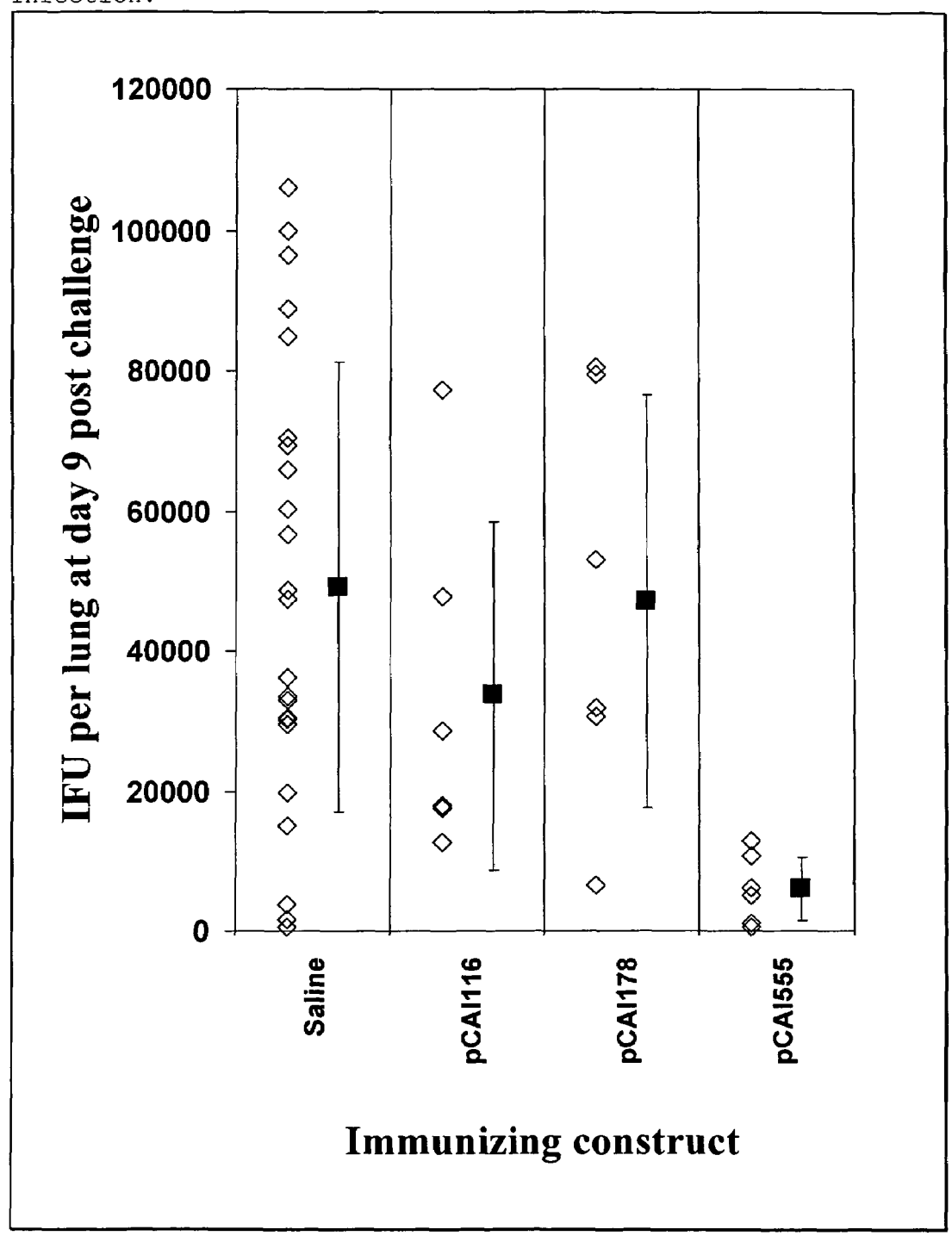
Figure 8: pCAI555 Confers Protection Against *C. pneumoniae* Infection.

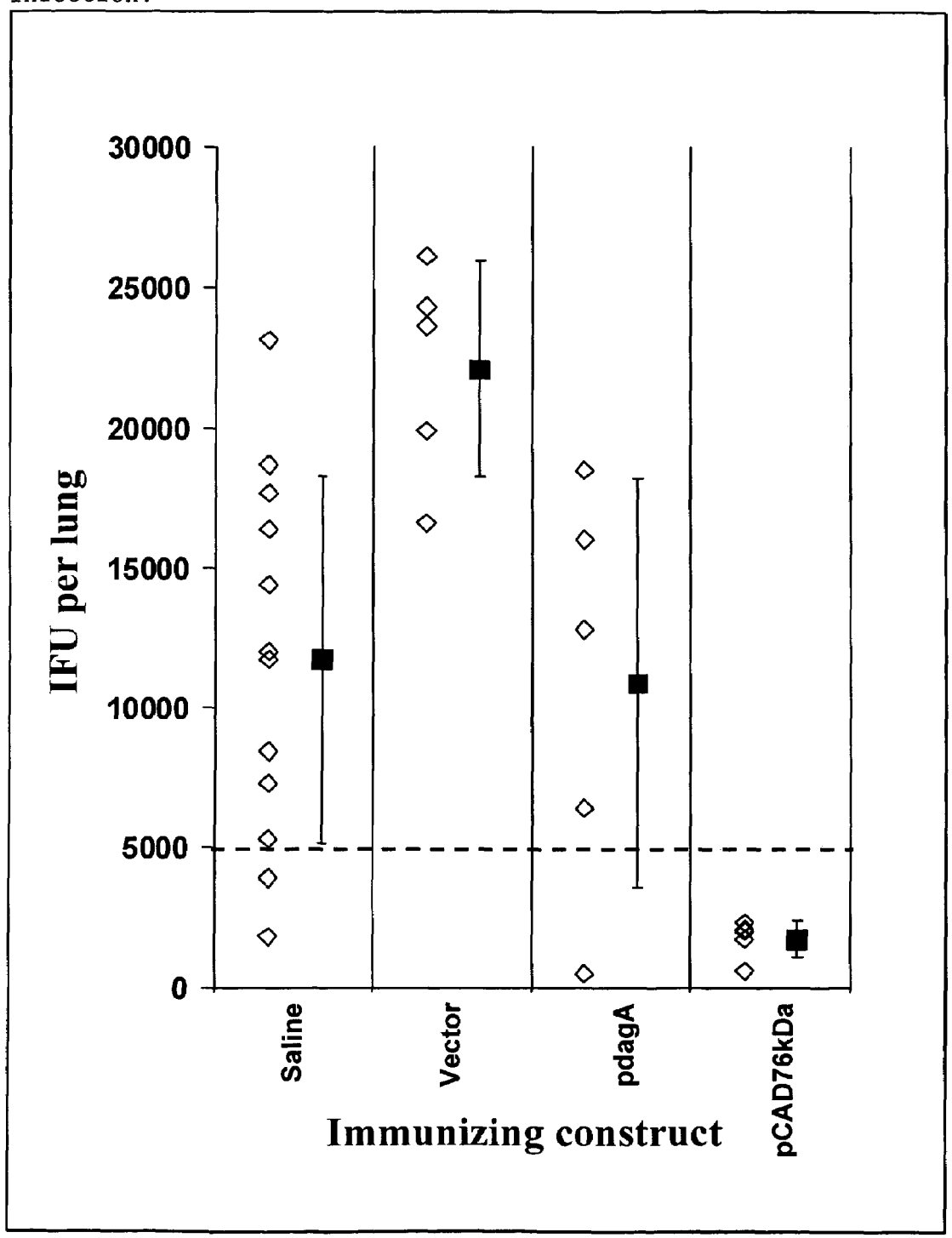
Figure 9: pCAD76kDa Confers Protection against *C. pneumoniae* Infection.

CHLAMYDIA ANTIGENS AND VACCINE USES OF THE PROTEIN

REFERENCE TO RELATED APPLICATIONS

This is a divisional application of U.S. patent application Ser. No. 10/608,559, filed Jun. 30, 2003, now U.S. Pat. No. 7.070,792, which is a continuation of U.S. patent application Ser. No. 09/564,479 filed May 3, 2000, now abandoned, which claims the benefit of U.S. Provisional Application No. 60/132,270, filed May 3, 1999, and U.S. Provisional Application No. 60/141,276 filed Jun. 30, 1999, the disclosures of which are herein incorporated by reference.

FIELD OF INVENTION

The present invention relates to the *Chlamydia* 76kDa protein and corresponding DNA molecules, which can be used to prevent and treat *Chlamydia* infection in mammals, such as humans.

BACKGROUND OF THE INVENTION

Chlamydiae are prokaryotes. They exhibit morphologic and structural similarities to gram-negative bacteria including a trilaminar outer membrane, which contains lipopolysaccharide and several membrane proteins that are structurally and functionally analogous to proteins found in *E coli*. They are obligate intra-cellular parasites with a unique biphasic life cycle consisting of a metabolically inactive but infectious extracellular stage and a replicating but non-infectious intracellular stage. The replicative stage of the life-cycle

*C. pneumoniae* is a common human pathogen, originally described as the TWAR strain of *Chlamydia psittaci* but subsequently recognised to be a new species. *C. pneumoniae* is antigenically, genetically and morphologically distinct from other *Chlamydia* species (*C. trachomatis, C. pecorum* and *C. psittaci*). It shows 10% or less DNA sequence homology with either of *C. trachomatis* or *C. psittaci*.

*C. pneumoniae* is a common cause of community acquired pneumonia, only less frequent than *Streptococcus pneumoniae* and *Mycoplasma pneumoniae* (Grayston et al. (1995) Journal of Infectious Diseases 168:1231; Campos et al. (1995) Investigation of Ophthalmology and Visual Science 36:1477). It can also cause upper respiratory tract symptoms and disease, including bronchitis and sinusitis (Grayston et al. (1995) Journal of Infectious Diseases 168:1231; Grayston et al (1990) Journal of Infectious Diseases 161:618; Marrie (1993) Clinical Infectious Diseases. 18:501; Wang et al (1986) Chlamydial infections Cambridge University Press, Cambridge. p. 329. The great majority of the adult population (over 60%) has antibodies to *C. pneumoniae* (Wang et al (1986) Chlamydial infections. Cambridge University Press, Cambridge. p. 329), indicating past infection which was unrecognized or asymptomatic.

*C. pneumoniae* infection usually presents as an acute respiratory disease (i.e., cough, sore throat, hoarseness, and fever; abnormal chest sounds on auscultation). For most patients, the cough persists for 2 to 6 weeks, and recovery is slow. In approximately 10% of these cases, upper respiratory tract infection is followed by bronchitis or pneumonia. Furthermore, during a *C. pneumoniae* epidemic, subsequent co-infection with pneumococcus has been noted in about half of these pneumonia patients, particularly in the infirm and the elderly. As noted above, there is more and more evidence that *C. pneumoniae* infection is also linked to diseases other than respiratory infections.

The reservoir for the organism is presumably people. In contrast to *C. psittaci* infections, there is no known bird or animal reservoir. Transmission has not been clearly defined. It may result from direct contact with secretions, from fomites, or from airborne spread. There is a long incubation period, which may last for many months. Based on analysis of epidemics, *C. pneumoniae* appears to spread slowly through a population (case-to-case interval averaging 30 days) because infected persons are inefficient transmitters of the organism. Susceptibility to *C. pneumoniae* is universal. Reinfections occur during adulthood, following the primary infection as a child. *C. pneumoniae* appears to be an endemic disease throughout the world, noteworthy for superimposed intervals of increased incidence (epidemics) that persist for 2 to 3 years. *C. trachomatis* infection does not confer cross-immunity to *C. pneumoniae*. Infections are easily treated with oral antibiotics, tetracycline or erythromycin (2 g/d, for at least 10 to 14 d). A recently developed drug, azithromycin, is highly effective as a single-dose therapy against Chlamydial infections.

In most instances, *C. pneumoniae* infection is often mild and without complications, and up to 90% of infections are subacute or unrecognized. Among children in industrialized countries, infections have been thought to be rare up to the age of 5 y, although a recent study (E Normann et al, *Chlamydia pneumoniae* in children with acute respiratory tract infections, Acta Paediatrica, 1998, Vol 87, Iss 1, pp 23-27) has reported that many children in this age group show PCR evidence of infection despite being seronegative, and estimates a prevalence of 17-19% in 2-4 y olds. In developing countries, the seroprevalence of *C. pneumoniae* antibodies among young children is elevated, and there are suspicions that *C. pneumoniae* may be an important cause of acute lower respiratory tract disease and mortality for infants and children in tropical regions of the world.

From seroprevalence studies and studies of local epidemics, the initial *C. pneumoniae* infection usually happens between the ages of 5 and 20 y. In the USA, for example, there are estimated to be 30,000 cases of childhood pneumonia each year caused by *C. pneumoniae*. Infections may cluster among groups of children or young adults (e.g., school pupils or military conscripts).

*C. pneumoniae* causes 10 to 25% of community-acquired lower respiratory tract infections (as reported from Sweden, Italy, Finland, and the USA). During an epidemic, *C. pneumonia* infection may account for 50 to 60% of the cases of pneumonia. During these periods, also, more episodes of mixed infections with *S. pneumoniae* have been reported.

Reinfection during adulthood is common; the clinical presentation tends to be milder. Based on population seroprevalence studies, there tends to be increased exposure with age, which is particularly evident among men. Some investigators have speculated that a persistent, asymptomatic *C. pneumoniae* infection state is common.

In adults of middle age or older, *C. pneumoniae* infection may progress to chronic bronchitis and sinusitis. A study in the USA revealed that the incidence of pneumonia caused by *C. pneumoniae* in persons younger than 60 years is 1 case per 1,000 persons per year; but in the elderly, the disease incidence rose three-fold. *C. pneumoniae* infection rarely leads to hospitalization, except in patients with an underlying illness.

Of considerable importance is the association of atherosclerosis and *C. pneumoniae* infection. There are several epidemiological studies showing a correlation of previous infections with *C. pneumoniae* and heart attacks, coronary artery and carotid artery disease (Saikku et al. (1988) Lancet;ii:983; Thom et al. (1992) JAMA 268:68; Linnanmaki et al. (1993), Circulation 87:1030; Saikku et al. (1992)Annals Internal Medicine 116:273; Melnick et al(1993) American Journal of Medicine 95:499). Moreover, the organisms has been detected in atheromas and fatty streaks of the coronary, carotid, peripheral arteries and aorta (Shor et al. (1992) South African. Medical Journal 82:158; Kuo et al. (1993) Journal of Infectious Diseases 167:841; Kuo et al. (1993) Arteriosclerosis and Thrombosis 13:1500; Campbell et al (1995) Journal of Infectious Diseases 172:585; Chiu et al. Circulation, 1997 (In Press)). Viable *C. pneumoniae* has been recovered from the coronary and carotid artery (Ramirez et al (1996) Annals of Internal Medicine 125:979; Jackson et al. Abst. K121, p272, 36[th] ICAAC, 15-18 Sep. 1996, New Orleans). Furthermore, it has been shown that *C. pneumoniae* can induce changes of atherosclerosis in a rabbit model (Fong et al (1997) Journal of Clinical Microbiolology 35:48). Taken together, these results indicate that it is highly probable that *C. pneumoniae* can cause atherosclerosis in humans, though the epidemiological importance of Chlamydial atherosclerosis remains to be demonstrated.

A number of recent studies have also indicated an association between *C. pneumoniae* infection and asthma. Infection has been linked to wheezing, asthmatic bronchitis, adult-onset asthma and acute exacerbations of asthma in adults, and small-scale studies have shown that prolonged antibiotic treatment was effective at greatly reducing the severity of the disease in some individuals (Hahn D L, et al. Evidence for *Chlamydia pneumoniae* infection in steroid-dependent asthma. Ann Allergy Asthma Immunol. January 1998; 80(1): 45-49.; Hahn D L, et al. Association of *Chlamydia pneumoniae* IgA antibodies with recently symptomatic asthma. Epidemiol Infect. December 1996; 117(3):513-517; Bjornsson E, et al. Serology of *Chlamydia* in relation to asthma and bronchial hyperresponsiveness. Scand J Infect Dis. 1996; 28(1):63-69.; Hahn D L. Treatment of *Chlamydia pneumoniae* infection in adult asthma: a before-after trial. J Fam Pract. October 1995; 41(4):345-351.; Allegra L, et al. Acute exacerbations of asthma in adults: role of *Chlamydia pneumoniae* infection. Eur Respir J. December 1994; 7(12):2165-2168.; Hahn D L, et al. Association of *Chlamydia pneumoniae* (strain TWAR) infection with wheezing, asthmatic bronchitis, and adult-onset asthma. JAMA. 1991 Jul. 10; 266 (2):225-230).

In light of these results a protective vaccine against *C. pneumoniae* infection would be of considerable importance. There is not yet an effective vaccine for any human Chlamydial infection. It is conceivable that an effective vaccine can be developed using physically or chemically inactivated Chlamydiae. However, such a vaccine does not have a high margin of safety. In general, safer vaccines are made by genetically manipulating the organism by attenuation or by recombinant means. Accordingly, a major obstacle in creating an effective and safe vaccine against human Chlamydial infection has been the paucity of genetic information regarding *Chlamydia*, specifically *C. pneumoniae*.

Studies with *C. trachomatis* and *C. psittaci* indicate that safe and effective vaccine against *Chlamydia* is an attainable goal. For example, mice which have recovered from a lung infection with *C. trachomatis* are protected from infertility induced by a subsequent vaginal challenge (Pal et al.(1996) Infection and Immunity.64:5341). Similarly, sheep immunized with inactivated *C. psittaci* were protected from subsequent Chlamydial-induced abortions and stillbirths (Jones et al. (1995) Vaccine 13:715). Protection from Chlamydial infections has been associated with Th1 immune responses, particularly the induction of INFg-producing CD4+T-cells (Igietsemes et al. (1993) Immunology 5:317). The adoptive transfer of CD4+ cell lines or clones to nude or SCID mice conferred protection from challenge or cleared chronic disease (Igietseme et al (1993) Regional Immunology 5:317; Magee et al (1993) Regional Immunology 5:305), and in vivo depletion of CD4+T cells exacerbated disease post-challenge (Landers et al (1991) Infection & Immunity 59:3774; Magee et al (1995) Infection & Immunity 63:516). However, the presence of sufficiently high titres of neutralising antibody at mucosal surfaces can also exert a protective effect (Cotter et al. (1995) Infection and Immunity 63:4704).

Antigenic variation within the species *C. pneumoniae* is not well documented due to insufficient genetic information, though variation is expected to exist based on *C. trachomatis*. Serovars of *C. trachomatis* are defined on the basis of antigenic variation in the major outer membrane protein (MOMP), but published *C. pneumoniae* MOMP gene sequences show no variation between several diverse isolates of the organism (Campbell et al (1990) Infection and Immunity 58:93; McCafferty et al (1995) Infection and Immunity 63:2387-9; Knudsen et al (1996) Third Meeting of the European Society for *Chlamydia* Research, Vienna). Melgosa et al. (Infect. Immun. 1994. 62:880) claimed to have cloned the gene encoding a 76 kDa antigen from a single strain of *C. pneumoniae*. An operon encoding the 9 kDa and 9 kDa cyteine-rich outer membrane protein genes has been described (Watson et al., Nucleic Acids Res (1990) 18:5299; Watson et al., Microbiology (1995) 141:2489). Many antigens recognized by immune sera to *C. pneumoniae* are conserved across all Chlamydiae, but 98 kDa, 76 kDa and several other proteins may be *C. pneumoniae*-specific (Perez Melgosa et al., Infect. Immun. 1994. 62:880; Melgosa et al., FEMS Microbiol Lett (1993) 112:199;, Campbell et al., J Clin Microbiol (1990) 28:1261; Iijima et al., J Clin Microbiol (1994) 32:583). An assessment of the number and relative frequency of any *C. pneumoniae* serotypes, and the defining antigens, is not yet possible. The entire genome sequence of *C. pneumoniae* strain CWL-029 is now known (http://chlamydia-www.berkeley.edu:4231/) and as further sequences become available a better understanding of antigenic variation may be gained.

Many antigens recognised by immune sera to *C. pneumoniae* are conserved across all Chlamydiae, but 98kDa, 76 kDa and 54 kDa proteins appear to be *C. pneumoniae*-specific (Campos et al. (1995) Investigation of Ophthalmology and Visual Science 36:1477; Marrie (1993) Clinical Infectious Diseases. 18:501; Wiedmann-Al-Ahmad M, et al. Reactions of polyclonal and neutralizing anti-p54 monoclonal antibodies with an isolated, species-specific 54-kilodalton protein of *Chlamydia pneumoniae*. Clin Diagn Lab Immunol. November 1997; 4(6): 700-704).

Immunoblotting of isolates with sera from patients does show variation of blotting patterns between isolates, indicating that serotypes *C. pneumoniae* may exist (Grayston et al. (1995) Journal of Infectious Diseases 168:1231; Ramirez et al (1996) Annals of Internal Medicine 125:979). However, the results are potentially confounded by the infection status of the patients, since immunoblot profiles of a patient's sera change with time post-infection. An assessment of the number and relative frequency of any serotypes, and the defining antigens, is not yet possible.

Accordingly, a need exists for identifying and isolating polynucleotide sequences of *C. pneumoniae* for use in preventing and treating *Chlamydia* infection.

SUMMARY OF THE INVENTION

The present invention provides purified and isolated polynucleotide molecules that encode the *Chlamydia* polypeptide designated 76kDa protein (SEQ ID No:1) which can be used in methods to prevent, treat, and diagnose *Chlamydia* infection. In one form of the invention, the polynucleotide molecules are DNA that encode the polypeptide of SEQ ID No:2.

Another form of the invention provides polypeptides corresponding to the isolated DNA molecules. The amino acid sequence of the corresponding encoded polypeptide is shown as SEQ ID No:2.

Another form of the invention provides truncated polypeptides corresponding to truncated DNA molecules. In one embodiment, the truncated nucleotide and amino acid sequences are shown as SEQ ID Nos: 3 and 4 respectively. In another embodiment, the truncated nucleotide and amino acid sequences are shown as SEQ ID Nos: 5 and 6 respectively.

Although Melgosa et al. has reported cloning a 76kDa protein from *C. pneumoniae*, comparison of the gene sequence as reported by Melgosa et al. to the published geneome sequence of *C. pneumoniae* (http://chlamydia-www.berkeley.edu:4231/) reveals that, in fact, the genomic sequence in this region contains at least two open reading frames (ORFs), one in the 5' portion and one in the 3' portion. The sequence reported in Melgosa et al. is an in-frame fusion of the 5' end of the 5' ORF. Thus, Melgosa's deduced protein is merely a 76kDa fusion protein and not the 76kDa protein observed by immunoblotting from various *C. pneumoniae* isolates. By contrast, the 76kDa protein of the present invention is the full-length protein encoded by the 3'ORF in this region of the genome. Notably, further analysis of the genome sequence (http://chlamydia-www.berkeley.edu:4231/) reveals at least one in-frame ATG upstream of the start codon of the 5' ORF, suggesting that the 5' ORF may form part of one or more larger ORFs.

Those skilled in the art will readily understand that the invention, having provided the polynucleotide sequences encoding the *Chlamydia* 76kDa protein, also provides polynucleotides encoding fragments derived from such a polypeptide. Moreover, the invention is understood to provide mutants and derivatives of such polypeptides and fragments derived therefrom, which result from the addition, deletion, or substitution of non-essential amino acids as described herein. Those skilled in the art would also readily understand that the invention, having provided the polynucleotide sequences encoding *Chlamydia* polypeptides, further provides monospecific antibodies that specifically bind to such polypeptides.

The present invention has wide application and includes expression cassettes, vectors, and cells transformed or transfected with the polynucleotides of the invention. Accordingly, the present invention further provides (i) a method for producing a polypeptide of the invention in a recombinant host system and related expression cassettes, vectors, and transformed or transfected cells; (ii) a vaccine, or a live vaccine vector such as a pox virus, *Salmonella typhimurium*, or *Vibrio cholerae* vector, containing a polynucleotide of the invention, such vaccines and vaccine vectors being useful for, e.g., preventing and treating *Chlamydia* infection, in combination with a diluent or carrier, and related pharmaceutical compositions and associated therapeutic and/or prophylactic methods; (iii) a therapeutic and/or prophylactic use of an RNA or DNA molecule of the invention, either in a naked form or formulated with a delivery vehicle, a polypeptide or combination of polypeptides, or a monospecific antibody of the invention, and related pharmaceutical compositions; (iv) a method for diagnosing the presence of *Chlamydia* in a biological sample, which can involve the use of a DNA or RNA molecule, a monospecific antibody, or a polypeptide of the invention; and (v) a method for purifying a polypeptide of the invention by antibody-based affinity chromatography.

BRIEF DESCRIPTION OF THE DRAWINGS

The present invention will be further understood from the following description with reference to embodiments shown in the drawings, in which:

FIG. 1 shows the full-length nucleotide sequence of the 76kDa protein gene (SEQ ID No:1) and the deduced amino acid sequence of the 76kDa protein from *Chlamydia pneumoniae* (SEQ ID No:2).

FIG. 2 shows the restriction enzyme analysis of the *C. pneumoniae* 76kDa protein gene (SEQ ID No:1).

FIG. 3 shows the nucleotide sequence containing a 3'-truncated 76kDa protein gene (SEQ ID No:7) and its corresponding deduced amino acid sequence (SEQ ID No:8) from *Chlamydia pneumoniae*; (note that nucleotides 1 to 665 and 2122 to 2238 are unrelated to the 76kDa protein gene).

FIG. 7 illustrates protection against *C. pneumoniae* infection by pCACPNM555a following DNA immunization.

FIG. 8 illustrates protection against *C. pneumoniae* infection by pCAI555 following DNA immunization.

FIG. 9 illustrates protection against *C. pneumoniae* infection by pCAD76kDa following DNA immunization. For FIGS. 7 to 9, individual data points are shown for each animal (hollow diamonds) as well as mean and standard deviations for each group (solid squares).

DETAILED DESCRIPTION OF INVENTION

Figure 4:
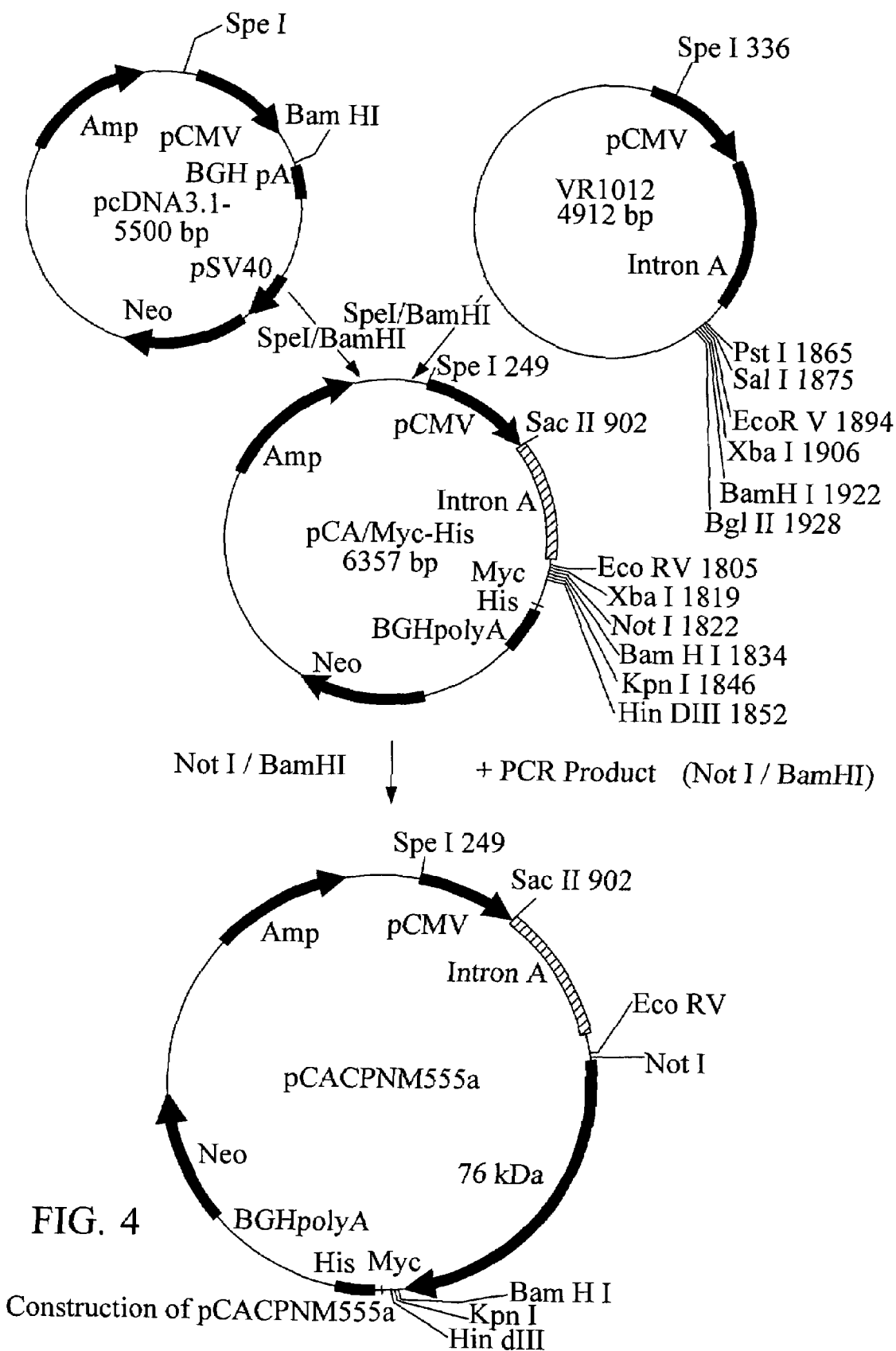
FIG. 4 shows the construction and elements of plasmid pCACPNM555a, containing the full-length 76kDa gene.

The invention is described with reference to the following sequences which are embodiments of the invention: SEQ ID NO:1 is the full-length sequence of the 76kDa protein gene.

SEQ ID NO:2 is the deduced full-length amino acid sequence of the 76kDa protein.

SEQ ID NO:3 is the 5'-truncated nucleotide sequence of the 76kDa protein gene.

SEQ ID NO:4 is the 5'-truncated amino acid sequence of the 76kDa protein.

SEQ ID NO:5 is the 3'-truncated nucleotide sequence of the 76kDa protein gene.

SEQ ID NO:6 is the 3'-truncated amino acid sequence of the 76kDa protein, which forms the basis for immunoprotection by pCAD76kDa in FIG. 9.

SEQ ID NO:7 is the sequence encoding a polypeptide containing a truncated 76kDa protein. Using this sequence as a template, a fragment was amplified by PCR to form part of construct pCAD76kDa.

SEQ ID NO:8 is the deduced amino acid sequence of a truncated 76kDa protein, as expressed from pCAD76kDa.

SEQ ID NO:9 is the 5' primer used to clone the full-length 76kDa protein gene and to amplify the full-length 76kDa protein gene for pCACPNM555a.

SEQ ID NO:10 is the 3' primer used to clone the full-length 76kDa protein gene and to amplify the full-length 76kDa protein gene for pCACPNM555a.

SEQ ID NO:11 is the 5' primer used to amplify the 5'-truncated 76kDa protein gene fragment for pCAI555.

SEQ ID NO:12 is the 3' primer used to amplify the 5'-truncated 76kDa protein gene fragment for pCAI555.

SEQ ID NO:13 is the 5' primer used to amplify the 3'-truncated 76kDa protein gene fragment for pCAD76kDa.

SEQ ID NO:14 is the 3' primer used to amplify the truncated 76kDa protein gene fragment for pCAD76kDa.

An open reading frame (ORF) encoding the Chlamydial 76kDa protein has been identified from the *C. pneumoniae* genome. The gene encoding this protein and its fragments have been inserted into expression plasmids and shown to confer immune protection against Chlamydial infection. Accordingly, this 76kDa protein and related polypeptides can be used to prevent and treat *Chlamydia* infection.

According to a first aspect of the invention, isolated polynucleotides are provided which encode *Chlamydia* polypeptides, whose amino acid sequences are shown in SEQ ID Nos: 2, 4 and 6.

The term "isolated polynucleotide" is defined as a polynucleotide removed from the environment in which it naturally occurs. For example, a naturally-occurring DNA molecule present in the genome of a living bacteria or as part of a gene bank is not isolated, but the same molecule separated from the remaining part of the bacterial genome, as a result of, e.g., a cloning event (amplification), is isolated. Typically, an isolated DNA molecule is free from DNA regions (e.g., coding regions) with which it is immediately contiguous at the 5' or 3' end, in the naturally occurring genome. Such isolated polynucleotides may be part of a vector or a composition and still be defined as isolated in that such a vector or composition is not part of the natural environment of such polynucleotide.

The polynucleotide of the invention is either RNA or DNA (cDNA, genomic DNA, or synthetic DNA), or modifications, variants, homologs or fragments thereof. The DNA is either double-stranded or single-stranded, and, if single-stranded, is either the coding strand or the non-coding (anti-sense) strand. Any one of the sequences that encode the polypeptides of the invention as shown in SEQ ID No:1, 3 or 5 is (a) a coding sequence, (b) a ribonucleotide sequence derived from transcription of (a), or (c) a coding sequence which uses the redundancy or degeneracy of the genetic code to encode the same polypeptides. By "polypeptide" or "protein" is meant any chain of amino acids, regardless of length or post-translational modification (e.g., glycosylation or phosphorylation). Both terms are used interchangeably in the present application.

Consistent with the first aspect of the invention, amino acid sequences are provided which are homologous to SEQ ID No:2, 4 or 6. As used herein, "homologous amino acid sequence" is any polypeptide which is encoded, in whole or in part, by a nucleic acid sequence which hybridizes at 25-35° C. below critical melting temperature (Tm), to any portion of the nucleic acid sequence of SEQ ID No:1, 3 or 5. A homologous amino acid sequence is one that differs from an amino acid sequence shown in SEQ ID No:2, 4 or 6 by one or more conservative amino acid substitutions. Such a sequence also encompass serotypic variants (defined below) as well as sequences containing deletions or insertions which retain inherent characteristics of the polypeptide such as immunogenicity. Preferably, such a sequence is at least 75%, more preferably 80%, and most preferably 90% identical to SEQ ID No:2, 4 or 6.

Homologous amino acid sequences include sequences that are identical or substantially identical to SEQ ID No:2, 4 or 6. By "amino acid sequence substantially identical" is meant a sequence that is at least 90%, preferably 95%, more preferably 97%, and most preferably 99% identical to an amino acid sequence of reference and that preferably differs from the sequence of reference by a majority of conservative amino acid substitutions.

Conservative amino acid substitutions are substitutions among amino acids of the same class. These classes include, for example, amino acids having uncharged polar side chains, such as asparagine, glutamine, serine, threonine, and tyrosine; amino acids having basic side chains, such as lysine, arginine, and histidine; amino acids having acidic side chains, such as aspartic acid and glutamic acid; and amino acids having nonpolar side chains, such as glycine, alanine, valine, leucine, isoleucine, proline, phenylalanine, methionine, tryptophan, and cysteine.

Homology is measured using sequence analysis software such as Sequence Analysis Software Package of the Genetics Computer Group, University of Wisconsin Biotechnology Center, 1710 University Avenue, Madison, Wis. 53705. Amino acid sequences are aligned to maximize identity. Gaps may be artificially introduced into the sequence to attain proper alignment. Once the optimal alignment has been set up, the degree of homology is established by recording all of the positions in which the amino acids of both sequences are identical, relative to the total number of positions.

Homologous polynucleotide sequences are defined in a similar way. Preferably, a homologous sequence is one that is at least 45%, more preferably 60%, and most preferably 85% identical to the coding sequence of SEQ ID No:1, 3 or 5.

Consistent with the first aspect of the invention, polypeptides having a sequence homologous to SEQ ID No:2, 4 or 6 include naturally-occurring allelic variants, as well as mutants or any other non-naturally occurring variants that retain the inherent characteristics of the polypeptide of SEQ ID No:2, 4 or 6.

As is known in the art, an allelic variant is an alternate form of a polypeptide that is characterized as having a substitution, deletion, or addition of one or more amino acids that does not alter the biological function of the polypeptide. By "biological function" is meant the function of the polypeptide in the cells in which it naturally occurs, even if the function is not necessary for the growth or survival of the cells. For example, the biological function of a porin is to allow the entry into cells of compounds present in the extracellular medium. Biological function is distinct from antigenic property. A polypeptide can have more than one biological function.

Allelic variants are very common in nature. For example, a bacterial species such as *C. pneumoniae*, is usually represented by a variety of strains that differ from each other by minor allelic variations. Indeed, a polypeptide that fulfills the same biological function in different strains can have an amino acid sequence (and polynucleotide sequence) that is not identical in each of the strains. Despite this variation, an immune response directed generally against many allelic variants has been demonstrated. In studies of the Chlamydial MOMP antigen, cross-strain antibody binding plus neutralization of infectivity occurs despite amino acid sequence variation of MOMP from strain to strain, indicating that the MOMP, when used as an immunogen, is tolerant of amino acid variations.

Polynucleotides encoding homologous polypeptides or allelic variants are retrieved by polymerase chain reaction (PCR) amplification of genomic bacterial DNA extracted by conventional methods. This involves the use of synthetic oligonucleotide primers matching upstream and downstream of the 5' and 3' ends of the encoding domain. Suitable primers are designed according to the nucleotide sequence information provided in SEQ ID No:1, 3 or 5. The procedure is as follows: a primer is selected which consists of 10 to 40, preferably 15 to 25 nucleotides. It is advantageous to select primers containing C and G nucleotides in a proportion sufficient to ensure efficient hybridization; i.e., an amount of C and G nucleotides of at least 40%, preferably 50% of the total nucleotide content. A standard PCR reaction contains typically 0.5 to 5 Units of Taq DNA polymerase per 100 µL, 20 to 200 µM deoxynucleotide each, preferably at equivalent concentrations, 0.5 to 2.5 mM magnesium over the total deoxynucleotide concentration, $10^5$ to $10^6$ target molecules, and about 20 pmol of each primer. About 25 to 50 PCR cycles are performed, with an annealing temperature 15° C. to 5° C. below the true Tm of the primers. A more stringent annealing temperature improves discrimination against incorrectly annealed primers and reduces incorporation of incorrect nucleotides at the 3' end of primers. A denaturation temperature of 95° C. to 97° C. is typical, although higher temperatures may be appropriate for dematuration of G+C-rich targets. The number of cycles performed depends on the starting concentration of target molecules, though typically more than 40 cycles is not recommended as non-specific background products tend to accumulate.

An alternative method for retrieving polynucleotides encoding homologous polypeptides or allelic variants is by hybridization screening of a DNA or RNA library. Hybridization procedures are well-known in the art and are described in Ausubel et al., (Ausubel et al., Current Protocols in Molecular Biology, John Wiley & Sons Inc., 1994), Silhavy et al. (Silhavy et al. Experiments with Gene Fusions, Cold Spring Harbor Laboratory Press, 1984), and Davis et al. (Davis et al. A Manual for Genetic Engineering: Advanced Bacterial Genetics, Cold Spring Harbor Laboratory Press, 1980)). Important parameters for optimizing hybridization conditions are reflected in a formula used to obtain the critical melting temperature above which two complementary DNA strands separate from each other (Casey & Davidson, Nucl. Acid Res. (1977) 4:1539). For polynucleotides of about 600 nucleotides or larger, this formula is as follows: Tm=81.5+ 0.41×(% G+C)+16.6 log(cation ion concentration)−0.63×(% formamide)−600/base number. Under appropriate stringency conditions, hybridization temperature (Th) is approximately 20 to 40° C., 20 to 25° C., or, preferably 30 to 40° C. below the calculated Tm. Those skilled in the art will understand that optimal temperature and salt conditions can be readily determined.

For the polynucleotides of the invention, stringent conditions are achieved for both pre-hybridizing and hybridizing incubations (i) within 4-16 hours at 42° C., in 6 ×SSC containing 50% formamide, or (ii) within 4-16 hours at 65° C. in an aqueous 6×SSC solution (1 M NaCl, 0.1 M sodium citrate (pH 7.0)). Typically, hybridization experiments are performed at a temperature from 60 to 68° C., e.g. 65° C. At such a temperature, stringent hybridization conditions can be achieved in 6×SSC, preferably in 2×SSC or 1×SSC, more preferably in 0.5×SSc, 0.3×SSC or 0.1×SSC (in the absence of formamide). 1×SSC contains 0.15 M NaCl and 0.015 M sodium citrate.

Useful homologs and fragments thereof that do not occur naturally are designed using known methods for identifying regions of an antigen that are likely to tolerate amino acid sequence changes and/or deletions. As an example, homologous polypeptides from different species are compared; conserved sequences are identified. The more divergent sequences are the most likely to tolerate sequence changes. Homology among sequences may be analyzed using, as an example, the BLAST homology searching algorithm of Altschul et al., Nucleic Acids Res.; 25:3389-3402 (1997). Alternatively, sequences are modified such that they become more reactive to T- and/or B-cells, based on computer-assisted analysis of probable T- or B-cell epitopes Yet another alternative is to mutate a particular amino acid residue or sequence within the polypeptide in vitro, then screen the mutant polypeptides for their ability-to prevent or treat *Chlamydia* infection according to the method outlined below.

A person skilled in the art will readily understand that by following the screening process of this invention, it will be determined without undue experimentation whether a particular homolog of SEQ ID No:2, 4 or 6 may be useful in the prevention or treatment of *Chlamydia* infection. The screening procedure comprises the steps:

(i) immunizing an animal, preferably mouse, with the test homolog or fragment;

(ii) inoculating the immunized animal with *Chlamydia*; and (iii) selecting those homologs or fragments which confer protection against *Chlamydia*.

By "conferring protection" is meant that there is a reduction in severity of any of the effects of *Chlamydia* infection, in comparison with a control animal which was not immunized with the test homolog or fragment.

Consistent with the first aspect of the invention, polypeptide derivatives are provided that are partial sequences of SEQ ID No:2, 4 or 6, partial sequences of polypeptide sequences homologous to SEQ ID No:2, 4 or 6, polypeptides derived from full-length polypeptides by internal deletion, and fusion proteins.

It is an accepted practice in the field of immunology to use fragments and variants of protein immunogens as vaccines, as all that is required to induce an immune response to a protein is a small (e.g., 8 to 10 amino acid) immunogenic region of the protein. Various short synthetic peptides corresponding to surface-exposed antigens of pathogens other than *Chlamydia* have been shown to be effective vaccine antigens against their respective pathogens, e.g. an 11 residue peptide of murine mammary tumor virus (Casey & Davidson, Nucl. Acid Res. (1977) 4:1539), a 16-residue peptide of Semliki Forest virus (Snijders et al., 1991. J. Gen. Virol. 72:557-565), and two overlapping peptides of 15 residues each from canine parvovirus (Langeveld et al., Vaccine 12(15):1473-1480, 1994).

Accordingly, it will be readily apparent to one skilled in the art, having read the present description, that partial sequences of SEQ ID No:2, 4 or 6 or their homologous amino acid sequences are inherent to the full-length sequences and are taught by the present invention. Such polypeptide fragments preferably are at least 12 amino acids in length. Advantageously, they are at least 20 amino acids, preferably at least 50 amino acids, and more preferably at least 75 amino acids and most preferably at least 100 amino acids in length.

Polynucleotides of 30 to 600 nucleotides encoding partial sequences of sequences homologous to SEQ ID No:2, 4 or 6 are retrieved by PCR amplification using the parameters outlined above and using primers matching the sequences upstream and downstream of the 5' and 3' ends of the fragment to be amplified. The template polynucleotide for such amplification is either the full length polynucleotide homologous to SEQ ID No:1, 3 or 5, or a polynucleotide contained in a mixture of polynucleotides such as a DNA or RNA library. As an alternative method for retrieving the partial sequences, screening hybridization is carried out under conditions described above and using the formula for calculating Tm. Where fragments of 30 to 600 nucleotides are to be retrieved, the calculated Tm is corrected by subtracting (600/polynucleotide size in base pairs) and the stringency conditions are defined by a hybridization temperature that is 5 to 10° C. below Tm. Where oligonucleotides shorter than 20-30 bases are to be obtained, the formula for calculating the Tm is as follows: Tm=4×(G+C)+2 (A+T). For example, an 18 nucleotide fragment of 50% G+C would have an approximate Tm of 54° C. Short peptides that are fragments of SEQ ID No:2, 4 or 6 or its homologous sequences, are obtained directly by chemical synthesis (E. Gross and H. J. Meinhofer, 4 The Peptides: Analysis, Synthesis, Biology; Modern Techniques of Peptide Synthesis, John Wiley & Sons (1981), and M. Bodanzki, Principles of Peptide Synthesis, Springer-Verlag (1984)).

Useful polypeptide derivatives, e.g., polypeptide fragments, are designed using computer-assisted analysis of amino acid sequences. This would identify probable surface-exposed, antigenic regions (Hughes et al., 1992. Infect. Immun. 60(9):3497). Analysis of 6 amino acid sequences contained in SEQ ID No:2, 4 or 6, based on the product of flexibility and hydrophobicity propensities using the program SEQSEE (Wishart D S, et al. "SEQSEE: a comprehensive program suite for protein sequence analysis." *Comput Appl Biosci*. April 1994;10(2):121-32), can reveal potential B- and T-cell epitopes which may be used as a basis for selecting useful immunogenic fragments and variants. This analysis uses a reasonable combination of external surface features that is likely to be recognized by antibodies. Probable T-cell epitopes for HLA-A0201 MHC subclass may be revealed by an algorithms that emulate an approach developed at the NIH (Parker K C, et al. "Peptide binding to MHC class I molecules: implications for antigenic peptide prediction." *Immunol Res* 1995;14(1):34-57).

Epitopes which induce a protective T cell-dependent immune response are present throughout the length of the polypeptide. However, some epitopes may be masked by secondary and tertiary structures of the polypeptide. To reveal such masked epitopes large internal deletions are created which remove much of the original protein structure and exposes the masked epitopes. Such internal deletions sometimes effect the additional advantage of removing immunodominant regions of high variability among strains.

Polynucleotides encoding polypeptide fragments and polypeptides having large internal deletions are constructed using standard methods (Ausubel et al., Current Protocols in Molecular Biology, John Wiley & Sons Inc., 1994). Such methods include standard PCR, inverse PCR, restriction enzyme treatment of cloned DNA molecules, or the method of Kunkel et al. (Kunkel et al. Proc. Natl. Acad. Sci. USA (1985) 82:448). Components for these methods and instructions for their use are readily available from various commercial sources such as Stratagene. Once the deletion mutants have been constructed, they are tested for their ability to prevent or treat *Chlamydia* infection as described above.

As used herein, a fusion polypeptide is one that contains a polypeptide or a polypeptide derivative of the invention fused at the N- or C-terminal end to any other polypeptide (hereinafter referred to as a peptide tail). A simple way to obtain such a fusion polypeptide is by translation of an in-frame fusion of the polynucleotide sequences, i.e., a hybrid gene. The hybrid gene encoding the fusion polypeptide is inserted into an expression vector which is used to transform or transfect a host cell. Alternatively, the polynucleotide sequence encoding the polypeptide or polypeptide derivative is inserted into an expression vector in which the polynucleotide encoding the peptide tail is already present. Such vectors and instructions for their use are commercially available, e.g. the pMal-c2 or pMal-p2 system from New England Biolabs, in which the peptide tail is a maltose binding protein, the glutathione-S-transferase system of Pharmacia, or the His-Tag system available from Novagen. These and other expression systems provide convenient means for further purification of polypeptides and derivatives of the invention.

An advantageous example of a fusion polypeptide is one where the polypeptide or homolog or fragment of the invention is fused to a polypeptide having adjuvant activity, such as subunit B of either cholera toxin or *E. coli* heat-labile toxin. Another advantageous fusion is one where the polypeptide, homolog or fragment is fused to a strong T-cell epitope or B-cell epitope. Such an epitope may be one known in the art (e.g. the Hepatitis B virus core antigen, D. R. Millich et al., "Antibody production to the nucleocapsid and envelope of the Hepatitis B virus primed by a single synthetic T cell site", Nature. 1987. 329:547-549), or one which has been identified in another polypeptide of the invention based on computer-assisted analysis of probable T- or B-cell epitopes. Consistent with this aspect of the invention is a fusion polypeptide comprising T- or B-cell epitopes from SEQ ID No:2, 4 or 6 or its homolog or fragment, wherein the epitopes are derived from multiple variants of said polypeptide or homolog or fragment, each variant differing from another in the location and sequence of its epitope within the polypeptide. Such a fusion is effective in the prevention and treatment of *Chlamydia* infection since it optimizes the T- and B-cell response to the overall polypeptide, homolog or fragment.

To effect fusion, the polypeptide of the invention is fused to the N-, or preferably, to the C-terminal end of the polypeptide having adjuvant activity or T- or B-cell epitope. Alternatively, a polypeptide fragment of the invention is inserted internally within the amino acid sequence of the polypeptide having adjuvant activity. The T- or B-cell epitope may also be inserted internally within the amino acid sequence of the polypeptide of the invention.

Consistent with the first aspect, the polynucleotides of the invention also encode hybrid precursor polypeptides containing heterologous signal peptides, which mature into polypeptides of the invention. By "heterologous signal peptide" is meant a signal peptide that is not found in naturally-occurring precursors of polypeptides of the invention.

Polynucleotide molecules according to the invention, including RNA, DNA, or modifications or combinations thereof, have various applications. A DNA molecule is used, for example, (i) in a process for producing the encoded polypeptide in a recombinant host system, (ii) in the construction of vaccine vectors such as poxviruses, which are further used in methods and compositions for preventing and/or treating *Chlamydia* infection, (iii) as a vaccine agent (as well as an RNA molecule), in a naked form or formulated with a delivery vehicle and, (iv) in the construction of attenuated *Chlamydia* strains that can over-express a polynucleotide of the invention or express it in a non-toxic, mutated form.

Accordingly, a second aspect of the invention encompasses (i) an expression cassette containing a DNA molecule of the invention placed under the control of the elements required for expression, in particular under the control of an appropriate promoter; (ii) an expression vector containing an expression cassette of the invention; (iii) a procaryotic or eucaryotic cell transformed or transfected with an expression cassette and/or vector of the invention, as well as (iv) a process for producing a polypeptide or polypeptide derivative encoded by a polynucleotide of the invention, which involves culturing a procaryotic or eucaryotic cell transformed or transfected with an expression cassette and/or vector of the invention, under conditions that allow expression of the DNA molecule of the invention and, recovering the encoded polypeptide or polypeptide derivative from the cell culture.

A recombinant expression system is selected from procaryotic and eucaryotic hosts. Eucaryotic hosts include yeast cells (e.g., *Saccharomyces cerevisiae* or *Pichia pastoris*), mammalian cells (e.g., COS1, NIH3T3, or JEG3 cells), arthropods cells (e.g., *Spodoptera frugiperda* (SF9) cells), and plant cells. A preferred expression system is a procaryotic host such as *E. coli*. Bacterial and eucaryotic cells are available from a number of different sources including commercial sources to those skilled in the art, e.g., the American Type Culture Collection (ATCC; Rockville, Md.). Commercial sources of cells used for recombinant protein expression also provide instructions for usage of the cells.

The choice of the expression system depends on the features desired for the expressed polypeptide. For example, it may be useful to produce a polypeptide of the invention in a particular lipidated form or any other form.

One skilled in the art would readily understand that not all vectors and expression control sequences and hosts would be expected to express equally well the polynucleotides of this invention. With the guidelines described below, however, a selection of vectors, expression control sequences and hosts may be made without undue experimentation and without departing from the scope of this invention.

In selecting a vector, the host must be chosen that is compatible with the vector which is to exist and possibly replicate in it. Considerations are made with respect to the vector copy number, the ability to control the copy number, expression of other proteins such as antibiotic resistance. In selecting an expression control sequence, a number of variables are considered. Among the important variable are the relative strength of the sequence (e.g. the ability to drive expression under various conditions), the ability to control the sequence's function, compatibility between the polynucleotide to be expressed and the control sequence (e.g. secondary structures are considered to avoid hairpin structures which prevent efficient transcription). In selecting the host, unicellular hosts are selected which are compatible with the selected vector, tolerant of any possible toxic effects of the expressed product, able to secrete the expressed product efficiently if such is desired, to be able to express the product in the desired conformation, to be easily scaled up, and to which ease of purification of the final product.

The choice of the expression cassette depends on the host system selected as well as the features desired for the expressed polypeptide. Typically, an expression cassette includes a promoter that is functional in the selected host system and can be constitutive or inducible; a ribosome binding site; a start codon (ATG) if necessary; a region encoding a signal peptide, e.g., a lipidation signal peptide; a DNA molecule of the invention; a stop codon; and optionally a 3' terminal region (translation and/or transcription terminator). The signal peptide encoding region is adjacent to the polynucleotide of the invention and placed in proper reading frame. The signal peptide-encoding region is homologous or heterologous to the DNA molecule encoding the mature polypeptide and is compatible with the secretion apparatus of the host used for expression. The open reading frame constituted by the DNA molecule of the invention, solely or together with the signal peptide, is placed under the control of the promoter so that transcription and translation occur in the host system. Promoters and signal peptide encoding regions are widely known and available to those skilled in the art and include, for example, the promoter of *Salmonella typhimurium* (and derivatives) that is inducible by arabinose (promoter araB) and is functional in Gram-negative bacteria such as *E. coli* (as described in U.S. Pat. No. 5,028,530 and in Cagnon et al., (Cagnon et al., Protein Engineering (1991) 4(7):843)); the promoter of the gene of bacteriophage T7 encoding RNA polymerase, that is functional in a number of *E. coli* strains expressing T7 polymerase (described in U.S. Pat. No. 4,952,496); OspA lipidation signal peptide ; and RlpB lipidation signal peptide (Takase et al., J. Bact. (1987) 169:5692).

The expression cassette is typically part of an expression vector, which is selected for its ability to replicate in the chosen expression system. Expression vectors (e.g., plasmids or viral vectors) can be chosen, for example, from those described in Pouwels et al. (Cloning Vectors: A Laboratory Manual 1985, Supp. 1987). Suitable expression vectors can be purchased from various commercial sources.

Methods for transforming/transfecting host cells with expression vectors are well-known in the art and depend on the host system selected as described in Ausubel et al., (Ausubel et al., Current Protocols in Molecular Biology, John Wiley & Sons Inc., 1994).

Upon expression, a recombinant polypeptide of the invention (or a polypeptide derivative) is produced and remains in the intracellular compartment, is secreted/excreted in the extracellular medium or in the periplasmic space, or is embedded in the cellular membrane. The polypeptide is recovered in a substantially purified form from the cell extract or from the supernatant after centrifugation of the recombinant cell culture. Typically, the recombinant polypeptide is purified by antibody-based affinity purification or by other well-known methods that can be readily adapted by a person skilled in the art, such as fusion of the polynucleotide encoding the polypeptide or its derivative to a small affinity binding domain. Antibodies useful for purifying by immunoaffinity the polypeptides of the invention are obtained as described below.

A polynucleotide of the invention can also be useful as a vaccine. There are two major routes, either using a viral or bacterial host as gene delivery vehicle (live vaccine vector) or administering the gene in a free form, e.g., inserted into a plasmid. Therapeutic or prophylactic efficacy of a polynucleotide of the invention is evaluated as described below.

Accordingly, a third aspect of the invention provides (i) a vaccine vector such as a poxvirus, containing a DNA molecule of the invention, placed under the control of elements required for expression; (ii) a composition of matter comprising a vaccine vector of the invention, together with a diluent or carrier; specifically (iii) a pharmaceutical composition containing a therapeutically or prophylactically effective amount of a vaccine vector of the invention; (iv) a method for inducing an immune response against *Chlamydia* in a mammal (e.g., a human; alternatively, the method can be used in veterinary applications for treating or preventing *Chlamydia* infection of animals, e.g., cats or birds), which involves administering to the mammal an immunogenically effective amount of a vaccine vector of the invention to elicit a protective or therapeutic immune response to *Chlamydia*; and particularly, (v) a method for preventing and/or treating a *Chlamydia* (e.g., *C. trachomatis, C. psittaci, C. pneumonia, C. pecorum*) infection, which involves administering a prophylactic or therapeutic amount of a vaccine vector of the invention to an infected individual. Additionally, the third aspect of the invention encompasses the use of a vaccine vector of the invention in the preparation of a medicament for preventing and/or treating *Chlamydia* infection.

As used herein, a vaccine vector expresses one or several polypeptides or derivatives of the invention. The vaccine vector may express additionally a cytokine, such as interleukin-2 (IL-2) or interleukin-12 (IL-12), that enhances the immune response (adjuvant effect). It is understood that each of the components to be expressed is placed under the control of elements required for expression in a mammalian cell.

Consistent with the third aspect of the invention is a composition comprising several vaccine vectors, each of them capable of expressing a polypeptide or derivative of the invention. A composition may also comprise a vaccine vector capable of expressing an additional *Chlamydia* antigen, or a subunit, fragment, homolog, mutant, or derivative thereof; optionally together with or a cytokine such as IL-2 or IL-12.

Vaccination methods for treating or preventing infection in a mammal comprises use of a vaccine vector of the invention to be administered by any conventional route, particularly to a mucosal (e.g., ocular, intranasal, oral, gastric, pulmonary, intestinal, rectal, vaginal, or urinary tract) surface or via the parenteral (e.g., subcutaneous, intradermal, intramuscular, intravenous, or intraperitoneal) route. Preferred routes depend upon the choice of the vaccine vector. Treatment may be effected in a single dose or repeated at intervals. The appropriate dosage depends on various parameters understood by skilled artisans such as the vaccine vector itself, the route of administration or the condition of the mammal to be vaccinated (weight, age and the like).

Live vaccine vectors available in the art include viral vectors such as adenoviruses and poxviruses as well as bacterial vectors, e.g., *Shigella, Salmonella, Vibrio cholerae, Lactobacillus*, Bacille bilié de Calmette-Guérin (BCG), and *Streptococcus*.

An example of an adenovirus vector, as well as a method for constructing an adenovirus vector capable of expressing a DNA molecule of the invention, are described in U.S. Pat. No. 4,920,209. Poxvirus vectors include vaccinia and canary pox virus, described in U.S. Pat. No. 4,722,848 and U.S. Pat. No. 5,364,773, respectively. (Also see, e.g., Tartaglia et al., Virology (1992) 188:217) for a description of a vaccinia virus vector and Taylor et al, Vaccine (1995) 13:539 for a reference of a canary pox.) Poxvirus vectors capable of expressing a polynucleotide of the invention are obtained by homologous recombination as described in Kieny et al., Nature (1984) 312:163 so that the polynucleotide of the invention is inserted in the viral genome under appropriate conditions for expression in mammalian cells. Generally, the dose of vaccine viral vector, for therapeutic or prophylactic use, can be of from about $1\times10^4$ to about $1\times10^{11}$, advantageously from about $1\times10^7$ to about $1\times10^{10}$, preferably of from about $1\times10^7$ to about $1\times10^9$ plaque-forming units per kilogram. Preferably, viral vectors are administered parenterally; for example, in 3 doses, 4 weeks apart. It is preferable to avoid adding a chemical adjuvant to a composition containing a viral vector of the invention and thereby minimizing the immune response to the viral vector itself.

Non-toxicogenic *Vibrio cholerae* mutant strains that are useful as a live oral vaccine are known. Mekalanos et al., Nature (1983) 306:551 and U.S. Pat. No. 4,882,278 describe strains which have a substantial amount of the coding sequence of each of the two ctxA alleles deleted so that no functional cholera toxin is produced. WO 92/11354 describes a strain in which the irgA locus is inactivated by mutation; this mutation can be combined in a single strain with ctxA mutations. WO 94/01533 describes a deletion mutant lacking functional ctxA and attRS1 DNA sequences. These mutant strains are genetically engineered to express heterologous antigens, as described in WO 94/19482. An effective vaccine dose of a *Vibrio cholerae* strain capable of expressing a polypeptide or polypeptide derivative encoded by a DNA molecule of the invention contains about $1\times10^5$ to about $1\times10^9$, preferably about $1\times10^6$ to about $1\times10^8$, viable bacteria in a volume appropriate for the selected route of administration. Preferred routes of administration include all mucosal routes; most preferably, these vectors are administered intranasally or orally.

Attenuated *Salmonella typhimurium* strains, genetically engineered for recombinant expression of heterologous antigens or not, and their use as oral vaccines are described in Nakayama et al. (Bio/Technology (1988) 6:693) and WO 92/11361. Preferred routes of administration include all mucosal routes; most preferably, these vectors are administered intranasally or orally.

Other bacterial strains used as vaccine vectors in the context of the present invention are described for *Shigella flexneri* in High et al., EMBO (1992) 11:1991 and Sizemore et al., Science (1995) 270:299; for *Streptococcus gordonii* in Medaglini et al., Proc. Natl. Acad. Sci. USA (1995) 92:6868; and for Bacille Calmette Guerin in Flynn J. L., Cell. Mol. Biol. (1994) 40 (suppl. I):31, WO 88/06626, WO 90/00594, WO 91/13157, WO 92/01796, and WO 92/21376.

In bacterial vectors, the polynucleotide of the invention is inserted into the bacterial genome or remains in a free state as part of a plasmid.

The composition comprising a vaccine bacterial vector of the present invention may further contain an adjuvant. A number of adjuvants are known to those skilled in the art. Preferred adjuvants are selected as provided below.

Accordingly, a fourth aspect of the invention provides (i) a composition of matter comprising a polynucleotide of the invention, together with a diluent or carrier; (ii) a pharmaceutical composition comprising a therapeutically or prophylactically effective amount of a polynucleotide of the invention; (iii) a method for inducing an immune response against *Chlamydia* in a mammal by administration of an immunogenically effective amount of a polynucleotide of the invention to elicit a protective immune response to *Chlamydia*; and particularly, (iv) a method for preventing and/or treating a *Chlamydia* (e.g., *C. trachomatis, C. psittaci, C. pneumoniae*, or *C. pecorum*) infection, by administering a prophylactic or therapeutic amount of a polynucleotide of the invention to an infected individual. Additionally, the fourth aspect of the invention encompasses the use of a polynucleotide of the invention in the preparation of a medicament for preventing and/or treating *Chlamydia* infection. A preferred use includes the use of a DNA molecule placed under conditions for expression in a mammalian cell, especially in a plasmid that is unable to replicate in mammalian cells and to substantially integrate in a mammalian genome.

Use of the polynucleotides of the invention include their administration to a mammal as a vaccine, for therapeutic or prophylactic purposes. Such polynucleotides are used in the form of DNA as part of a plasmid that is unable to replicate in a mammalian cell and unable to integrate into the mammalian genome. Typically, such a DNA molecule is placed under the control of a promoter suitable for expression in a mammalian cell. The promoter functions either ubiquitously or tissue-specifically. Examples of non-tissue specific promoters include the early Cytomegalovirus (CMV) promoter (described in U.S. Pat. No. 4,168,062) and the Rous Sarcoma Virus promoter (described in Norton & Coffin, Molec. Cell Biol. (1985) 5:281). An example of a tissue-specific promoter is the desmin promoter which drives expression in muscle cells (Li et al., Gene (1989) 78:243, Li & Paulin, J. Biol. Chem. (1991) 266:6562 and Li & Paulin, J. Biol. Chem. (1993) 268:10403). Use of promoters is well-known to those skilled in the art. Useful vectors are described in numerous publications, specifically WO 94/21797 and Hartikka et al., Human Gene Therapy (1996) 7:1205.

Polynucleotides of the invention which are used as vaccines encode either a precursor or a mature form of the corresponding polypeptide. In the precursor form, the signal peptide is either homologous or heterologous. In the latter case, a eucaryotic leader sequence such as the leader sequence of the tissue-type plasminogen factor (tPA) is preferred.

As used herein, a composition of the invention contains one or several polynucleotides with optionally at least one additional polynucleotide encoding another *Chlamydia* antigen such as urease subunit A, B, or both, or a fragment, derivative, mutant, or analog thereof. The composition may also contain an additional polynucleotide encoding a cytokine, such as interleukin-2 (IL-2) or interleukin-12 (IL-12) so that the immune response is enhanced. These additional polynucleotides are placed under appropriate control for expression. Advantageously, DNA molecules of the invention and/or additional DNA molecules to be included in the same composition, are present in the same plasmid.

Standard techniques of molecular biology for preparing and purifying polynucleotides are used in the preparation of polynucleotide therapeutics of the invention. For use as a vaccine, a polynucleotide of the invention is formulated according to various methods outlined below.

One method utililizes the polynucleotide in a naked form, free of any delivery vehicles. Such a polynucleotide is simply diluted in a physiologically acceptable solution such as sterile saline or sterile buffered saline, with or without a carrier. When present, the carrier preferably is isotonic, hypotonic, or weakly hypertonic, and has a relatively low ionic strength, such as provided by a sucrose solution, e.g., a solution containing 20% sucrose.

An alternative method utilizes the polynucleotide in association with agents that assist in cellular uptake. Examples of such agents are (i) chemicals that modify cellular permeability, such as bupivacaine (see, e.g., WO 94/16737), (ii) liposomes for encapsulation of the polynucleotide, or (iii) cationic lipids or silica, gold, or tungsten microparticles which associate themselves with the polynucleotides.

Anionic and neutral liposomes are well-known in the art (see, e.g., Liposomes: A Practical Approach, RPC New Ed, IRL press (1990), for a detailed description of methods for making liposomes) and are useful for delivering a large range of products, including polynucleotides.

Cationic lipids are also known in the art and are commonly used for gene delivery. Such lipids include Lipofectin™ also known as DOTMA (N-[1-(2,3-dioleyloxy)propyl]-N,N,N-trimethylammonium chloride), DOTAP (1,2-bis(oleyloxy)-3-(trimethylammonio)propane), DDAB (dimethyldioctadecylammonium bromide), DOGS (dioctadecylamidologlycyl spermine) and cholesterol derivatives such as DC-Chol (3 beta-(N-(N',N'-dimethyl aminomethane)-carbamoyl) cholesterol). A description of these cationic lipids can be found in EP 187,702, WO 90/11092, U.S. Pat. No. 5,283,185, WO 91/15501, WO 95/26356, and U.S. Pat. No. 5,527,928. Cationic lipids for gene delivery are preferably used in association with a neutral lipid such as DOPE (dioleyl phosphatidylethanolamine), as described in WO 90/11092 as an example.

Formulation containing cationic liposomes may optionally contain other transfection-facilitating compounds. A number of them are described in WO 93/18759, WO 93/19768, WO 94/25608, and WO 95/02397. They include spermine derivatives useful for facilitating the transport of DNA through the nuclear membrane (see, for example, WO 93/18759) and membrane-permeabilizing compounds such as GALA, Gramicidine S, and cationic bile salts (see, for example, WO 93/19768).

Gold or tungsten microparticles are used for gene delivery, as described in WO 91/00359, WO 93/17706, and Tang et al. Nature (1992) 356:152. The microparticle-coated polynucleotide is injected via intradermal or intraepidermal routes using a needleless injection device ("gene gun"), such as those described in U.S. Pat. No. 4,945,050, U.S. Pat. No. 5,015,580, and WO 94/24263.

The amount of DNA to be used in a vaccine recipient depends, e.g., on the strength of the promoter used in the DNA construct, the immunogenicity of the expressed gene product, the condition of the mammal intended for administration (e.g., the weight, age, and general health of the mammal), the mode of administration, and the type of formulation. In general, a therapeutically or prophylactically effective dose from about 1 µg to about 1 mg, preferably, from about 10 µg to about 800 µg and, more preferably, from about 25 µg to about 250 µg, can be administered to human adults. The administration can be achieved in a single dose or repeated at intervals.

The route of administration is any conventional route used in the vaccine field. As general guidance, a polynucleotide of the invention is administered via a mucosal surface, e.g., an ocular, intranasal, pulmonary, oral, intestinal, rectal, vaginal, and urinary tract surface; or via a parenteral route, e.g., by an intravenous, subcutaneous, intraperitoneal, intradermal, intraepidermal, or intramuscular route. The choice of administration route depends on the formulation that is selected. A polynucleotide formulated in association with bupivacaine is advantageously administered into muscles. When a neutral or anionic liposome or a cationic lipid, such as DOTMA or DC-Chol, is used, the formulation can be advantageously injected via intravenous, intranasal (aerosolization), intramuscular, intradermal, and subcutaneous routes. A polynucleotide in a naked form can advantageously be administered via the intramuscular, intradermal, or subcutaneous routes.

Although not absolutely required, such a composition can also contain an adjuvant. If so, a systemic adjuvant that does not require concomitant administration in order to exhibit an adjuvant effect is preferable such as, e.g., QS21, which is described in U.S. Pat. No. 5,057,546.

The sequence information provided in the present application enables the design of specific nucleotide probes and primers that are used for diagnostic purposes. Accordingly, a fifth aspect of the invention provides a nucleotide probe or primer having a sequence found in or derived by degeneracy of the genetic code from a sequence shown in SEQ ID No:1, 3 or 5

The term "probe" as used in the present application refers to DNA (preferably single stranded) or RNA molecules (or modifications or combinations thereof) that hybridize under the stringent conditions, as defined above, to nucleic acid molecules having SEQ ID No:1, 3 or 5 or to sequences homologous to SEQ ID No:1, 3 or 5, or to its complementary or anti-sense sequence. Generally, probes are significantly shorter than full-length sequences. Such probes contain from about 5 to about 100, preferably from about 10 to about 80, nucleotides. In particular, probes have sequences that are at least 75%, preferably at least 85%, more preferably 95% homologous to a portion of SEQ ID No:1, 3 or 5 or that are complementary to such sequences. Probes may contain modified bases such as inosine, methyl-5-deoxycytidine, deoxyuridine, dimethylamino-5-deoxyuridine, or diamino-2,6-purine. Sugar or phosphate residues may also be modified or substituted. For example, a deoxyribose residue may be replaced by a polyamide (Nielsen et al., Science (1991) 254: 1497) and phosphate residues may be replaced by ester groups such as diphosphate, alkyl, arylphosphonate and phosphorothioate esters. In addition, the 2'-hydroxyl group on ribonucleotides may be modified by including such groups as alkyl groups.

Probes of the invention are used in diagnostic tests, as capture or detection probes. Such capture probes are conventionally immobilized on a solid support, directly or indirectly, by covalent means or by passive adsorption. A detection probe is labeled by a detection marker selected from: radioactive isotopes, enzymes such as peroxidase, alkaline phosphatase, and enzymes able to hydrolyze a chromogenic, fluorogenic, or luminescent substrate, compounds that are chromogenic, fluorogenic, or luminescent, nucleotide base analogs, and biotin.

Probes of the invention are used in any conventional hybridization technique, such as dot blot (Maniatis et al., Molecular Cloning: A Laboratory Manual (1982) Cold Spring Harbor Laboratory Press, Cold Spring Harbor, N.Y.), Southern blot (Southern, J. Mol. Biol. (1975) 98:503), northern blot (identical to Southern blot with the exception that RNA is used as a target), or the sandwich technique (Dunn et al., Cell (1977) 12:23). The latter technique involves the use of a specific capture probe and/or a specific detection probe with nucleotide sequences that at least partially differ from each other.

A primer is a probe of usually about 10 to about 40 nucleotides that is used to initiate enzymatic polymerization of DNA in an amplification process (e.g., PCR), in an elongation process, or in a reverse transcription method. Primers used in diagnostic methods involving PCR are labeled by methods known in the art.

As described herein, the invention also encompasses (i) a reagent comprising a probe of the invention for detecting and/or identifying the presence of *Chlamydia* in a biological material; (ii) a method for detecting and/or identifying the presence of *Chlamydia* in a biological material, in which (a) a sample is recovered or derived from the biological material, (b) DNA or RNA is extracted from the material and denatured, and (c) exposed to a probe of the invention, for example, a capture, detection probe or both, under stringent hybridization conditions, such that hybridization is detected; and (iii) a method for detecting and/or identifying the presence of *Chlamydia* in a biological material, in which (a) a sample is recovered or derived from the biological material, (b) DNA is extracted therefrom, (c) the extracted DNA is primed with at least one, and preferably two, primers of the invention and amplified by polymerase chain reaction, and (d) the amplified DNA fragment is produced.

It is apparent that disclosure of polynucleotide sequences of SEQ ID No:1, 3 or 5, its homologs and partial sequences enable their corresponding amino acid sequences. Accordingly, a sixth aspect of the invention features a substantially purified polypeptide or polypeptide derivative having an amino acid sequence encoded by a polynucleotide of the invention.

A "substantially purified polypeptide" as used herein is defined as a polypeptide that is separated from the environment in which it naturally occurs and/or that is free of the majority of the polypeptides that are present in the environment in which it was synthesized. For example, a substantially purified polypeptide is free from cytoplasmic polypeptides. Those skilled in the art would readily understand that the polypeptides of the invention may be purified from a natural source, i.e., a *Chlamydia* strain, or produced by recombinant means.

Consistent with the sixth aspect of the invention are polypeptides, homologs or fragments which are modified or treated to enhance their immunogenicity in the target animal, in whom the polypeptide, homolog or fragments are intended to confer protection against *Chlamydia*. Such modifications or treatments include: amino acid substitutions with an amino acid derivative such as 3-methyhistidine, 4-hydroxyproline, 5-hydroxylysine etc., modifications or deletions which are carried out after preparation of the polypeptide, homolog or fragment, such as the modification of free amino, carboxyl or hydroxyl side groups of the amino acids.

Identification of homologous polypeptides or polypeptide derivatives encoded by polynucleotides of the invention which have specific antigenicity is achieved by screening for cross-reactivity with an antiserum raised against the polypeptide of reference having an amino acid sequence of SEQ ID No:1, 3 or 5. The procedure is as follows: a monospecific hyperimmune antiserum is raised against a purified reference polypeptide, a fusion polypeptide (for example, an expression product of MBP, GST, or His-tag systems, the description and instructions for use of which are contained in Invitrogen product manuals for pcDNA3.1/Myc-His(+) A, B, and C and for the Xpress™ System Protein Purification), or a synthetic peptide predicted to be antigenic. Where an antiserum is raised against a fusion polypeptide, two different fusion systems are employed. Specific antigenicity can be determined according to a number of methods, including Western blot (Towbin et al., Proc. Natl. Acad. Sci. USA (1979) 76:4350), dot blot, and ELISA, as described below.

In a Western blot assay, the product to be screened, either as a purified preparation or a total *E. coli* extract, is submitted to SDS-Page electrophoresis as described by Laemmli (Nature (1970) 227:680). After transfer to a nitrocellulose membrane, the material is further incubated with the monospecific hyperimmune antiserum diluted in the range of dilutions from about 1:5 to about 1:5000, preferably from about 1:100 to about 1:500. Specific antigenicity is shown once a band corresponding to the product exhibits reactivity at any of the dilutions in the above range.

In an ELISA assay, the product to be screened is preferably used as the coating antigen. A purified preparation is preferred, although a whole cell extract can also be used. Briefly, about 100 µl of a preparation at about 10 µg protein/ml are distributed into wells of a 96-well polycarbonate ELISA plate. The plate is incubated for 2 hours at 37° C. then overnight at 4° C. The plate is washed with phosphate buffer saline (PBS) containing 0.05% Tween 20 (PBS/Tween buffer). The wells are saturated with 250 µl PBS containing 1% bovine serum albumin (BSA) to prevent non-specific antibody binding. After 1 hour incubation at 37° C., the plate is washed with PBS/Tween buffer. The antiserum is serially diluted in PBS/Tween buffer containing 0.5% BSA. 100 µl of dilutions are added per well. The plate is incubated for 90 minutes at 37° C., washed and evaluated according to standard procedures. For example, a goat anti-rabbit peroxidase conjugate is added to the wells when specific antibodies were raised in rabbits. Incubation is carried out for 90 minutes at 37° C. and the plate is washed. The reaction is developed with the appropriate substrate and the reaction is measured by colorimetry (absorbance measured spectrophotometrically). Under the above experimental conditions, a positive reaction is shown by O.D. values greater than a non immune control serum.

In a dot blot assay, a purified product is preferred, although a whole cell extract can also be used. Briefly, a solution of the product at about 100 µg/ml is serially two-fold diluted in 50 mM Tris-HCl (pH 7.5). 100 µl of each dilution are applied to a nitrocellulose membrane 0.45 µm set in a 96-well dot blot apparatus (Biorad). The buffer is removed by applying vacuum to the system. Wells are washed by addition of 50 mM Tris-HCl (pH 7.5) and the membrane is air-dried. The membrane is saturated in blocking buffer (50 mM Tris-HCl (pH 7.5) 0.15 M NaCl, 10 g/L skim milk) and incubated with an antiserum dilution from about 1:50 to about 1:5000, preferably about 1:500. The reaction is revealed according to standard procedures. For example, a goat anti-rabbit peroxidase conjugate is added to the wells when rabbit antibodies are used. Incubation is carried out 90 minutes at 37° C. and the blot is washed. The reaction is developed with the appropriate substrate and stopped. The reaction is measured visually by the appearance of a colored spot, e.g., by colorimetry. Under the above experimental conditions, a positive reaction is shown once a colored spot is associated with a dilution of at least about 1:5, preferably of at least about 1:500.

Therapeutic or prophylactic efficacy of a polypeptide or derivative of the invention can be evaluated as described below. A seventh aspect of the invention provides (i) a composition of matter comprising a polypeptide of the invention together with a diluent or carrier; specifically (ii) a pharmaceutical composition containing a therapeutically or prophylactically effective amount of a polypeptide of the invention; (iii) a method for inducing an immune response against *Chlamydia* in a mammal, by administering to the mammal an immunogenically effective amount of a polypeptide of the invention to elicit a protective immune response to *Chlamydia*; and particularly, (iv) a method for preventing and/or treating a *Chlamydia* (e.g., *C. trachomatis. C. psittaci, C. pneumoniae.* or *C. pecorum*) infection, by administering a prophylactic or therapeutic amount of a polypeptide of the invention to an infected individual. Additionally, the seventh aspect of the invention encompasses the use of a polypeptide of the invention in the preparation of a medicament for preventing and/or treating *Chlamydia* infection.

As used herein, the immunogenic compositions of the invention are administered by conventional routes known the vaccine field, in particular to a mucosal (e.g., ocular, intranasal, pulmonary, oral, gastric, intestinal, rectal, vaginal, or urinary tract) surface or via the parenteral (e.g., subcutaneous, intradermal, intramuscular, intravenous, or intraperitoneal) route. The choice of administration route depends upon a number of parameters, such as the adjuvant associated with the polypeptide. If a mucosal adjuvant is used, the intranasal or oral route is preferred. If a lipid formulation or an aluminum compound is used, the parenteral route is preferred with the sub-cutaneous or intramuscular route being most preferred. The choice also depends upon the nature of the vaccine agent. For example, a polypeptide of the invention fused to CTB or LTB is best administered to a mucosal surface.

As used herein, the composition of the invention contains one or several polypeptides or derivatives of the invention. The composition optionally contains at least one additional *Chlamydia* antigen, or a subunit, fragment, homolog, mutant, or derivative thereof.

For use in a composition of the invention, a polypeptide or derivative thereof is formulated into or with liposomes, preferably neutral or anionic liposomes, microspheres, ISCOMS, or virus-like-particles (VLPs) to facilitate delivery and/or enhance the immune response. These compounds are readily available to one skilled in the art; for example, see Liposomes: A Practical Approach, RCP New Ed, IRL press (1990).

Adjuvants other than liposomes and the like are also used and are known in the art. Adjuvants may protect the antigen from rapid dispersal by sequestering it in a local deposit, or they may contain substances that stimulate the host to secrete factors that are chemotactic for macrophages and other components of the immune system. An appropriate selection can conventionally be made by those skilled in the art, for example, from those described below (under the eleventh aspect of the invention).

Treatment is achieved in a single dose or repeated as necessary at intervals, as can be determined readily by one skilled in the art. For example, a priming dose is followed by three booster doses at weekly or monthly intervals. An appropriate dose depends on various parameters including the recipient (e.g., adult or infant), the particular vaccine antigen, the route and frequency of administration, the presence/absence or type of adjuvant, and the desired effect (e.g., protection and/or treatment), as can be determined by one skilled in the art. In general, a vaccine antigen of the invention is administered by a mucosal route in an amount from about 10 μg to about 500 mg, preferably from about 1 mg to about 200 mg. For the parenteral route of administration, the dose usually does not exceed about 1 mg, preferably about 100 μg.

When used as vaccine agents, polynucleotides and polypeptides of the invention may be used sequentially as part of a multistep immunization process. For example, a mammal is initially primed with a vaccine vector of the invention such as a pox virus, e.g., via the parenteral route, and then boosted twice with the polypeptide encoded by the vaccine vector, e.g., via the mucosal route. In another example, liposomes associated with a polypeptide or derivative of the invention is also used for priming, with boosting being carried out mucosally using a soluble polypeptide or derivative of the invention in combination with a mucosal adjuvant (e.g., LT).

A polypeptide derivative of the invention is also used in accordance with the seventh aspect as a diagnostic reagent for detecting the presence of anti-*Chlamydia* antibodies, e.g., in a blood sample. Such polypeptides are about 5 to about 80, preferably about 10 to about 50 amino acids in length. They are either labeled or unlabeled, depending upon the diagnostic method. Diagnostic methods involving such a reagent are described below.

Upon expression of a DNA molecule of the invention, a polypeptide or polypeptide derivative is produced and purified using known laboratory techniques. As described above, the polypeptide or polypeptide derivative may be produced as a fusion protein containing a fused tail that facilitates purification. The fusion product is used to immunize a small mammal, e.g., a mouse or a rabbit, in order to raise antibodies against the polypeptide or polypeptide derivative (monospecific antibodies). Accordingly, an eighth aspect of the invention provides a monospecific antibody that binds to a polypeptide or polypeptide derivative of the invention.

By "monospecific antibody" is meant an antibody that is capable of reacting with a unique naturally-occurring *Chlamydia* polypeptide. An antibody of the invention is either polyclonal or monoclonal. Monospecific antibodies may be recombinant, e.g., chimeric (e.g., constituted by a variable region of murine origin associated with a human constant region), humanized (a human immunoglobulin constant backbone together with hypervariable region of animal, e.g., murine, origin), and/or single chain. Both polyclonal and monospecific antibodies may also be in the form of immunoglobulin fragments, e.g., F(ab)'2 or Fab fragments. The antibodies of the invention are of any isotype, e.g., IgG or IgA, and polyclonal antibodies are of a single isotype or a mixture of isotypes.

Antibodies against the polypeptides, homologs or fragments of the present invention are generated by immunization of a mammal with a composition comprising said polypeptide, homolog or fragment. Such antibodies may be polyclonal or monoclonal. Methods to produce polyclonal or monoclonal antibodies are well known in the art. For a review, see "Antibodies, A Laboratory Manual, Cold Spring Harbor Laboratory, Eds. E. Harlow and D. Lane (1988), and D. E. Yelton et al., 1981. Ann. Rev. Biochem. 50:657-680. For monoclonal antibodies, see Kohler & Milstein (1975) Nature 256:495-497.

The antibodies of the invention, which are raised to a polypeptide or polypeptide derivative of the invention, are produced and identified using standard immunological assays, e.g., Western blot analysis, dot blot assay, or ELISA (see, e.g., Coligan et al., Current Protocols in Immunology (1994) John Wiley & Sons, Inc., New York, N.Y.). The antibodies are used in diagnostic methods to detect the presence of a *Chlamydia* antigen in a sample, such as a biological sample. The antibodies are also used in affinity chromatography for purifying a polypeptide or polypeptide derivative of the invention. As is discussed further below, such antibodies may be used in prophylactic and therapeutic passive immunization methods.

Accordingly, a ninth aspect of the invention provides (i) a reagent for detecting the presence of *Chlamydia* in a biological sample that contains an antibody, polypeptide, or polypeptide derivative of the invention; and (ii) a diagnostic method for detecting the presence of *Chlamydia* in a biological sample, by contacting the biological sample with an antibody, a polypeptide, or a polypeptide derivative of the invention, such that an immune complex is formed, and by detecting such complex to indicate the presence of *Chlamydia* in the sample or the organism from which the sample is derived.

Those skilled in the art will readily understand that the immune complex is formed between a component of the sample and the antibody, polypeptide, or polypeptide derivative, whichever is used, and that any unbound material is removed prior to detecting the complex. It is understood that a polypeptide reagent is useful for detecting the presence of anti-*Chlamydia* antibodies in a sample, e.g., a blood sample, while an antibody of the invention is used for screening a sample, such as a gastric extract or biopsy, for the presence of *Chlamydia* polypeptides.

For diagnostic applications, the reagent (i.e., the antibody, polypeptide, or polypeptide derivative of the invention) is either in a free state or immobilized on a solid support, such as a tube, a bead, or any other conventional support used in the field. Immobilization is achieved using direct or indirect means. Direct means include passive adsorption (non-covalent binding) or covalent binding between the support and the reagent. By "indirect means" is meant that an anti-reagent compound that interacts with a reagent is first attached to the solid support. For example, if a polypeptide reagent is used, an antibody that binds to it can serve as an anti-reagent, provided that it binds to an epitope that is not involved in the recognition of antibodies in biological samples. Indirect means may also employ a ligand-receptor system, for example, where a molecule such as a vitamin is grafted onto the polypeptide reagent and the corresponding receptor immobilized on the solid phase. This is illustrated by the biotin-streptavidin system. Alternatively, a peptide tail is added chemically or by genetic engineering to the reagent and the grafted or fused product immobilized by passive adsorption or covalent linkage of the peptide tail.

Such diagnostic agents may be included in a kit which also comprises instructions for use. The reagent is labeled with a detection means which allows for the detection of the reagent when it is bound to its target. The detection means may be a fluorescent agent such as fluorescein isocyanate or fluorescein isothiocyanate, or an enzyme such as horse radish peroxidase or luciferase or alkaline phosphatase, or a radioactive element such as $^{125}$I or $^{51}$Cr.

Accordingly, a tenth aspect of the invention provides a process for purifying, from a biological sample, a polypeptide or polypeptide derivative of the invention, which involves carrying out antibody-based affinity chromatography with the biological sample, wherein the antibody is a monospecific antibody of the invention.

For use in a purification process of the invention, the antibody is either polyclonal or monospecific, and preferably is of the IgG type. Purified IgGs is prepared from an antiserum using standard methods (see, e.g., Coligan et al., Current Protocols in Immunology (1994)John Wiley & Sons, Inc., New York, N.Y.). Conventional chromatography supports, as well as standard methods for grafting antibodies, are described in, e.g., Antibodies: A Laboratory Manual, D. Lane, E. Harlow, Eds. (1988) and outlined below.

Briefly, a biological sample, such as an *C. pneumoniae* extract preferably in a buffer solution, is applied to a chromatography material, preferably equilibrated with the buffer used to dilute the biological sample so that the polypeptide or polypeptide derivative of the invention (i.e., the antigen) is allowed to adsorb onto the material. The chromatography material, such as a gel or a resin coupled to an antibody of the invention, is in either a batch form or a column. The unbound components are washed off and the antigen is then eluted with an appropriate elution buffer, such as a glycine buffer or a buffer containing a chaotropic agent, e.g., guanidine HCl, or high salt concentration (e.g., 3 M $MgCl_2$). Eluted fractions are recovered and the presence of the antigen is detected, e.g., by measuring the absorbance at 280 nm.

An eleventh aspect of the invention provides (i) a composition of matter comprising a monospecific antibody of the invention, together with a diluent or carrier; (ii) a pharmaceutical composition comprising a therapeutically or prophylactically effective amount of a monospecific antibody of the invention, and (iii) a method for treating or preventing a *Chlamydia* (e.g., *C. trachomatis*, *C. psittaci*, *C. pneumoniae* or *C. pecorum*) infection, by administering a therapeutic or prophylactic amount of a monospecific antibody of the invention to an infected individual. Additionally, the eleventh aspect of the invention encompasses the use of a monospecific antibody of the invention in the preparation of a medicament for treating or preventing *Chlamydia* infection.

The monospecific antibody is either polyclonal or monoclonal, preferably of the IgA isotype (predominantly). In passive immunization, the antibody is administered to a mucosal surface of a mammal, e.g., the gastric mucosa, e.g., orally or intragastrically, advantageously, in the presence of a bicarbonate buffer. Alternatively, systemic administration, not requiring a bicarbonate buffer, is carried out. A monospecific antibody of the invention is administered as a single active component or as a mixture with at least one monospecific antibody specific for a different *Chlamydia* polypeptide. The amount of antibody and the particular regimen used are readily determined by one skilled in the art. For example, daily administration of about 100 to 1,000 mg of antibodies over one week, or three doses per day of about 100 to 1,000 mg of antibodies over two or three days, are effective regimens for most purposes.

Therapeutic or prophylactic efficacy are evaluated using standard methods in the art, e.g., by measuring induction of a mucosal immune response or induction of protective and/or therapeutic immunity, using, e.g., the *C. pneumoniae* mouse model. Those skilled in the art will readily recognize that the *C. pneumoniae* strain of the model may be replaced with another *Chlamydia* strain. For example, the efficacy of DNA molecules and polypeptides from *C. pneumoniae* is preferably evaluated in a mouse model using *C. pneumoniae* strain. Protection is determined by comparing the degree of *Chlamydia* infection to that of a control group. Protection is shown when infection is reduced by comparison to the control group. Such an evaluation is made for polynucleotides, vaccine vectors, polypeptides and derivatives thereof, as well as antibodies of the invention.

Adjuvants useful in any of the vaccine compositions described above are as follows.

Adjuvants for parenteral administration include aluminum compounds, such as aluminum hydroxide, aluminum phosphate, and aluminum hydroxy phosphate. The antigen is precipitated with, or adsorbed onto, the aluminum compound according to standard protocols. Other adjuvants, such as RIBI (ImmunoChem, Hamilton, Mont.), are used in parenteral administration.

Adjuvants for mucosal administration include bacterial toxins, e.g., the cholera toxin (CT), the *E. coli* heat-labile toxin (LT), the *Clostridium difficile* toxin A and the pertussis toxin (PT), or combinations, subunits, toxoids, or mutants thereof such as a purified preparation of native cholera toxin subunit B (CTB). Fragments, homologs, derivatives, and fusions to any of these toxins are also suitable, provided that they retain adjuvant activity. Preferably, a mutant having reduced toxicity is used. Suitable mutants are described, e.g., in WO 95/17211 (Arg-7-Lys CT mutant), WO 96/06627 (Arg-192-Gly LT mutant), and WO 95/34323 (Arg-9-Lys and Glu-129-Gly PT mutant). Additional LT mutants that are used in the methods and compositions of the invention include, e.g., Ser-63-Lys, Ala-69Gly, Glu-110-Asp, and Glu-112-Asp mutants. Other adjuvants, such as a bacterial monophosphoryl lipid A (MPLA) of, e.g., *E. coli, Salmonella minnesota, Salmonella typhimurium*, or *Shigella flexneri*; saponins, or polylactide glycolide (PLGA) microspheres, is also be used in mucosal administration.

Adjuvants useful for both mucosal and parenteral administrations include polyphosphazene (WO 95/02415), DC-chol (3 b-(N-(N',N'-dimethyl aminomethane)-carbamoyl) cholesterol; U.S. Pat. No. 5,283,185 and WO 96/14831) and QS-21 (WO 88/09336).

Any pharmaceutical composition of the invention containing a polynucleotide, a polypeptide, a polypeptide derivative, or an antibody of the invention, is manufactured in a conventional manner. In particular, it is formulated with a pharmaceutically acceptable diluent or carrier, e.g., water or a saline solution such as phosphate buffer saline. In general, a diluent or carrier is selected on the basis of the mode and route of administration, and standard pharmaceutical practice. Suitable pharmaceutical carriers or diluents, as well as pharmaceutical necessities for their use in pharmaceutical formulations, are described in *Remington's Pharmaceutical Sciences*, a standard reference text in this field and in the USP/NF.

The invention also includes methods in which *Chlamydia* infection are treated by oral administration of a *Chlamydia* polypeptide of the invention and a mucosal adjuvant, in combination with an antibiotic, an antacid, sucralfate, or a combination thereof. Examples of such compounds that can be administered with the vaccine antigen and the adjuvant are antibiotics, including, e.g., macrolides, tetracyclines, and derivatives thereof (specific examples of antibiotics that can be used include azithromycin or doxicyclin or immunomodulators such as cytokines or steroids). In addition, compounds containing more than one of the above-listed components coupled together, are used. The invention also includes compositions for carrying out these methods, i.e., compositions containing a *Chlamydia* antigen (or antigens) of the invention, an adjuvant, and one or more of the above-listed compounds, in a pharmaceutically acceptable carrier or diluent.

It has recently been shown that the 9kDa cysteine rich membrane protein contains a sequence cross-reactive with the murine alpha-myosin heavy chain epitope M7A-alpha, an epitope conserved in humans (Bachmaier et al., Science (1999) 283:1335). This cross-reactivity is proposed to contribute to the development of cardiovascular disease, so it may be beneficial to remove this epitope, and any other epitopes cross-reactive with human antigens, from the protein if it is to be used as a vaccine. Accordingly, a further embodiment of the present invention includes the modification of the coding sequence, for example, by deletion or substitution of the nucleotides encoding the epitope from polynucleotides encoding the protein, as to improve the efficacy and safety of the protein as a vaccine. A similar approach may be appropriate for any protective antigen found to have unwanted homologies or cross-reactivities with human antigens.

Amounts of the above-listed compounds used in the methods and compositions of the invention are readily determined by one skilled in the art. Treatment/immunization schedules are also known and readily designed by one skilled in the art. For example, the non-vaccine components can be administered on days 1-14, and the vaccine antigen+adjuvant can be administered on days 7, 14, 21, and 28.

EXAMPLES

The above disclosure generally describes the present invention. A more complete understanding can be obtained by reference to the following specific examples. These examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

Example 1

This example illustrates the preparation of a plasmid vector pCACPNM555a containing the full length 76kDa protein gene.

The full-length 76kDa protein gene (SEQ ID No:1) was amplified from *Chlamydia pneumoniae* genomic DNA by polymerase chain reaction (PCR) using a 5' primer (5' ATAAGAAT GCGGCCGCCACCATGGTTAATCCTATTGGTCCAGG 3') (SEQ ID No:9) and a 3' primer (5' GCGCC GGATCCCTTGGAGATAACCAGAATATAGAG 3') (SEQ ID No:10). The 5' primer contains a Not I restriction site, a ribosome binding site, an initiation codon and a sequence close to the 5' end of the full-length 76kDa protein coding sequence. The 3' primer includes the sequence encoding the C-terminal sequence of the 76kDa protein and a Bam HI restriction site. The stop codon was excluded and an additional nucleotide was inserted to obtain an in-frame fusion with the Histidine tag.

After amplification, the PCR fragment was purified using QIAquick™ PCR purification kit (Qiagen) and then digested with Not I and Bam HI and cloned into the pCA-Myc-His eukaryotic expression vector describe in Example 2 (FIG. 4) with transcription under control of the human CMV promoter.

Example 2

This example illustrates the preparation of the eukaryotic expression vector pCA/Myc-His.

Plasmid pcDNA3.1(−)Myc-His C (Invitrogen) was restricted with Spe I and Bam HI to remove the CMV promoter and the remaining vector fragment was isolated. The CMV promoter and intron A from plasmid VR-1012 (Vical) was isolated on a Spe I/Bam HI fragment. The fragments were ligated together to produce plasmid pCA/Myc-His. The Not I/Bam HI restricted PCR fragment containing the full-length 76kDa protein gene(SEQ ID No:1) was ligated into the Not I and Bam HI restricted plasmid pCA/Myc-His to produce plasmid pCACPNM555a (FIG. 4).

The resulting plasmid, pCACPNM555a, was transferred by electroporation into *E. coli* XL-1 blue (Stratagene) which was grown in LB broth containing 50 μg/ml of carbenicillin. The plasmid was isolated by Endo Free Plasmid Giga Kit™ (Qiagen) large scale DNA purification system. DNA concentration was determined by absorbance at 260 nm and the plasmid was verified after gel electrophoresis and Ethidium bromide staining and comparison to molecular weight standards. The 5' and 3' ends of the gene were verified by sequencing using a LiCor model 4000 L DNA sequencer and IRD-800 labelled primers.

Example 3

This example illustrates the immunization of mice to achieve protection against an intranasal challenge of *C. pneumoniae*.

It has been previously demonstrated (Yang et. al., 1993) that mice are susceptible to intranasal infection with different isolates of *C. pneumoniae*. Strain AR-39 (Grayston, 1989) was used in Balb/c mice as a challenge infection model to examine the capacity of *Chlamydia* gene products delivered as naked DNA to elicit a protective response against a sublethal *C. pneumoniae* lung infection. Protective immunity is defined as an accelerated clearance of pulmonary infection.

Groups of 7 to 9 week old male Balb/c mice (7 to 10 per group) were immunized intramuscularly (i.m.) plus intranasally (i.n.) with plasmid DNA containing the coding sequence of *C.pneumoniae* full-length 76kDa protein as described in Examples 1 and 2. Saline or the plasmid vector lacking an inserted Chlamydial gene was given to groups of control animals.

For i.m. immunization alternate left and right quadriceps were injected with 100 μg of DNA in 50 μl of PBS on three occasions at 0, 3 and 6 weeks. For i.n. immunization, anaesthetized mice aspirated 50 μl of PBS containing 50 μg DNA on three occasions at 0, 3 and 6 weeks. At week 8, immunized mice were inoculated i.n. with 5×10⁵ IFU of *C. pneumoniae*, strain AR39 in 100 μl of SPG buffer to test their ability to limit the growth of a sublethal *C. pneumoniae* challenge.

Lungs were taken from mice at days 5 and 9 post-challenge and immediately homogenised in SPG buffer (7.5% sucrose, 5 mM glutamate, 12.5 mM phosphate pH 7.5). The homogenate was stored frozen at −70° C. until assay. Dilutions of the homogenate were assayed for the presence of infectious *Chlamydia* by inoculation onto monolayers of susceptible cells. The inoculum was centrifuged onto the cells at 3000 rpm for 1 hour, then the cells were incubated for three days at 35° C. in the presence of 1 μg/ml cycloheximide. After incubation the monolayers were fixed with formalin and methanol then immunoperoxidase stained for the presence of Chlamydial inclusions using convalescent sera from rabbits infected with *C.pneumoniae* and metal-enhanced DAB as a peroxidase substrate.

FIG. 7 and Table 1 show that mice immunized i.n. and i.m. with pCACPNM555a had Chlamydial lung titers less than 30,000 IFU/lung (mean 23,550) in 5 of 6 cases at day 9 whereas the range of values for control mice sham immunized with saline were 20,800 to 323,300 IFU/lung (mean 206,375) for (Table 1). DNA immunisation per se was not responsible for the observed protective effect since two other plasmid DNA constructs, pCACPNM806 and pCACPNM760, failed to protect, with lung titers in immunised mice similar to those obtained for saline-immunized control mice. The constructs pCACPNM806 and pCACPNM760 are identical to pCACPNM555a except that the nucleotide sequence encoding the full-length 76kDa protein is replaced with *C. pneumoniae* nucleotide sequences encoding an unrelated sequence.

TABLE 1

BACTERIAL LOAD (INCLUSION FORMING UNITS PER LUNG) IN THE LUNGS OF BALB/C MICE IMMUNIZED WITH VARIOUS DNA IMMUNIZATION CONSTRUCTS

| | IMMUNIZING CONSTRUCT | | | |
|---|---|---|---|---|
| MOUSE | Saline Day 9 | pCACPNM806 Day 9 | pCACPNM760 Day 9 | pCACPNM-555a Day 9 |
| 1 | 225900 | 36700 | 140300 | 27300 |
| 2 | 20800 | 238700 | 128400 | 15200 |
| 3 | 286100 | 52300 | 88700 | 34600 |
| 4 | 106700 | 109600 | 25600 | 20500 |
| 5 | 323300 | 290000 | 37200 | 22000 |
| 6 | 144300 | 298800 | 5900 | 21700 |
| 7 | 261700 | | | |
| 8 | 282200 | | | |
| MEAN | 206375 | 171016.667 | 71016.6667 | 23550 |
| SD | 105183.9 | 119141.32 | 56306.57 | 6648.53 |
| Wilcoxon p | | 0.8518 | 0.0293 | 0.008 |

Example 4

This example illustrates the preparation of a plasmid vector pCAI555 containing a 5'-truncated 76kDa protein gene.

The 5' truncated 76kDa protein gene (SEQ ID No:3) was amplified from *Chlamydia pneumoniae* genomic DNA by polymerase chain reaction (PCR) using a 5' primer (5' ATAAGAAT GCGGCCGCCACCATGAGTCTGGCAGATAAGCTGGG 3') (SEQ ID No:11) and a 3' primer (5' GCGCC GGATCCCTTGGAGATAACCAGAATATA 3') (SEQ ID No:12). The 5' primer contains a Not I restriction site, a ribosome binding site, an initiation codon and a sequence at the second Met codon of the 76kDa protein coding sequence. The 3' primer includes the sequence encoding the C-terminal sequence of the 3' 76kDa protein and a Bam HI restriction site. The stop codon was excluded and an additional nucleotide was inserted to obtain an in-frame fusion with the Histidine tag.

After amplification, the PCR fragment was purified using QIAquick™ PCR purification kit (Qiagen) and then digested with Not I and Bam HI and cloned into the pCA-Myc-His eukaryotic expression vector describe in Example 5 (FIG. 5) with transcription under control of the human CMV promoter.

Example 5

This example illustrates the preparation of the eukaryotic expression vector pCA/Myc-His.

Figure 5:
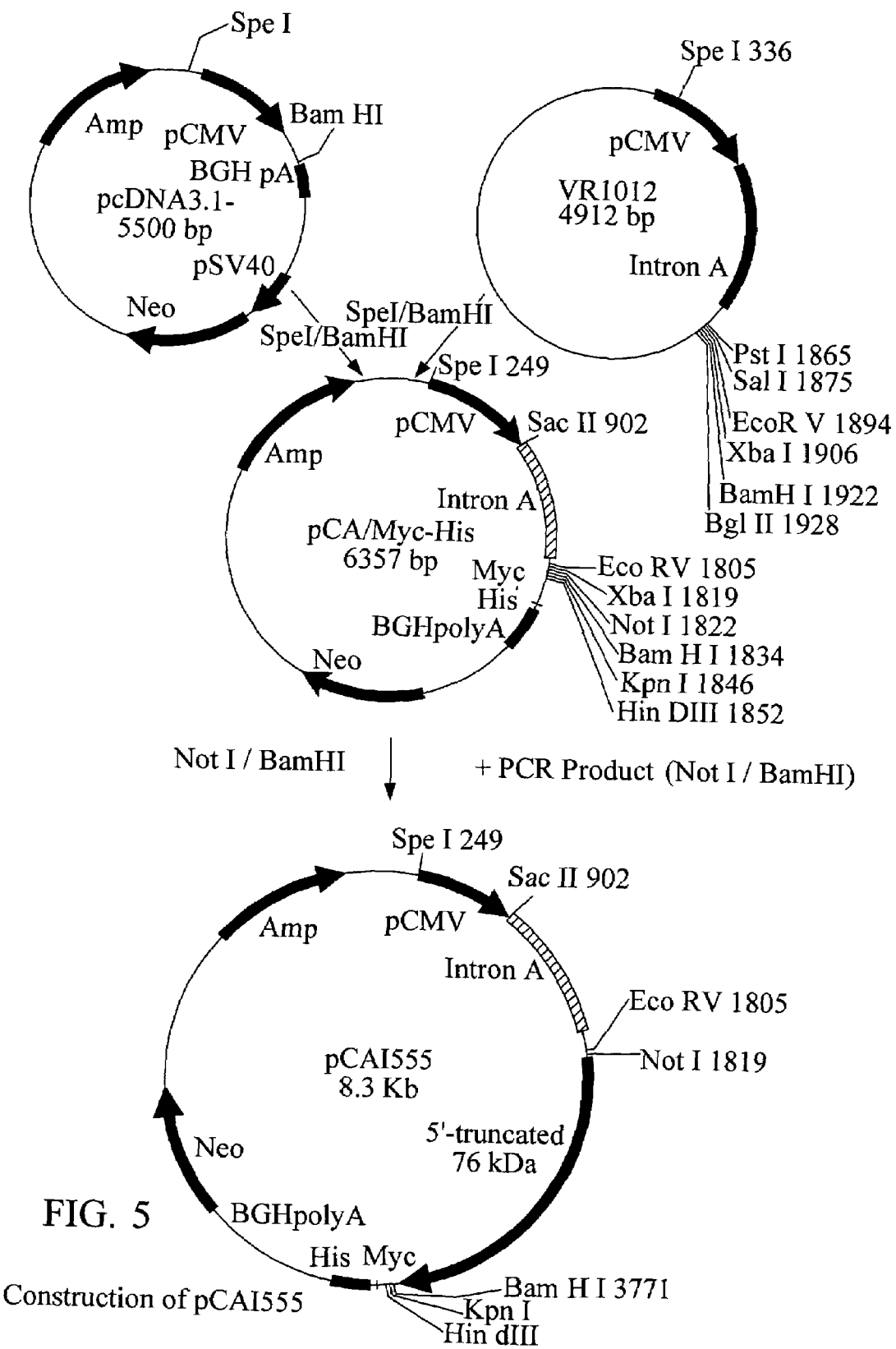
FIG. 5 shows the construction and elements of plasmid pCAI555, containing a 5'-truncated version of the 76kDa gene.

Plasmid pcDNA3.1(−)Myc-His C (Invitrogen) was restricted with Spe I and Bam HI to remove the CMV promoter and the remaining vector fragment was isolated. The CMV promoter and intron A from plasmid VR-1012 (Vical) was isolated on a Spe I/Bam HI fragment. The fragments were ligated together to produce plasmid pCA/Myc-His. The Not I/Bam HI restricted PCR fragment containing the 5' truncated 76kDa protein gene (SEQ ID No:3) was ligated into the Not I and Bam HI restricted plasmid pCA/Myc-His to produce plasmid pCAI555 (FIG. 5).

The resulting plasmid, pCAI555, was transferred by electroporation into E. coli XL-1 blue (Stratagene) which was grown in LB broth containing 50 μg/ml of carbenicillin. The plasmid was isolated by Endo Free Plasmid Giga Kit™ (Qiagen) large scale DNA purification system. DNA concentration was determined by absorbance at 260 nm and the plasmid was verified after gel electrophoresis and Ethidium bromide staining and comparison to molecular weight standards. The 5' and 3' ends of the gene were verified by sequencing using a LiCor model 4000 L DNA sequencer and IRD-800 labelled primers.

Example 6

This Example illustrates the immunization of mice to achieve protection against an intranasal challenge of C. pneumoniae. The procedures are described in Example 3 above, except that the DNA plasmid used for immunization contains the coding sequence of C. pneumoniae 5'-truncated 76kDa protein, as described in Examples 4 and 5.

FIG. 8 and Table 2 show that mice immunized i.n. and i.m. with pCAI555 had Chlamydial lung titers less than 13000 IFU/lung (mean 6050) in 6 of 6 cases at day 9 whereas the range of values for control mice sham immunized with saline were 106,100 IFU/lung (mean 39,625) for (Table 2). DNA immunisation per se was not responsible for the observed protective effect since two other plasmid DNA constructs, pCAI116 and pCAI178, failed to protect, with lung titers in immunised mice similar to those obtained for saline-immunized control mice. The constructs pCAI116 and pCAI178 are identical to pCAI555 except that the nucleotide sequence encoding the 5'-truncated 76kDa protein is replaced with a C.pneumoniae nucleotide sequence encoding an unprotective sequence and the nucleoside 5'-diphosphate phosphotransferase protein.

TABLE 2

BACTERIAL LOAD (INCLUSION FORMING UNITS PER LUNG) IN THE LUNGS OF BALB/C MICE IMMUNIZED WITH VARIOUS DNA IMMUNIZATION CONSTRUCTS
IMMUNIZING CONSTRUCT

| MOUSE | Saline Day 9 | pCAI116 Day 9 | pCAI178 Day 9 | pCAI555 Day 9 |
|---|---|---|---|---|
| 1 | 1700 | 47700 | 80600 | 6100 |
| 2 | 36200 | 12600 | 31900 | 10700 |
| 3 | 106100 | 28600 | 30600 | 500 |
| 4 | 33500 | 17700 | 6500 | 5100 |
| 5 | 70400 | 77300 | 53000 | 1100 |
| 6 | 48700 | 17600 | 79500 | 12800 |
| 7 | 600 | | | |
| 8 | 19800 | | | |
| 9 | 29500 | | | |
| 10 | 100000 | | | |
| 11 | 15000 | | | |
| 12 | 56600 | | | |
| 13 | 60300 | | | |
| 14 | 88800 | | | |
| 15 | 30400 | | | |
| 16 | 69300 | | | |
| 17 | 47500 | | | |
| 18 | 96500 | | | |
| 19 | 30200 | | | |
| 20 | 84800 | | | |
| 21 | 3800 | | | |
| 22 | 65900 | | | |
| 23 | 33000 | | | |
| MEAN | 49069.57 | 33583.33 | 47016.67 | 6050 |
| SD | 32120.48 | 24832.67 | 29524.32 | 4967.80 |

Example 7

This example illustrates the preparation of a plasmid vector pCAD76kDa containing a 3'-truncated 76kDa protein gene.

The 3'-truncated 76kDa protein gene (SEQ ID No:7 which contains SEQ ID No:5) was amplified from Chlamydia pneumoniae genomic DNA by polymerase chain reaction (PCR) using a 5' primer (5' GC TCTAGACCGCCATGACAAAAAAACATTATGCTTGGG 3') (SEQ ID No:13) and a 3' primer (5' CG GGATCCATAGAACTTGCTGCAGCGGG 3') (SEQ ID No:14). The 5' primer contains a Xba I restriction site, a ribosome binding site, an initiation codon and a sequence 765 bp upstream of the 5' end of the 76kDa protein coding sequence. The 3' primer includes a 21 bp the sequence downstream of codon 452 of the 76kDa protein and a Bam HI restriction site. An additional nucleotide was inserted to obtain an in-frame fusion with the Histidine tag. Note that inclusion of the 765 bp 5' region and the 21 bp 3' regions in SEQ ID No:7 were inadvertent. These sequences are not part of the 76kDa protein gene. Nevertheless, immunoprotection was achieved using this sequence (Example 6).

After amplification, the PCR fragment was purified using QIAquick™ PCR purification kit (Qiagen) and then digested with Xba I and Bam HI and cloned into the pCA-Myc-His eukaryotic expression vector describe in Example 8 (FIG. 6) with transcription under control of the human CMV promoter.

Example 8

This Example illustrates the preparation of the eukaryotic expression vector pCA/Myc-His.

Figure 6:
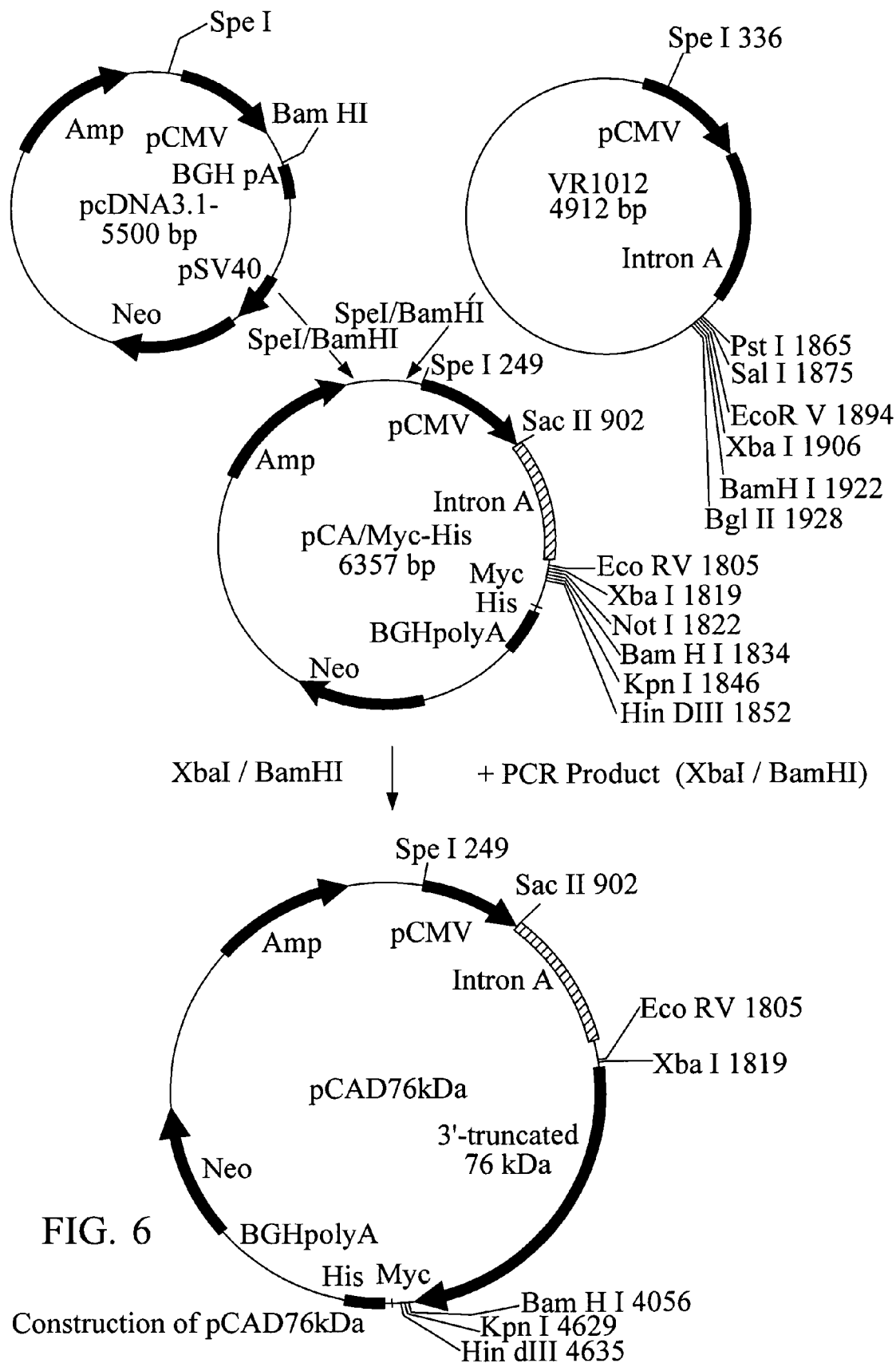
FIG. 6 shows the construction and elements of plasmid pCAD76kDa, containing a 3'-truncated version of the 76kDa gene from FIG. 3.

Plasmid pcDNA3.1(−)Myc-His C (Invitrogen) was restricted with Spe I and Bam HI to remove the CMV promoter and the remaining vector fragment was isolated. The CMV promoter and intron A from plasmid VR-1012 (Vical) was isolated on a Spe I/Bam HI fragment. The fragments were ligated together to produce plasmid pCA/Myc-His. The Xba I/Bam HI restricted PCR fragment containing a 3'-truncated 76kDa protein gene (SEQ ID No:7) was ligated into the Xba I and Bam HI restricted plasmid pCA/Myc-His to produce plasmid pCAD76kDa (FIG. 6).

The resulting plasmid, pCAD76kDa, was transferred by electroporation into *E. coli* XL-1 blue (Stratagene) which was grown in LB broth containing 50 µg/ml of carbenicillin. The plasmid was isolated by Endo Free Plasmid Giga Kit™ (Qiagen) large scale DNA purification system. DNA concentration was determined by absorbance at 260 nm and the plasmid was verified after gel electrophoresis and Ethidium bromide staining and comparison to molecular weight standards. The 5' and 3' ends of the gene were verified by sequencing using a LiCor model 4000 L DNA sequencer and IRD-800 labelled primers.

Example 9

This example illustrates the immunization of mice to achieve protection against an intranasal challenge of *C. pneumoniae*. The procedures are as described in Example 3 above, except that the DNA plasmid used for immunization contains the coding sequence of *C. pneumoniae* 3'-truncated 76kDa protein, as described in Examples 7 and 8.

FIG. 9 and Table 3 show that mice immunized i.n. and i.m. with pCAD76kDa had Chlamydial lung titers less than 2400 in 5 of 5 cases whereas the range of values for control mice were 1800-23100 IFU/lung (mean 11811) and 16600-26100 IFU/lung (mean 22100) for sham immunized with saline or immunized with the unmodified vector respectively (Table 2). The lack of protection with the unmodified vector confirms that DNA per se was not responsible for the observed protective effect. This is further supported by the results obtained for one additional plasmid DNA construct, pdagA, that failed to protect, and for which the mean lung titers were similar to those obtained for saline-immunized control mice. The construct pdagA is identical to pCAD76kDa except that the nucleotide sequence encoding the 3'-truncated 76kDa protein is replaced with a *C.pneumoniae* nucleotide sequence encoding the protein dagA.

TABLE 3

BACTERIAL LOAD (INCLUSION FORMING UNITS PER LUNG) IN THE LUNGS OF BALB/C MICE IMMUNIZED WITH VARIOUS DNA IMMUNIZATION CONSTRUCTS

| | IMMUNIZING CONSTRUCT | | | |
|---|---|---|---|---|
| MOUSE | Saline | Vector | pdagA | pCAD76 kDa |
| 1 | 17700 | 19900 | 16000 | 1700 |
| 2 | 3900 | 16600 | 500 | 2000 |
| 3 | 1800 | 24300 | 18500 | 2300 |
| 4 | 16400 | 26100 | 12800 | 2100 |
| 5 | 11700 | 23600 | 6400 | 600 |
| 6 | 23100 | | | |
| 7 | 12000 | | | |
| 8 | 5300 | | | |
| 9 | 14400 | | | |
| 10 | 18700 | | | |
| 11 | 7300 | | | |
| 12 | 8400 | | | |
| MEAN | 11725 | 22100 | 10840 | 1740 |
| SD | 6567.71 | 3813.79 | 7344.59 | 673.05 |

SEQUENCE LISTING

```
<160> NUMBER OF SEQ ID NOS: 14

<210> SEQ ID NO 1
<211> LENGTH: 2156
<212> TYPE: DNA
<213> ORGANISM: Chlamydia pneumoniae
<220> FEATURE:
<221> NAME/KEY: CDS
<222> LOCATION: (101)..(2053)

<400> SEQUENCE: 1
ataaaatctt taaaaacagg ctcgcattaa ttattagtga gagctttttt tttatttttt      60
ataataaaac taaaagattt ttattatttt ttgagttttt atg gtt aat cct att       115
                                            Met Val Asn Pro Ile
                                              1               5 ggt cca ggt cct ata gac gaa aca gaa cgc aca cct ccc gca gat ctt       163
Gly Pro Gly Pro Ile Asp Glu Thr Glu Arg Thr Pro Pro Ala Asp Leu
                 10                  15                  20 tct gct caa gga ttg gag gcg agt gca gca aat aag agt gcg gaa gct       211
Ser Ala Gln Gly Leu Glu Ala Ser Ala Ala Asn Lys Ser Ala Glu Ala
             25                  30                  35 caa aga ata gca ggt gcg gaa gct aag cct aaa gaa tct aag acc gat       259
Gln Arg Ile Ala Gly Ala Glu Ala Lys Pro Lys Glu Ser Lys Thr Asp
         40                  45                  50 tct gta gag cga tgg agc atc ttg cgt tct gca gtg aat gct ctc atg       307
Ser Val Glu Arg Trp Ser Ile Leu Arg Ser Ala Val Asn Ala Leu Met
     55                  60                  65 agt ctg gca gat aag ctg ggt att gct tct agt aac agc tcg tct tct       355
```

```
Ser Leu Ala Asp Lys Leu Gly Ile Ala Ser Ser Asn Ser Ser Ser
 70              75              80              85 act agc aga tct gca gac gtg gac tca acg aca gcg acc gca cct acg      403
Thr Ser Arg Ser Ala Asp Val Asp Ser Thr Thr Ala Thr Ala Pro Thr
             90              95             100 cct cct cca ccc acg ttt gat gat tat aag act caa gcg caa aca gct      451
Pro Pro Pro Pro Thr Phe Asp Asp Tyr Lys Thr Gln Ala Gln Thr Ala
            105             110             115 tac gat act atc ttt acc tca aca tca cta gct gac ata cag gct gct      499
Tyr Asp Thr Ile Phe Thr Ser Thr Ser Leu Ala Asp Ile Gln Ala Ala
            120             125             130 ttg gtg agc ctc cag gat gct gtc act aat ata aag gat aca gcg gct      547
Leu Val Ser Leu Gln Asp Ala Val Thr Asn Ile Lys Asp Thr Ala Ala
            135             140             145 act gat gag gaa acc gca atc gct gcg gag tgg gaa act aag aat gcc      595
Thr Asp Glu Glu Thr Ala Ile Ala Ala Glu Trp Glu Thr Lys Asn Ala
150             155             160             165 gat gca gtt aaa gtt ggc gcg caa att aca gaa tta gcg aaa tat gct      643
Asp Ala Val Lys Val Gly Ala Gln Ile Thr Glu Leu Ala Lys Tyr Ala
                170             175             180 tcg gat aac caa gcg att ctt gac tct tta ggt aaa ctg act tcc ttc      691
Ser Asp Asn Gln Ala Ile Leu Asp Ser Leu Gly Lys Leu Thr Ser Phe
                185             190             195 gac ctc tta cag gct gct ctt ctc caa tct gta gca aac aat aac aaa      739
Asp Leu Leu Gln Ala Ala Leu Leu Gln Ser Val Ala Asn Asn Asn Lys
            200             205             210 gca gct gag ctt ctt aaa gag atg caa gat aac cca gta gtc cca ggg      787
Ala Ala Glu Leu Leu Lys Glu Met Gln Asp Asn Pro Val Val Pro Gly
    215             220             225 aaa acg cct gca att gct caa tct tta gtt gat cag aca gat gct aca      835
Lys Thr Pro Ala Ile Ala Gln Ser Leu Val Asp Gln Thr Asp Ala Thr
230             235             240             245 gcg aca cag ata gag aaa gat gga aat gcg att agg gat gca tat ttt      883
Ala Thr Gln Ile Glu Lys Asp Gly Asn Ala Ile Arg Asp Ala Tyr Phe
                250             255             260 gca gga cag aac gct agt gga gct gta gaa aat gct aaa tct aat aac      931
Ala Gly Gln Asn Ala Ser Gly Ala Val Glu Asn Ala Lys Ser Asn Asn
                265             270             275 agt ata agc aac ata gat tca gct aaa gca gca atc gct act gct aag      979
Ser Ile Ser Asn Ile Asp Ser Ala Lys Ala Ala Ile Ala Thr Ala Lys
            280             285             290 aca caa ata gct gaa gct cag aaa aag ttc ccc gac tct cca att ctt     1027
Thr Gln Ile Ala Glu Ala Gln Lys Lys Phe Pro Asp Ser Pro Ile Leu
    295             300             305 caa gaa gcg gaa caa atg gta ata cag gct gag aaa gat ctt aaa aat     1075
Gln Glu Ala Glu Gln Met Val Ile Gln Ala Glu Lys Asp Leu Lys Asn
310             315             320             325 atc aaa cct gca gat ggt tct gat gtt cca aat cca gga act aca gtt     1123
Ile Lys Pro Ala Asp Gly Ser Asp Val Pro Asn Pro Gly Thr Thr Val
                330             335             340 gga ggc tcc aag caa caa gga agt agt att ggt agt att cgt gtt tcc     1171
Gly Gly Ser Lys Gln Gln Gly Ser Ser Ile Gly Ser Ile Arg Val Ser
                345             350             355 atg ctg tta gat gat gct gaa aat gag acc gct tcc att ttg atg tct     1219
Met Leu Leu Asp Asp Ala Glu Asn Glu Thr Ala Ser Ile Leu Met Ser
            360             365             370 ggg ttt cgt cag atg att cac atg ttc aat acg gaa aat cct gat tct     1267
Gly Phe Arg Gln Met Ile His Met Phe Asn Thr Glu Asn Pro Asp Ser
    375             380             385
```

```
caa gct gcc caa cag gag ctc gca gca caa gct aga gca gcg aaa gcc     1315
Gln Ala Ala Gln Gln Glu Leu Ala Ala Gln Ala Arg Ala Ala Lys Ala
390                 395                 400                 405 gct gga gat gac agt gct gct gca gcg ctg gca gat gct cag aaa gct     1363
Ala Gly Asp Asp Ser Ala Ala Ala Ala Leu Ala Asp Ala Gln Lys Ala
            410                 415                 420 tta gaa gcg gct cta ggt aaa gct ggg caa caa cag ggc ata ctc aat     1411
Leu Glu Ala Ala Leu Gly Lys Ala Gly Gln Gln Gln Gly Ile Leu Asn
        425                 430                 435 gct tta gga cag atc gct tct gct gct gtt gtg agc gca gga gtt cct     1459
Ala Leu Gly Gln Ile Ala Ser Ala Ala Val Val Ser Ala Gly Val Pro
440                 445                 450 ccc gct gca gca agt tct ata ggg tca tct gta aaa cag ctt tac aag     1507
Pro Ala Ala Ala Ser Ser Ile Gly Ser Ser Val Lys Gln Leu Tyr Lys
    455                 460                 465 acc tca aaa tct aca ggt tct gat tat aaa aca cag ata tca gca ggt     1555
Thr Ser Lys Ser Thr Gly Ser Asp Tyr Lys Thr Gln Ile Ser Ala Gly
470                 475                 480                 485 tat gat gct tac aaa tcc atc aat gat gcc tat ggt agg gca cga aat     1603
Tyr Asp Ala Tyr Lys Ser Ile Asn Asp Ala Tyr Gly Arg Ala Arg Asn
                490                 495                 500 gat gcg act cgt gat gtg ata aac aat gta agt acc ccc gct ctc aca     1651
Asp Ala Thr Arg Asp Val Ile Asn Asn Val Ser Thr Pro Ala Leu Thr
            505                 510                 515 cga tcc gtt cct aga gca cga aca gaa gct cga gga cca gaa aaa aca     1699
Arg Ser Val Pro Arg Ala Arg Thr Glu Ala Arg Gly Pro Glu Lys Thr
        520                 525                 530 gat caa gcc ctc gct agg gtg att tct ggc aat agc aga act ctt gga     1747
Asp Gln Ala Leu Ala Arg Val Ile Ser Gly Asn Ser Arg Thr Leu Gly
535                 540                 545 gat gtc tat agt caa gtt tcg gca cta caa tct gta atg cag atc atc     1795
Asp Val Tyr Ser Gln Val Ser Ala Leu Gln Ser Val Met Gln Ile Ile
550                 555                 560                 565 cag tcg aat cct caa gcg aat aat gag gag atc aga caa aag ctt aca     1843
Gln Ser Asn Pro Gln Ala Asn Asn Glu Glu Ile Arg Gln Lys Leu Thr
                570                 575                 580 tcg gca gtg aca aag cct cca cag ttt ggc tat cct tat gtg caa ctt     1891
Ser Ala Val Thr Lys Pro Pro Gln Phe Gly Tyr Pro Tyr Val Gln Leu
            585                 590                 595 tct aat gac tct aca cag aag ttc ata gct aaa tta gaa agt ttg ttt     1939
Ser Asn Asp Ser Thr Gln Lys Phe Ile Ala Lys Leu Glu Ser Leu Phe
        600                 605                 610 gct gaa gga tct agg aca gca gct gaa ata aaa gca ctt tcc ttt gaa     1987
Ala Glu Gly Ser Arg Thr Ala Ala Glu Ile Lys Ala Leu Ser Phe Glu
615                 620                 625 acg aac tcc ttg ttt att cag cag gtg ctg gtc aat atc ggc tct cta     2035
Thr Asn Ser Leu Phe Ile Gln Gln Val Leu Val Asn Ile Gly Ser Leu
630                 635                 640                 645 tat tct ggt tat ctc caa taacaacacc taagtgttcg tttggagaga            2083
Tyr Ser Gly Tyr Leu Gln
                650 ttattatgtg ctttggtaag gcctttgttg aggccttacc aacacactag aacgatcttc   2143 aataaataaa aga                                                      2156

<210> SEQ ID NO 2
<211> LENGTH: 651
<212> TYPE: PRT
<213> ORGANISM: Chlamydia pneumoniae

<400> SEQUENCE: 2
```

```
Met Val Asn Pro Ile Gly Pro Gly Pro Ile Asp Glu Thr Glu Arg Thr
 1               5                  10                  15
Pro Pro Ala Asp Leu Ser Ala Gln Gly Leu Glu Ala Ser Ala Ala Asn
             20                  25                  30
Lys Ser Ala Glu Ala Gln Arg Ile Ala Gly Ala Glu Ala Lys Pro Lys
         35                  40                  45
Glu Ser Lys Thr Asp Ser Val Glu Arg Trp Ser Ile Leu Arg Ser Ala
     50                  55                  60
Val Asn Ala Leu Met Ser Leu Ala Asp Lys Leu Gly Ile Ala Ser Ser
 65                  70                  75                  80
Asn Ser Ser Ser Thr Ser Arg Ser Ala Asp Val Asp Ser Thr Thr
                 85                  90                  95
Ala Thr Ala Pro Thr Pro Pro Pro Thr Phe Asp Asp Tyr Lys Thr
             100                 105                 110
Gln Ala Gln Thr Ala Tyr Asp Thr Ile Phe Thr Ser Thr Ser Leu Ala
             115                 120                 125
Asp Ile Gln Ala Ala Leu Val Ser Leu Gln Asp Ala Val Thr Asn Ile
 130                 135                 140
Lys Asp Thr Ala Ala Thr Asp Glu Glu Thr Ala Ile Ala Ala Glu Trp
145                 150                 155                 160
Glu Thr Lys Asn Ala Asp Ala Val Lys Val Gly Ala Gln Ile Thr Glu
                 165                 170                 175
Leu Ala Lys Tyr Ala Ser Asp Asn Gln Ala Ile Leu Asp Ser Leu Gly
             180                 185                 190
Lys Leu Thr Ser Phe Asp Leu Leu Gln Ala Ala Leu Leu Gln Ser Val
             195                 200                 205
Ala Asn Asn Asn Lys Ala Ala Glu Leu Leu Lys Glu Met Gln Asp Asn
 210                 215                 220
Pro Val Pro Gly Lys Thr Pro Ala Ile Ala Gln Ser Leu Val Asp
225                 230                 235                 240
Gln Thr Asp Ala Thr Ala Thr Gln Ile Glu Lys Asp Gly Asn Ala Ile
             245                 250                 255
Arg Asp Ala Tyr Phe Ala Gly Gln Asn Ala Ser Gly Ala Val Glu Asn
             260                 265                 270
Ala Lys Ser Asn Asn Ser Ile Ser Asn Ile Asp Ser Ala Lys Ala Ala
             275                 280                 285
Ile Ala Thr Ala Lys Thr Gln Ile Ala Glu Ala Gln Lys Lys Phe Pro
 290                 295                 300
Asp Ser Pro Ile Leu Gln Glu Ala Glu Gln Met Val Ile Gln Ala Glu
305                 310                 315                 320
Lys Asp Leu Lys Asn Ile Lys Pro Ala Asp Gly Ser Asp Val Pro Asn
             325                 330                 335
Pro Gly Thr Thr Val Gly Gly Ser Lys Gln Gln Gly Ser Ser Ile Gly
             340                 345                 350
Ser Ile Arg Val Ser Met Leu Leu Asp Asp Ala Glu Asn Glu Thr Ala
             355                 360                 365
Ser Ile Leu Met Ser Gly Phe Arg Gln Met Ile His Met Phe Asn Thr
 370                 375                 380
Glu Asn Pro Asp Ser Gln Ala Ala Gln Gln Leu Ala Ala Gln Ala
385                 390                 395                 400
Arg Ala Ala Lys Ala Ala Gly Asp Asp Ser Ala Ala Ala Leu Ala
             405                 410                 415
```

```
Asp Ala Gln Lys Ala Leu Glu Ala Ala Leu Gly Lys Ala Gly Gln Gln
                420                 425                 430

Gln Gly Ile Leu Asn Ala Leu Gly Gln Ile Ala Ser Ala Ala Val Val
            435                 440                 445

Ser Ala Gly Val Pro Ala Ala Ser Ser Ile Gly Ser Ser Val
        450                 455                 460

Lys Gln Leu Tyr Lys Thr Ser Lys Ser Thr Gly Ser Asp Tyr Lys Thr
465                 470                 475                 480

Gln Ile Ser Ala Gly Tyr Asp Ala Tyr Lys Ser Ile Asn Asp Ala Tyr
                485                 490                 495

Gly Arg Ala Arg Asn Asp Ala Thr Arg Asp Val Ile Asn Asn Val Ser
            500                 505                 510

Thr Pro Ala Leu Thr Arg Ser Val Pro Arg Ala Arg Thr Glu Ala Arg
        515                 520                 525

Gly Pro Glu Lys Thr Asp Gln Ala Leu Ala Arg Val Ile Ser Gly Asn
    530                 535                 540

Ser Arg Thr Leu Gly Asp Val Tyr Ser Gln Val Ser Ala Leu Gln Ser
545                 550                 555                 560

Val Met Gln Ile Ile Gln Ser Asn Pro Gln Ala Asn Asn Glu Glu Ile
                565                 570                 575

Arg Gln Lys Leu Thr Ser Ala Val Thr Lys Pro Pro Gln Phe Gly Tyr
            580                 585                 590

Pro Tyr Val Gln Leu Ser Asn Asp Ser Thr Gln Lys Phe Ile Ala Lys
        595                 600                 605

Leu Glu Ser Leu Phe Ala Glu Gly Ser Arg Thr Ala Ala Glu Ile Lys
    610                 615                 620

Ala Leu Ser Phe Glu Thr Asn Ser Leu Phe Ile Gln Gln Val Leu Val
625                 630                 635                 640

Asn Ile Gly Ser Leu Tyr Ser Gly Tyr Leu Gln
                645                 650

<210> SEQ ID NO 3
<211> LENGTH: 1852
<212> TYPE: DNA
<213> ORGANISM: Chlamydia pneumoniae
<220> FEATURE:
<221> NAME/KEY: CDS
<222> LOCATION: (1)..(1749)

<400> SEQUENCE: 3 atg agt ctg gca gat aag ctg ggt att gct tct agt aac agc tcg tct      48
Met Ser Leu Ala Asp Lys Leu Gly Ile Ala Ser Ser Asn Ser Ser Ser
1               5                   10                  15 tct act agc aga tct gca gac gtg gac tca acg aca gcg acc gca cct      96
Ser Thr Ser Arg Ser Ala Asp Val Asp Ser Thr Thr Ala Thr Ala Pro
                20                  25                  30 acg cct cct cca ccc acg ttt gat gat tat aag act caa gcg caa aca     144
Thr Pro Pro Pro Pro Thr Phe Asp Asp Tyr Lys Thr Gln Ala Gln Thr
            35                  40                  45 gct tac gat act atc ttt acc tca aca tca cta gct gac ata cag gct     192
Ala Tyr Asp Thr Ile Phe Thr Ser Thr Ser Leu Ala Asp Ile Gln Ala
    50                  55                  60 gct ttg gtg agc ctc cag gat gct gtc act aat ata aag gat aca gcg     240
Ala Leu Val Ser Leu Gln Asp Ala Val Thr Asn Ile Lys Asp Thr Ala
65                  70                  75                  80 gct act gat gag gaa acc gca atc gct gcg gag tgg gaa act aag aat     288
Ala Thr Asp Glu Glu Thr Ala Ile Ala Ala Glu Trp Glu Thr Lys Asn
                85                  90                  95
```

| | | |
|---|---|---|
| gcc gat gca gtt aaa gtt ggc gcg caa att aca gaa tta gcg aaa tat<br>Ala Asp Ala Val Lys Val Gly Ala Gln Ile Thr Glu Leu Ala Lys Tyr<br>100 105 110 | | 336 |
| gct tcg gat aac caa gcg att ctt gac tct tta ggt aaa ctg act tcc<br>Ala Ser Asp Asn Gln Ala Ile Leu Asp Ser Leu Gly Lys Leu Thr Ser<br>115 120 125 | | 384 |
| ttc gac ctc tta cag gct gct ctt ctc caa tct gta gca aac aat aac<br>Phe Asp Leu Leu Gln Ala Ala Leu Leu Gln Ser Val Ala Asn Asn Asn<br>130 135 140 | | 432 |
| aaa gca gct gag ctt ctt aaa gag atg caa gat aac cca gta gtc cca<br>Lys Ala Ala Glu Leu Leu Lys Glu Met Gln Asp Asn Pro Val Val Pro<br>145 150 155 160 | | 480 |
| ggg aaa acg cct gca att gct caa tct tta gtt gat cag aca gat gct<br>Gly Lys Thr Pro Ala Ile Ala Gln Ser Leu Val Asp Gln Thr Asp Ala<br>165 170 175 | | 528 |
| aca gcg aca cag ata gag aaa gat gga aat gcg att agg gat gca tat<br>Thr Ala Thr Gln Ile Glu Lys Asp Gly Asn Ala Ile Arg Asp Ala Tyr<br>180 185 190 | | 576 |
| ttt gca gga cag aac gct agt gga gct gta gaa aat gct aaa tct aat<br>Phe Ala Gly Gln Asn Ala Ser Gly Ala Val Glu Asn Ala Lys Ser Asn<br>195 200 205 | | 624 |
| aac agt ata agc aac ata gat tca gct aaa gca gca atc gct act gct<br>Asn Ser Ile Ser Asn Ile Asp Ser Ala Lys Ala Ala Ile Ala Thr Ala<br>210 215 220 | | 672 |
| aag aca caa ata gct gaa gct cag aaa aag ttc ccc gac tct cca att<br>Lys Thr Gln Ile Ala Glu Ala Gln Lys Lys Phe Pro Asp Ser Pro Ile<br>225 230 235 240 | | 720 |
| ctt caa gaa gcg gaa caa atg gta ata cag gct gag aaa gat ctt aaa<br>Leu Gln Glu Ala Glu Gln Met Val Ile Gln Ala Glu Lys Asp Leu Lys<br>245 250 255 | | 768 |
| aat atc aaa cct gca gat ggt tct gat gtt cca aat cca gga act aca<br>Asn Ile Lys Pro Ala Asp Gly Ser Asp Val Pro Asn Pro Gly Thr Thr<br>260 265 270 | | 816 |
| gtt gga ggc tcc aag caa caa gga agt agt att ggt agt att cgt gtt<br>Val Gly Gly Ser Lys Gln Gln Gly Ser Ser Ile Gly Ser Ile Arg Val<br>275 280 285 | | 864 |
| tcc atg ctg tta gat gat gct gaa aat gag acc gct tcc att ttg atg<br>Ser Met Leu Leu Asp Asp Ala Glu Asn Glu Thr Ala Ser Ile Leu Met<br>290 295 300 | | 912 |
| tct ggg ttt cgt cag atg att cac atg ttc aat acg gaa aat cct gat<br>Ser Gly Phe Arg Gln Met Ile His Met Phe Asn Thr Glu Asn Pro Asp<br>305 310 315 320 | | 960 |
| tct caa gct gcc caa cag gag ctc gca gca caa gct aga gca gcg aaa<br>Ser Gln Ala Ala Gln Gln Glu Leu Ala Ala Gln Ala Arg Ala Ala Lys<br>325 330 335 | | 1008 |
| gcc gct gga gat gac agt gct gct gca gcg ctg gca gat gct cag aaa<br>Ala Ala Gly Asp Asp Ser Ala Ala Ala Ala Leu Ala Asp Ala Gln Lys<br>340 345 350 | | 1056 |
| gct tta gaa gcg gct cta ggt aaa gct ggg caa caa cag ggc ata ctc<br>Ala Leu Glu Ala Ala Leu Gly Lys Ala Gly Gln Gln Gln Gly Ile Leu<br>355 360 365 | | 1104 |
| aat gct tta gga cag atc gct tct gct gct gtt gtg agc gca gga gtt<br>Asn Ala Leu Gly Gln Ile Ala Ser Ala Ala Val Val Ser Ala Gly Val<br>370 375 380 | | 1152 |
| cct ccc gct gca gca agt tct ata ggg tca tct gta aaa cag ctt tac<br>Pro Pro Ala Ala Ala Ser Ser Ile Gly Ser Ser Val Lys Gln Leu Tyr<br>385 390 395 400 | | 1200 |
| aag acc tca aaa tct aca ggt tct gat tat aaa aca cag ata tca gca<br>Lys Thr Ser Lys Ser Thr Gly Ser Asp Tyr Lys Thr Gln Ile Ser Ala | | 1248 |

```
                     405                 410                 415
ggt tat gat gct tac aaa tcc atc aat gat gcc tat ggt agg gca cga        1296
Gly Tyr Asp Ala Tyr Lys Ser Ile Asn Asp Ala Tyr Gly Arg Ala Arg
            420                 425                 430 aat gat gcg act cgt gat gtg ata aac aat gta agt acc ccc gct ctc        1344
Asn Asp Ala Thr Arg Asp Val Ile Asn Asn Val Ser Thr Pro Ala Leu
            435                 440                 445 aca cga tcc gtt cct aga gca cga aca gaa gct cga gga cca gaa aaa        1392
Thr Arg Ser Val Pro Arg Ala Arg Thr Glu Ala Arg Gly Pro Glu Lys
        450                 455                 460 aca gat caa gcc ctc gct agg gtg att tct ggc aat agc aga act ctt        1440
Thr Asp Gln Ala Leu Ala Arg Val Ile Ser Gly Asn Ser Arg Thr Leu
465                 470                 475                 480 gga gat gtc tat agt caa gtt tcg gca cta caa tct gta atg cag atc        1488
Gly Asp Val Tyr Ser Gln Val Ser Ala Leu Gln Ser Val Met Gln Ile
                485                 490                 495 act cag tcg aat cct caa gcg aat aat gag gag atc aga caa aag ctt        1536
Thr Gln Ser Asn Pro Gln Ala Asn Asn Glu Glu Ile Arg Gln Lys Leu
            500                 505                 510 aca tcg gca gtg aca aag cct cca cag ttt ggc tat cct tat gtg caa        1584
Thr Ser Ala Val Thr Lys Pro Pro Gln Phe Gly Tyr Pro Tyr Val Gln
        515                 520                 525 ctt tct aat gac tct aca cag aag ttc ata gct aaa tta gaa agt ttg        1632
Leu Ser Asn Asp Ser Thr Gln Lys Phe Ile Ala Lys Leu Glu Ser Leu
    530                 535                 540 ttt gct gaa gga tct agg aca gca gct gaa ata aaa gca ctt tcc ttt        1680
Phe Ala Glu Gly Ser Arg Thr Ala Ala Glu Ile Lys Ala Leu Ser Phe
545                 550                 555                 560 gaa acg aac tcc ttg ttt att cag cag gtg ctg gtc aat atc ggc tct        1728
Glu Thr Asn Ser Leu Phe Ile Gln Gln Val Leu Val Asn Ile Gly Ser
                565                 570                 575 cta tat tct ggt tat ctc caa taacaacacc taagtgttcg tttggagaga          1779
Leu Tyr Ser Gly Tyr Leu Gln
            580 ttattatgtg ctttggtaag gcctttgttg aggccttacc aacacactag aacgatcttc     1839 aataaataaa aga                                                         1852

<210> SEQ ID NO 4
<211> LENGTH: 583
<212> TYPE: PRT
<213> ORGANISM: Chlamydia pneumoniae

<400> SEQUENCE: 4

Met Ser Leu Ala Asp Lys Leu Gly Ile Ala Ser Ser Asn Ser Ser Ser
  1               5                  10                  15

Ser Thr Ser Arg Ser Ala Asp Val Asp Ser Thr Thr Ala Thr Ala Pro
                 20                  25                  30

Thr Pro Pro Pro Thr Phe Asp Asp Tyr Lys Thr Gln Ala Gln Thr
             35                  40                  45

Ala Tyr Asp Thr Ile Phe Thr Ser Thr Leu Ala Asp Ile Gln Ala
         50                  55                  60

Ala Leu Val Ser Leu Gln Asp Ala Val Thr Asn Ile Lys Asp Thr Ala
 65                  70                  75                  80

Ala Thr Asp Glu Glu Thr Ala Ile Ala Ala Glu Trp Glu Thr Lys Asn
                 85                  90                  95

Ala Asp Ala Val Lys Val Gly Ala Gln Ile Thr Glu Leu Ala Lys Tyr
            100                 105                 110
```

```
Ala Ser Asp Asn Gln Ala Ile Leu Asp Ser Leu Gly Lys Leu Thr Ser
        115                 120                 125

Phe Asp Leu Leu Gln Ala Ala Leu Leu Gln Ser Val Ala Asn Asn Asn
130                 135                 140

Lys Ala Ala Glu Leu Leu Lys Glu Met Gln Asp Asn Pro Val Val Pro
145                 150                 155                 160

Gly Lys Thr Pro Ala Ile Ala Gln Ser Leu Val Asp Gln Thr Asp Ala
                165                 170                 175

Thr Ala Thr Gln Ile Glu Lys Asp Gly Asn Ala Ile Arg Asp Ala Tyr
            180                 185                 190

Phe Ala Gly Gln Asn Ala Ser Gly Ala Val Glu Asn Ala Lys Ser Asn
        195                 200                 205

Asn Ser Ile Ser Asn Ile Asp Ser Ala Lys Ala Ile Ala Thr Ala
210                 215                 220

Lys Thr Gln Ile Ala Glu Ala Gln Lys Lys Phe Pro Asp Ser Pro Ile
225                 230                 235                 240

Leu Gln Glu Ala Glu Gln Met Val Ile Gln Ala Glu Lys Asp Leu Lys
                245                 250                 255

Asn Ile Lys Pro Ala Asp Gly Ser Asp Val Pro Asn Pro Gly Thr Thr
                260                 265                 270

Val Gly Gly Ser Lys Gln Gln Gly Ser Ser Ile Gly Ser Ile Arg Val
        275                 280                 285

Ser Met Leu Leu Asp Asp Ala Glu Asn Glu Thr Ala Ser Ile Leu Met
        290                 295                 300

Ser Gly Phe Arg Gln Met Ile His Met Phe Asn Thr Glu Asn Pro Asp
305                 310                 315                 320

Ser Gln Ala Ala Gln Gln Glu Leu Ala Ala Gln Ala Arg Ala Ala Lys
                325                 330                 335

Ala Ala Gly Asp Asp Ser Ala Ala Ala Leu Ala Asp Ala Gln Lys
                340                 345                 350

Ala Leu Glu Ala Ala Leu Gly Lys Ala Gly Gln Gln Gln Gly Ile Leu
            355                 360                 365

Asn Ala Leu Gly Gln Ile Ala Ser Ala Ala Val Val Ser Ala Gly Val
        370                 375                 380

Pro Pro Ala Ala Ala Ser Ser Ile Gly Ser Ser Val Lys Gln Leu Tyr
385                 390                 395                 400

Lys Thr Ser Lys Ser Thr Gly Ser Asp Tyr Lys Thr Gln Ile Ser Ala
                405                 410                 415

Gly Tyr Asp Ala Tyr Lys Ser Ile Asn Asp Ala Tyr Gly Arg Ala Arg
                420                 425                 430

Asn Asp Ala Thr Arg Asp Val Ile Asn Asn Val Ser Thr Pro Ala Leu
            435                 440                 445

Thr Arg Ser Val Pro Arg Ala Arg Thr Glu Ala Arg Gly Pro Glu Lys
450                 455                 460

Thr Asp Gln Ala Leu Ala Arg Val Ile Ser Gly Asn Ser Arg Thr Leu
465                 470                 475                 480

Gly Asp Val Tyr Ser Gln Val Ser Ala Leu Gln Ser Val Met Gln Ile
                485                 490                 495

Thr Gln Ser Asn Pro Gln Ala Asn Asn Glu Glu Ile Arg Gln Lys Leu
            500                 505                 510

Thr Ser Ala Val Thr Lys Pro Pro Gln Phe Gly Tyr Pro Tyr Val Gln
        515                 520                 525

Leu Ser Asn Asp Ser Thr Gln Lys Phe Ile Ala Lys Leu Glu Ser Leu
```

-continued

```
                    530                 535                 540
Phe Ala Glu Gly Ser Arg Thr Ala Ala Glu Ile Lys Ala Leu Ser Phe
545                 550                 555                 560

Glu Thr Asn Ser Leu Phe Ile Gln Gln Val Leu Val Asn Ile Gly Ser
                565                 570                 575

Leu Tyr Ser Gly Tyr Leu Gln
            580

<210> SEQ ID NO 5
<211> LENGTH: 1456
<212> TYPE: DNA
<213> ORGANISM: Chlamydia pneumoniae
<220> FEATURE:
<221> NAME/KEY: CDS
<222> LOCATION: (101)..(1456)

<400> SEQUENCE: 5 ataaatctt taaaaacagg ctcgcattaa ttattagtga gagcttttt tttatttttt        60 ataataaaac taaaagattt ttattatttt ttgagttttt atg gtt aat cct att       115
                                             Met Val Asn Pro Ile
                                              1               5 ggt cca ggt cct ata gac gaa aca gaa cgc aca cct ccc gca gat ctt       163
Gly Pro Gly Pro Ile Asp Glu Thr Glu Arg Thr Pro Pro Ala Asp Leu
             10                  15                  20 tct gct caa gga ttg gag gcg agt gca gca aat aag agt gcg gaa gct       211
Ser Ala Gln Gly Leu Glu Ala Ser Ala Ala Asn Lys Ser Ala Glu Ala
         25                  30                  35 caa aga ata gca ggt gcg gaa gct aag cct aaa gaa tct aag acc gat       259
Gln Arg Ile Ala Gly Ala Glu Ala Lys Pro Lys Glu Ser Lys Thr Asp
     40                  45                  50 tct gta gag cga tgg agc atc ttg cgt tct gca gtg aat gct ctc atg       307
Ser Val Glu Arg Trp Ser Ile Leu Arg Ser Ala Val Asn Ala Leu Met
 55                  60                  65 agt ctg gca gat aag ctg ggt att gct tct agt aac agc tcg tct tct       355
Ser Leu Ala Asp Lys Leu Gly Ile Ala Ser Ser Asn Ser Ser Ser Ser
 70                  75                  80                  85 act agc aga tct gca gac gtg gac tca acg aca gcg acc gca cct acg       403
Thr Ser Arg Ser Ala Asp Val Asp Ser Thr Thr Ala Thr Ala Pro Thr
                 90                  95                 100 cct cct cca ccc acg ttt gat gat tat aag act caa gcg caa aca gct       451
Pro Pro Pro Pro Thr Phe Asp Asp Tyr Lys Thr Gln Ala Gln Thr Ala
             105                 110                 115 tac gat act atc ttt acc tca aca tca cta gct gac ata cag gct gct       499
Tyr Asp Thr Ile Phe Thr Ser Thr Ser Leu Ala Asp Ile Gln Ala Ala
         120                 125                 130 ttg gtg agc ctc cag gat gct gtc act aat ata aag gat aca gcg gct       547
Leu Val Ser Leu Gln Asp Ala Val Thr Asn Ile Lys Asp Thr Ala Ala
135                 140                 145 act gat gag gaa acc gca atc gct gcg gag tgg gaa act aag aat gcc       595
Thr Asp Glu Glu Thr Ala Ile Ala Ala Glu Trp Glu Thr Lys Asn Ala
150                 155                 160                 165 gat gca gtt aaa gtt ggc gcg caa att aca gaa tta gcg aaa tat gct       643
Asp Ala Val Lys Val Gly Ala Gln Ile Thr Glu Leu Ala Lys Tyr Ala
                170                 175                 180 tcg gat aac caa gcg att ctt gac tct tta ggt aaa ctg act tcc ttc       691
Ser Asp Asn Gln Ala Ile Leu Asp Ser Leu Gly Lys Leu Thr Ser Phe
            185                 190                 195 gac ctc tta cag gct gct ctt ctc caa tct gta gca aac aat aac aaa       739
Asp Leu Leu Gln Ala Ala Leu Leu Gln Ser Val Ala Asn Asn Asn Lys
        200                 205                 210
```

```
gca gct gag ctt ctt aaa gag atg caa gat aac cca gta gtc cca ggg      787
Ala Ala Glu Leu Leu Lys Glu Met Gln Asp Asn Pro Val Val Pro Gly
    215                 220                 225 aaa acg cct gca att gct caa tct tta gtt gat cag aca gat gct aca      835
Lys Thr Pro Ala Ile Ala Gln Ser Leu Val Asp Gln Thr Asp Ala Thr
230                 235                 240                 245 gcg aca cag ata gag aaa gat gga aat gcg att agg gat gca tat ttt      883
Ala Thr Gln Ile Glu Lys Asp Gly Asn Ala Ile Arg Asp Ala Tyr Phe
                250                 255                 260 gca gga cag aac gct agt gga gct gta gaa aat gct aaa tct aat aac      931
Ala Gly Gln Asn Ala Ser Gly Ala Val Glu Asn Ala Lys Ser Asn Asn
            265                 270                 275 agt ata agc aac ata gat tca gct aaa gca gca atc gct act gct aag      979
Ser Ile Ser Asn Ile Asp Ser Ala Lys Ala Ala Ile Ala Thr Ala Lys
        280                 285                 290 aca caa ata gct gaa gct cag aaa aag ttc ccc gac tct cca att ctt     1027
Thr Gln Ile Ala Glu Ala Gln Lys Lys Phe Pro Asp Ser Pro Ile Leu
    295                 300                 305 caa gaa gcg gaa caa atg gta ata cag gct gag aaa gat ctt aaa aat     1075
Gln Glu Ala Glu Gln Met Val Ile Gln Ala Glu Lys Asp Leu Lys Asn
310                 315                 320                 325 atc aaa cct gca gat ggt tct gat gtt cca aat cca gga act aca gtt     1123
Ile Lys Pro Ala Asp Gly Ser Asp Val Pro Asn Pro Gly Thr Thr Val
                330                 335                 340 gga ggc tcc aag caa caa gga agt agt att ggt agt att cgt gtt tcc     1171
Gly Gly Ser Lys Gln Gln Gly Ser Ser Ile Gly Ser Ile Arg Val Ser
            345                 350                 355 atg ctg tta gat gat gct gaa aat gag acc gct tcc att ttg atg tct     1219
Met Leu Leu Asp Asp Ala Glu Asn Glu Thr Ala Ser Ile Leu Met Ser
        360                 365                 370 ggg ttt cgt cag atg att cac atg ttc aat acg gaa aat cct gat tct     1267
Gly Phe Arg Gln Met Ile His Met Phe Asn Thr Glu Asn Pro Asp Ser
    375                 380                 385 caa gct gcc caa cag gag ctc gca gca caa gct aga gca gcg aaa gcc     1315
Gln Ala Ala Gln Gln Glu Leu Ala Ala Gln Ala Arg Ala Ala Lys Ala
390                 395                 400                 405 gct gga gat gac agt gct gct gca gcg ctg gca gat gct cag aaa gct     1363
Ala Gly Asp Asp Ser Ala Ala Ala Ala Leu Ala Asp Ala Gln Lys Ala
                410                 415                 420 tta gaa gcg gct cta ggt aaa gct ggg caa caa cag ggc ata ctc aat     1411
Leu Glu Ala Ala Leu Gly Lys Ala Gly Gln Gln Gln Gly Ile Leu Asn
            425                 430                 435 gct tta gga cag atc gct tct gct gct gtt gtg agc gca gga gta         1456
Ala Leu Gly Gln Ile Ala Ser Ala Ala Val Val Ser Ala Gly Val
        440                 445                 450

<210> SEQ ID NO 6
<211> LENGTH: 452
<212> TYPE: PRT
<213> ORGANISM: Chlamydia pneumoniae

<400> SEQUENCE: 6

Met Val Asn Pro Ile Gly Pro Gly Pro Ile Asp Glu Thr Glu Arg Thr
 1               5                  10                  15

Pro Pro Ala Asp Leu Ser Ala Gln Gly Leu Glu Ala Ser Ala Ala Asn
            20                  25                  30

Lys Ser Ala Glu Ala Gln Arg Ile Ala Gly Ala Glu Ala Lys Pro Lys
        35                  40                  45

Glu Ser Lys Thr Asp Ser Val Glu Arg Trp Ser Ile Leu Arg Ser Ala
```

```
            50                  55                  60
Val Asn Ala Leu Met Ser Leu Ala Asp Lys Leu Gly Ile Ala Ser Ser
 65                  70                  75                  80

Asn Ser Ser Ser Thr Ser Arg Ser Ala Asp Val Asp Ser Thr Thr
                 85                  90                  95

Ala Thr Ala Pro Thr Pro Pro Pro Thr Phe Asp Asp Tyr Lys Thr
            100                 105                 110

Gln Ala Gln Thr Ala Tyr Asp Thr Ile Phe Thr Ser Thr Ser Leu Ala
            115                 120                 125

Asp Ile Gln Ala Ala Leu Val Ser Leu Gln Asp Ala Val Thr Asn Ile
130                 135                 140

Lys Asp Thr Ala Ala Thr Asp Glu Glu Thr Ala Ile Ala Ala Glu Trp
145                 150                 155                 160

Glu Thr Lys Asn Ala Asp Ala Val Lys Val Gly Ala Gln Ile Thr Glu
                165                 170                 175

Leu Ala Lys Tyr Ala Ser Asp Asn Gln Ala Ile Leu Asp Ser Leu Gly
            180                 185                 190

Lys Leu Thr Ser Phe Asp Leu Leu Gln Ala Ala Leu Leu Gln Ser Val
            195                 200                 205

Ala Asn Asn Lys Ala Ala Glu Leu Leu Lys Glu Met Gln Asp Asn
210                 215                 220

Pro Val Val Pro Gly Lys Thr Pro Ala Ile Ala Gln Ser Leu Val Asp
225                 230                 235                 240

Gln Thr Asp Ala Thr Ala Thr Gln Ile Glu Lys Asp Gly Asn Ala Ile
            245                 250                 255

Arg Asp Ala Tyr Phe Ala Gly Gln Asn Ala Ser Gly Ala Val Glu Asn
            260                 265                 270

Ala Lys Ser Asn Asn Ser Ile Ser Asn Ile Asp Ser Ala Lys Ala Ala
            275                 280                 285

Ile Ala Thr Ala Lys Thr Gln Ile Ala Glu Ala Gln Lys Lys Phe Pro
290                 295                 300

Asp Ser Pro Ile Leu Gln Glu Ala Glu Gln Met Val Ile Gln Ala Glu
305                 310                 315                 320

Lys Asp Leu Lys Asn Ile Lys Pro Ala Asp Gly Ser Asp Val Pro Asn
                325                 330                 335

Pro Gly Thr Thr Val Gly Gly Ser Lys Gln Gln Gly Ser Ser Ile Gly
            340                 345                 350

Ser Ile Arg Val Ser Met Leu Leu Asp Asp Ala Glu Asn Glu Thr Ala
            355                 360                 365

Ser Ile Leu Met Ser Gly Phe Arg Gln Met Ile His Met Phe Asn Thr
            370                 375                 380

Glu Asn Pro Asp Ser Gln Ala Ala Gln Glu Leu Ala Ala Gln Ala
385                 390                 395                 400

Arg Ala Ala Lys Ala Ala Gly Asp Asp Ser Ala Ala Ala Leu Ala
                405                 410                 415

Asp Ala Gln Lys Ala Leu Glu Ala Ala Leu Gly Lys Ala Gly Gln Gln
            420                 425                 430

Gln Gly Ile Leu Asn Ala Leu Gly Gln Ile Ala Ser Ala Ala Val Val
            435                 440                 445

Ser Ala Gly Val
        450
```

<210> SEQ ID NO 7

```
<211> LENGTH: 2238
<212> TYPE: DNA
<213> ORGANISM: Chlamydia pneumoniae
<220> FEATURE:
<221> NAME/KEY: CDS
<222> LOCATION: (766)..(2235)

<400> SEQUENCE: 7
```

| | |
|---|---:|
| atgacaaaaa aacattatgc ttgggttgta aagggattc tcaatcgttt gcctaaacag | 60 |
| ttttttgtga aatgtagtgt tgtcgactgg aacacattcg ttccttcaga aacctccact | 120 |
| acagaaaaag ctgctacaaa cgctatgaaa tacaaatact gtgtttggca gtggctcgtc | 180 |
| ggaaagcata gtcaggttcc ttggatcaat ggacagaaaa agcctctata tctttatgga | 240 |
| gctttcttaa tgaacccttt agcaaaggct acgaagacta cgttaaatgg aaaagaaaac | 300 |
| ctagcttggt ttattggagg aactttaggg ggactcagaa aagctggaga ctggtctgcc | 360 |
| acagtacgtt atgagtatgt cgaagccttg tcggttccag aaatagatgt ttcagggatt | 420 |
| ggccgtggta atttattaaa gttttggttc gcccaagcaa ttgctgctaa ctatgatcct | 480 |
| aaagaggcta atggttttac aaattataaa ggattttccg ctctatatat gtatggcatc | 540 |
| acagattctc tatcattcag agcttatggg gcttactcca aaccagcaaa cgataaactc | 600 |
| ggcagtgatt ttactttccg aaagtttgat ctaggtataa tttcagcgtt ttaagtcaaa | 660 |
| ttttaataaa atctttaaaa acaggctcgc attaattatt agtgagagct ttttttttat | 720 |
| ttttataat aaaactaaaa gatttttatt attttttgag ttttt atg gtt aat cct | 777 |
|                                                         Met Val Asn Pro<br>                                                                  1 | |
| att ggt cca ggt cct ata gac gaa aca gaa cgc aca cct ccc gca gat<br>Ile Gly Pro Gly Pro Ile Asp Glu Thr Glu Arg Thr Pro Pro Ala Asp<br> 5                        10                    15                    20 | 825 |
| ctt tct gct caa gga ttg gag gcg agt gca gca aat aag agt gcg gaa<br>Leu Ser Ala Gln Gly Leu Glu Ala Ser Ala Ala Asn Lys Ser Ala Glu<br>               25                    30                    35 | 873 |
| gct caa aga ata gca ggt gcg gaa gct aag cct aaa gaa tct aag acc<br>Ala Gln Arg Ile Ala Gly Ala Glu Ala Lys Pro Lys Glu Ser Lys Thr<br>        40                    45                    50 | 921 |
| gat tct gta gag cga tgg agc atc ttg cgt tct gca gtg aat gct ctc<br>Asp Ser Val Glu Arg Trp Ser Ile Leu Arg Ser Ala Val Asn Ala Leu<br>55                    60                    65 | 969 |
| atg agt ctg gca gat aag ctg ggt att gct tct agt aac agc tcg tct<br>Met Ser Leu Ala Asp Lys Leu Gly Ile Ala Ser Ser Asn Ser Ser Ser<br>    70                    75                    80 | 1017 |
| tct act agc aga tct gca gac gtg gac tca acg aca gcg acc gca cct<br>Ser Thr Ser Arg Ser Ala Asp Val Asp Ser Thr Thr Ala Thr Ala Pro<br>85                    90                    95                   100 | 1065 |
| acg cct cct cca ccc acg ttt gat gat tat aag act caa gcg caa aca<br>Thr Pro Pro Pro Pro Thr Phe Asp Asp Tyr Lys Thr Gln Ala Gln Thr<br>                  105                   110                  115 | 1113 |
| gct tac gat act atc ttt acc tca aca tca cta gct gac ata cag gct<br>Ala Tyr Asp Thr Ile Phe Thr Ser Thr Ser Leu Ala Asp Ile Gln Ala<br>             120                    125                  130 | 1161 |
| gct ttg gtg agc ctc cag gat gct gtc act aat ata aag gat aca gcg<br>Ala Leu Val Ser Leu Gln Asp Ala Val Thr Asn Ile Lys Asp Thr Ala<br>        135                    140                    145 | 1209 |
| gct act gat gag gaa acc gca atc gct gcg gag tgg gaa act aag aat<br>Ala Thr Asp Glu Glu Thr Ala Ile Ala Ala Glu Trp Glu Thr Lys Asn<br>150                    155                    160 | 1257 |
| gcc gat gca gtt aaa gtt ggc gcg caa att aca gaa tta gcg aaa tat<br>Ala Asp Ala Val Lys Val Gly Ala Gln Ile Thr Glu Leu Ala Lys Tyr | 1305 |

-continued

```
                   165                 170                 175                 180
gct tcg gat aac caa gcg att ctt gac tct tta ggt aaa ctg act tcc    1353
Ala Ser Asp Asn Gln Ala Ile Leu Asp Ser Leu Gly Lys Leu Thr Ser
                185                 190                 195 ttc gac ctc tta cag gct gct ctt ctc caa tct gta gca aac aat aac    1401
Phe Asp Leu Leu Gln Ala Ala Leu Leu Gln Ser Val Ala Asn Asn Asn
            200                 205                 210 aaa gca gct gag ctt ctt aaa gag atg caa gat aac cca gta gtc cca    1449
Lys Ala Ala Glu Leu Leu Lys Glu Met Gln Asp Asn Pro Val Val Pro
        215                 220                 225 ggg aaa acg cct gca att gct caa tct tta gtt gat cag aca gat gct    1497
Gly Lys Thr Pro Ala Ile Ala Gln Ser Leu Val Asp Gln Thr Asp Ala
    230                 235                 240 aca gcg aca cag ata gag aaa gat gga aat gcg att agg gat gca tat    1545
Thr Ala Thr Gln Ile Glu Lys Asp Gly Asn Ala Ile Arg Asp Ala Tyr
245                 250                 255                 260 ttt gca gga cag aac gct agt gga gct gta gaa aat gct aaa tct aat    1593
Phe Ala Gly Gln Asn Ala Ser Gly Ala Val Glu Asn Ala Lys Ser Asn
                265                 270                 275 aac agt ata agc aac ata gat tca gct aaa gca gca atc gct act gct    1641
Asn Ser Ile Ser Asn Ile Asp Ser Ala Lys Ala Ala Ile Ala Thr Ala
            280                 285                 290 aag aca caa ata gct gaa gct cag aaa aag ttc ccc gac tct cca att    1689
Lys Thr Gln Ile Ala Glu Ala Gln Lys Lys Phe Pro Asp Ser Pro Ile
        295                 300                 305 ctt caa gaa gcg gaa caa atg gta ata cag gct gag aaa gat ctt aaa    1737
Leu Gln Glu Ala Glu Gln Met Val Ile Gln Ala Glu Lys Asp Leu Lys
    310                 315                 320 aat atc aaa cct gca gat ggt tct gat gtt cca aat cca gga act aca    1785
Asn Ile Lys Pro Ala Asp Gly Ser Asp Val Pro Asn Pro Gly Thr Thr
325                 330                 335                 340 gtt gga ggc tcc aag caa caa gga agt agt att ggt agt att cgt gtt    1833
Val Gly Gly Ser Lys Gln Gln Gly Ser Ser Ile Gly Ser Ile Arg Val
                345                 350                 355 tcc atg ctg tta gat gat gct gaa aat gag acc gct tcc att ttg atg    1881
Ser Met Leu Leu Asp Asp Ala Glu Asn Glu Thr Ala Ser Ile Leu Met
            360                 365                 370 tct ggg ttt cgt cag atg att cac atg ttc aat acg gaa aat cct gat    1929
Ser Gly Phe Arg Gln Met Ile His Met Phe Asn Thr Glu Asn Pro Asp
        375                 380                 385 tct caa gct gcc caa cag gag ctc gca gca caa gct aga gca gcg aaa    1977
Ser Gln Ala Ala Gln Gln Glu Leu Ala Ala Gln Ala Arg Ala Ala Lys
    390                 395                 400 gcc gct gga gat gac agt gct gct gca gcg ctg gca gat gct cag aaa    2025
Ala Ala Gly Asp Asp Ser Ala Ala Ala Ala Leu Ala Asp Ala Gln Lys
405                 410                 415                 420 gct tta gaa gcg gct cta ggt aaa gct ggg caa caa cag ggc ata ctc    2073
Ala Leu Glu Ala Ala Leu Gly Lys Ala Gly Gln Gln Gln Gly Ile Leu
                425                 430                 435 aat gct tta gga cag atc gct tct gct gct gtt gtg agc gca gga gta    2121
Asn Ala Leu Gly Gln Ile Ala Ser Ala Ala Val Val Ser Ala Gly Val
            440                 445                 450 ctc ccg ctg cag caa gtt cta tgg atc cga gct cgg tac caa gct tac    2169
Leu Pro Leu Gln Gln Val Leu Trp Ile Arg Ala Arg Tyr Gln Ala Tyr
        455                 460                 465 gta gaa caa aaa ctc atc tca gaa gag gat ctg aat agc gcc gtc gac    2217
Val Glu Gln Lys Leu Ile Ser Glu Glu Asp Leu Asn Ser Ala Val Asp
    470                 475                 480 cat cat cat cat cat cat tga                                        2238
```

```
His His His His His His
485             490

<210> SEQ ID NO 8
<211> LENGTH:   490
<212> TYPE: PRT
<213> ORGANISM: Chlamydia pneumoniae

<400> SEQUENCE: 8

Met Val Asn Pro Ile Gly Pro Gly Pro Ile Asp Glu Thr Glu Arg Thr
 1               5                  10                  15

Pro Pro Ala Asp Leu Ser Ala Gln Gly Leu Glu Ala Ser Ala Ala Asn
            20                  25                  30

Lys Ser Ala Glu Ala Gln Arg Ile Ala Gly Ala Glu Ala Lys Pro Lys
        35                  40                  45

Glu Ser Lys Thr Asp Ser Val Glu Arg Trp Ser Ile Leu Arg Ser Ala
    50                  55                  60

Val Asn Ala Leu Met Ser Leu Ala Asp Lys Leu Gly Ile Ala Ser Ser
65                  70                  75                  80

Asn Ser Ser Ser Ser Thr Ser Arg Ser Ala Asp Val Asp Ser Thr Thr
                85                  90                  95

Ala Thr Ala Pro Thr Pro Pro Pro Thr Phe Asp Asp Tyr Lys Thr
            100                 105                 110

Gln Ala Gln Thr Ala Tyr Asp Thr Ile Phe Thr Ser Thr Ser Leu Ala
        115                 120                 125

Asp Ile Gln Ala Ala Leu Val Ser Leu Gln Asp Ala Val Thr Asn Ile
    130                 135                 140

Lys Asp Thr Ala Ala Thr Asp Glu Glu Thr Ala Ile Ala Ala Glu Trp
145                 150                 155                 160

Glu Thr Lys Asn Ala Asp Ala Val Lys Val Gly Ala Gln Ile Thr Glu
                165                 170                 175

Leu Ala Lys Tyr Ala Ser Asp Asn Gln Ala Ile Leu Asp Ser Leu Gly
            180                 185                 190

Lys Leu Thr Ser Phe Asp Leu Leu Gln Ala Ala Leu Leu Gln Ser Val
        195                 200                 205

Ala Asn Asn Asn Lys Ala Ala Glu Leu Leu Lys Glu Met Gln Asp Asn
    210                 215                 220

Pro Val Val Pro Gly Lys Thr Pro Ala Ile Ala Gln Ser Leu Val Asp
225                 230                 235                 240

Gln Thr Asp Ala Thr Ala Thr Gln Ile Glu Lys Asp Gly Asn Ala Ile
                245                 250                 255

Arg Asp Ala Tyr Phe Ala Gly Gln Asn Ala Ser Gly Ala Val Glu Asn
            260                 265                 270

Ala Lys Ser Asn Asn Ser Ile Ser Asn Ile Asp Ser Ala Lys Ala Ala
        275                 280                 285

Ile Ala Thr Ala Lys Thr Gln Ile Ala Glu Ala Gln Lys Lys Phe Pro
    290                 295                 300

Asp Ser Pro Ile Leu Gln Glu Ala Glu Gln Met Val Ile Gln Ala Glu
305                 310                 315                 320

Lys Asp Leu Lys Asn Ile Lys Pro Ala Asp Gly Ser Asp Val Pro Asn
                325                 330                 335

Pro Gly Thr Thr Val Gly Gly Ser Lys Gln Gln Gly Ser Ser Ile Gly
            340                 345                 350

Ser Ile Arg Val Ser Met Leu Leu Asp Asp Ala Glu Asn Glu Thr Ala
        355                 360                 365
```

```
Ser Ile Leu Met Ser Gly Phe Arg Gln Met Ile His Met Phe Asn Thr
    370                 375                 380

Glu Asn Pro Asp Ser Gln Ala Ala Gln Glu Leu Ala Ala Gln Ala
385                 390                 395                 400

Arg Ala Ala Lys Ala Ala Gly Asp Asp Ser Ala Ala Ala Leu Ala
                405                 410                 415

Asp Ala Gln Lys Ala Leu Glu Ala Ala Leu Gly Lys Ala Gly Gln Gln
            420                 425                 430

Gln Gly Ile Leu Asn Ala Leu Gly Ile Ala Ser Ala Ala Val Val
        435                 440                 445

Ser Ala Gly Val Leu Pro Leu Gln Gln Val Leu Trp Ile Arg Ala Arg
    450                 455                 460

Tyr Gln Ala Tyr Val Glu Gln Lys Leu Ile Ser Glu Glu Asp Leu Asn
465                 470                 475                 480

Ser Ala Val Asp His His His His His His
                485                 490

<210> SEQ ID NO 9
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 9
ataagaatgc ggccgccacc atggttaatc ctattggtcc agg                     43

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 10
gcgccggatc ccttggagat aaccagaata tagag                              35

<210> SEQ ID NO 11
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 11
ataagaatgc ggccgccacc atgagtctgg cagataagct ggg                     43

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 12
gcgccggatc ccttggagat aaccagaata ta                                 32

<210> SEQ ID NO 13
<211> LENGTH: 38
<212> TYPE: DNA
<213> ORGANISM: Artificial Sequence
<220> FEATURE:
```

-continued

```
<223> OTHER INFORMATION: Description of Artificial Sequence: Primer

<400> SEQUENCE: 13
gctctagacc gccatgacaa aaaaacatta tgcttggg                              38

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 14
cgggatccat agaacttgct gcagcggg                                         28
```

The invention claimed is:

1. A method for inhibiting *Chlamydia pneumoniae* proliferation in a subject, the method comprising the step of administering to the subject a vaccine composition comprising a substantially purified protein and an adjuvant, wherein the protein comprises:
   (a) the amino acid sequence set forth in SEQ ID NO:2, or
   (b) the amino acid sequence set forth in SEQ ID NO:4, or
   (c) an amino acid sequence comprising an immunogenic fragment of SEQ ID NO:2, the fragment consisting of at least amino acids 1-452 of SEQ ID NO:2, or (d) an amino acid sequence comprising an immunogenic fragment of SEQ ID NO:2, the fragment consisting of at least amino acids 69-651 of SEQ ID NO:2;

wherein the adjuvant facilitates delivery and/or enhances an immune response to the part of the protein having the amino acid sequence defined in (a) to (d).

2. The method according to claim 1 wherein the protein comprises the amino acid sequence set forth in SEQ ID NO:2.

3. The method according to claim 1 wherein the protein comprises the amino acid sequence set forth in SEQ ID NO:4.

4. The method according to claim 1 wherein the protein consists of the amino acid sequence set forth in SEQ ID NO:6.

5. The method according to claim 1 wherein the protein is a fusion protein comprising the amino acid sequence defined in (a) to (d), fused with a heterologous polypeptide.

6. The method according to claim 5 wherein the heterologous polypeptide is a peptide tail for purifying the protein.

7. The method according to claim 1 wherein the adjuvant is a liposome.

8. The method according to claim 7 wherein the liposome is at least one liposome selected from the group consisting of neutral liposomes, anionic liposomes, microspheres, ISCOMS, and virus-like-particles (VLPs).

9. The method according to claim 1, wherein the vaccine composition is administered parenterally.

10. The method according to claim 9 wherein the adjuvant is at least one adjuvant selected from the group consisting of an aluminum compound, RIBI, polyphosphazene, DC-chol (3 b-(N—(N',N'-dimethyl aminomethane)-carbamoyl) cholesterol and QS-21.

11. The method according to claim 10 wherein the adjuvant is aluminum hydroxide, aluminum phosphate, or aluminum hydroxy phosphate.

12. The method according to claim 2, wherein the vaccine composition is administered parenterally.

13. The method according to claim 12 wherein the adjuvant is at least one adjuvant selected from the group consisting of an aluminum compound, RIBI, polyphosphazene, DC-chol (3 b-(N—(N',N'-dimethyl aminomethane)-carbamoyl) cholesterol and QS-21.

14. The method according to claim 13 wherein the adjuvant is aluminum hydroxide, aluminum phosphate, or aluminum hydroxy phosphate.

15. The method according to claim 3 wherein the vaccine composition is administered parenterally.

16. The method according to claim 15 wherein the adjuvant is at least one adjuvant selected from the group consisting of an aluminum compound, RIBI, polyphosphazene, DC-chol (3 b-(N—(N',N'-dimethyl aminomethane)-carbamoyl) cholesterol and QS-21.

17. The method according to claim 16 wherein the adjuvant is aluminum hydroxide, aluminum phosphate, or aluminum hydroxy phosphate.

18. The method according to claim 4 wherein the vaccine composition is administered parenterally.

19. The method according to claim 18 wherein the adjuvant is at least one adjuvant selected from the group consisting of an aluminum compound, RIBI, polyphosphazene, DC-chol (3 b-(N—(N',N'-dimethyl aminomethane)-carbamoyl) cholesterol and QS-21.

20. The method according to claim 19 wherein the adjuvant is aluminum hydroxide, aluminum phosphate, or aluminum hydroxy phosphate.

21. The method according to claim 1, wherein the vaccine composition is administered mucosally.

22. The method according to claim 21 wherein the adjuvant is at least one adjuvant selected from the group consisting of bacterial toxin, bacterial monophosphoryl lipid A (MPLA), saponin, polylactide glycolide (PLGA) microsphere, polyphosphazene, DC-chol (3 b-(N—(N',N'-dimethyl aminomethane)-carbamoyl) cholesterol, and QS-21.

23. The method according to claim 22 wherein the adjuvant is at least one bacterial toxin selected from the group consisting of cholera toxin (CT), *E. coli* heat-labile toxin (LT), Clostridium difficile toxin A, pertussis toxin (PT), and combinations, subunits, toxoids, or mutants thereof that retain adjuvant activity and/or have reduced toxicity.

24. The method according to claim 23 wherein the adjuvant is at least one bacterial toxin selected from the group consisting of native cholera toxin subunit B (CTB), Arg-7-Lys CT mutant, Arg-192-Gly LT mutant, Arg-9-Lys PT mutant, Glu-129-Gly PT mutant, Ser-63-Lys LT mutant, Ala-69-Gly LT mutant, Glu-110-Asp LT mutant, and Glu-112-Asp LT mutant.

25. The method according to claim 22 wherein the adjuvant is bacterial monophosphoryl lipid A (MPLA) of *E. coli, Salmonella minnesota, Salmonella typhimurium,* or *Shigella flexneri.*

26. The method according to claim 2, wherein the vaccine composition is administered mucosally.

27. The method according to claim 26 wherein the adjuvant is at least one adjuvant selected from the group consisting of bacterial toxin, bacterial monophosphoryl lipid A (MPLA), saponin, polylactide glycolide (PLGA) microsphere, polyphosphazene, DC-chol (3 b-(N—(N',N'-dimethyl aminomethane)-carbamoyl) cholesterol, and QS-21.

28. The method according to claim 27 wherein the adjuvant is at least one bacterial toxin selected from the group consisting of cholera toxin (CT), *E. coli* heat-labile toxin (LT), Clostridium difficile toxin A, pertussis toxin (PT), and combinations, subunits, toxoids, or mutants thereof that retain adjuvant activity and/or have reduced toxicity.

29. The method according to claim 28 wherein the adjuvant is at least one bacterial toxin selected from the group consisting of native cholera toxin subunit B (CTB), Arg-7-Lys CT mutant, Arg-192-Gly LT mutant, Arg-9-Lys PT mutant, Glu-129-Gly PT mutant, Ser-63-Lys LT mutant, Ala-69-Gly LT mutant, Glu-110-Asp LT mutant, and Glu-112-Asp LT mutant.

30. The method according to claim 27 wherein the adjuvant is bacterial monophosphoryl lipid A (MPLA) of *E. coli, Salmonella minnesota, Salmonella typhimurium,* or *Shigella flexneri.*

31. The method according to claim 3, wherein the vaccine composition is administered mucosally.

32. The method according to claim 31 wherein the adjuvant is at least one adjuvant selected from the group consisting of bacterial toxin, bacterial monophosphoryl lipid A (MPLA), saponin, polylactide glycolide (PLGA) microsphere, polyphosphazene, DC-chol (3 b-(N—(N',N'-dimethyl aminomethane)-carbamoyl) cholesterol, and QS-21.

33. The method according to claim 32 wherein the adjuvant is at least one bacterial toxin selected from the group consisting of cholera toxin (CT), *E. coli* heat-labile toxin (LT), Clostridium difficile toxin A, pertussis toxin (PT), and combinations, subunits, toxoids, or mutants thereof that retain adjuvant activity and/or have reduced toxicity.

34. The method according to claim 33 wherein the adjuvant is at least one bacterial toxin selected from the group consisting of native cholera toxin subunit B (CTB), Arg-7-Lys CT mutant, Arg-192-Gly LT mutant, Arg-9-Lys PT mutant, Glu-129-Gly PT mutant, Ser-63-Lys LT mutant, Ala-69-Gly LT mutant, Glu-110-Asp LT mutant, and Glu-112-Asp LT mutant.

35. The method according to claim 32 wherein the adjuvant is bacterial monophosphoryl lipid A (MPLA) of *E. coli, Salmonella minnesota, Salmonella typhimurium,* or *Shigella flexneri.*

36. The method according to claim 4, wherein the vaccine composition is administered mucosally.

37. The method according to claim 36 wherein the adjuvant is at least one adjuvant selected from the group consisting of bacterial toxin, bacterial monophosphoryl lipid A (MPLA), saponin, polylactide glycolide (PLGA) microsphere, polyphosphazene, DC-chol (3 b-(N—(N',N'-dimethyl aminomethane)-carbamoyl) cholesterol, and QS-21.

38. The method according to claim 37 wherein the adjuvant is at least one bacterial toxin selected from the group consisting of cholera toxin (CT), *E. coli* heat-labile toxin (LT), Clostridium difficile toxin A, pertussis toxin (PT), and combinations, subunits, toxoids, or mutants thereof that retain adjuvant activity and/or have reduced toxicity.

39. The method according to claim 38 wherein the adjuvant is at least one bacterial toxin selected from the group consisting of native cholera toxin subunit B (CTB), Arg-7-Lys CT mutant, Arg-192-Gly LT mutant, Arg-9-Lys PT mutant, Glu-129-Gly PT mutant, Ser-63-Lys LT mutant, Ala-69-Gly LT mutant, Glu-110-Asp LT mutant, and Glu-112-Asp LT mutant.

40. The method according to claim 37 wherein the adjuvant is bacterial monophosphoryl lipid A (MPLA) of *E. coli, Salmonella minnesota, Salmonella typhimurium,* or *Shigella flexneri.*

41. The method according to claim 1, wherein the vaccine composition further comprises an additional *Chlamydia* polypeptide that enhances an immune response to the part of the protein having the amino acid sequence defined in (a) to (d).

42. The method according to claim 5 wherein the protein comprises the amino acid sequence set forth in SEQ ID NO:2.

43. The method according to claim 5 wherein the protein comprises the amino acid sequence set forth in SEQ ID NO:4.

44. The method according to claim 5 wherein the protein consists of the amino acid sequence set forth in SEQ ID NO:6.

45. The method according to claim 5 wherein the heterologous polypeptide has adjuvant activity.

46. The method according to claim 45 wherein the heterologous polypeptide having adjuvant activity is suitable as an adjuvant for parenteral administration.

47. The method according to claim 45 wherein the heterologous polypeptide having adjuvant activity is suitable as an adjuvant for mucosal administration.

48. The method according to claim 47 wherein the heterologous polypeptide is subunit B of cholera toxin (CTB) or subunit B of *E. coli* heat-labile toxin (LTB).

49. The method according to claim 45 wherein the heterologous polypeptide is a strong T-cell epitope and/or a strong B-cell epitope.

50. The method according to claim 49 wherein the heterologous polypeptide is a strong T-cell epitope and/or a strong B-cell epitope from hepatitis B virus core antigen.

51. The method according to claim 5 wherein the adjuvant is a liposome.

52. A method for inhibiting *Chlamydia pneumoniae* proliferation in a subject, the method comprising the step of mucosally administering to the subject a vaccine composition comprising a substantially purified protein and an adjuvant, wherein the protein comprises:

(a) the amino acid sequence set forth in SEQ ID NO:2, or
(b) the amino acid sequence set forth in SEQ ID NO:4, or
(c) an amino acid sequence comprising an immunogenic fragment of SEQ ID NO:2, the fragment consisting of at least amino acids 1-452 of SEQ ID NO:2, or
(d) an amino acid sequence comprising an immunogenic fragment of SEQ ID NO:2, the fragment consisting of at least amino acids 69-651 of SEQ ID NO:2;
wherein the adjuvant facilitates delivery and/or enhances an immune response to the part of the protein having the amino acid sequence defined in (a) to (d), wherein the vaccine composition;
and further comprising the step of administering to the subject an antibiotic, an antacid, sucralfate, a cytokine immunomodulator or a combination thereof.

53. The method according to claim 52 wherein the antibiotic is a macrolide, a tetracycline, or a derivative thereof.

54. The method according to claim 52 wherein the antibiotic is azithromycin or doxycyclin, and wherein the immunomodulator is interleukin-2 (IL-2), interleukin-12 (IL-12), or a steroid.

* * * * *